US012668788B2

(12) United States Patent
Tam et al.

(10) Patent No.: US 12,668,788 B2
(45) Date of Patent: Jun. 30, 2026

(54) ASX-SPECIFIC PROTEIN LIGASES AND USES THEREOF

(71) Applicant: NANYANG TECHNOLOGICAL UNIVERSITY, Singapore (SG)

(72) Inventors: James P. Tam, Singapore (SG); Julien Lescar, Singapore (SG); Muxinya He, Singapore (SG); Abbas El Sahili, Singapore (SG); Chuan Fa Liu, Singapore (SG); Side Hu, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 744 days.

(21) Appl. No.: 17/608,966

(22) PCT Filed: May 6, 2020

(86) PCT No.: PCT/SG2020/050267
§ 371 (c)(1),
(2) Date: Nov. 4, 2021

(87) PCT Pub. No.: WO2020/226572
PCT Pub. Date: Nov. 12, 2020

(65) Prior Publication Data
US 2022/0213461 A1 Jul. 7, 2022

(30) Foreign Application Priority Data

May 7, 2019 (SG) .......................... 10201904085W
Nov. 19, 2019 (SG) ............................ 10201910861S

(51) Int. Cl.
| | |
|---|---|
| *C12N 9/50* | (2006.01) |
| *C12N 9/00* | (2006.01) |
| *C12N 11/06* | (2006.01) |
| *C12N 15/52* | (2006.01) |

(52) U.S. Cl.
CPC ................. *C12N 9/63* (2013.01); *C12N 9/93* (2013.01); *C12N 11/06* (2013.01); *C12N 15/52* (2013.01)

(58) Field of Classification Search
CPC .................................. C12N 9/93; C12N 15/52
USPC ....................................................... 435/219
See application file for complete search history.

(56) References Cited

U.S. PATENT DOCUMENTS

| | | | | |
|---|---|---|---|---|
| 10,590,407 | B2 * | 3/2020 | Nguyen ................. | C12P 21/02 |
| 11,124,788 | B2 | 9/2021 | Nguyen et al. | |
| 2010/0158924 | A1 | 6/2010 | Clerin et al. | |
| 2013/0097737 | A1 | 4/2013 | Kovalic et al. | |
| 2014/0259212 | A1 | 9/2014 | Plesch et al. | |
| 2017/0044515 | A1 * | 2/2017 | Nguyen ................. | C12P 21/02 |

FOREIGN PATENT DOCUMENTS

| | | | | |
|---|---|---|---|---|
| WO | 2015/163818 A1 | 10/2015 | | |
| WO | WO-2017049362 A1 * | 3/2017 | ............. | A01N 63/02 |

OTHER PUBLICATIONS

NCBI Accession # QCW05335, Hemu et al. Direct Submission, Submitted (Oct. 23, 2018) School of Biological Sciences, Nanyang Technological University, 60 Nanyang Drive, Singapore 637551, Singapore (Year: 2018).*
Friedberg, Brief. Bioinformatics (2006) 7: 225-242 (Year: 2006).*
Thorton et al. Nature structural biology, structural genomics supplement, Nov. 2000, pp. 991-994 (Year: 2000).*
Altschul et al., "Basic Local Alignment Search Tool," *J. Mol. Biol.* 215:403-410, 1990.
Altschul et al., "Gapped BLAST and PSI-BLAST: a new generation of protein database search programs," *Nucleic Acids Res.* 25(17):3389-3402, 1997.
Anderson et al., "The Use of Esters of N-Hydroxysuccinimide in Peptide Synthesis," *J. Am. Chem. Soc.* 86:1839-1842, May 3, 1964.
Arnison et al., "Ribosomally synthesized and post-translationally, modified peptide natural products: overview and recommendations for a universal nomenclature," *Natural Products Reports* 30:108-160, 2013.
Barber et al., "The Two-step Biosynthesis of Cyclic Peptides from Linear Precursors in a Member of the Plant Family Caryophyllaceae Involves Cyclization by a Serine Protease-like Enzyme," *The Journal of Biological Chemistry* 288(18):12500-12510, May 3, 2013.
Barrett et al., "Evolutionary Lines of Cysteine Peptidases," *Biological Chemistry* 382:727-733, May 2001.
Becker et al., "The Covalent and Three-Dimensional Structure of Concanavalin A: III. Structure of the Monomer and its Interactions with Metals and Saccharides," *J. Bio. Chem.* 250:1513-1524, Feb. 25, 1975.
Bernath-Levin et al., "Peptide Macrocyclization by a Bifunctional Endoprotease" *Chemistry & Biology* 22(1):571-582, 2015.
Best et al., "Optimization of the additive CHARMM All-Atom Protein Force Field Targeting Improved Sampling of the Backbone $\varphi$, $\psi$ and Side-Chain $_{102\ 1}$ and $_{102\ 2}$ Dihedral Angles," *J. Chem. Theory Comput.* 8(9):3257-3273, 2012.
Bi et al., "Enzymatic Engineering of Live Bacterial Cell Surfaces Using Butelase 1," *Angewandte Chemie International Edition* 56:7822-7825, 2017.
Bowles et al., "Posttranslational Processing of Concanavalin A Precursors in Jackbean Cotyledons," *the Journal of Cell Biology* 102:1284-1297, Apr. 1986.
Cao et al., "Butelase-mediated synthesis of protein thioesters and its application for tandem chemoenzymatic ligation," *Chemical Communications* 51:17289-17292, 2015.

(Continued)

*Primary Examiner* — Louise W Humphrey
*Assistant Examiner* — Jessica Faye Edwards
(74) *Attorney, Agent, or Firm* — Seed IP Law Group LLP

(57) ABSTRACT

The present invention lies in the technical field of enzyme technology and specifically relates to enzymes having Asx-specific ligase and cyclase activity and to nucleic acids encoding those as well as methods of the manufacture of said enzymes. The enzymes having Asx-specific ligase and cyclase are isolated from plants of the Violaceae family. Further encompassed are methods and uses of these enzymes.

9 Claims, 11 Drawing Sheets
Specification includes a Sequence Listing.

(56)          References Cited

OTHER PUBLICATIONS

Cao et al., "Cross-Linked Enzyme Aggregates: A Simple and Effective Method for the Immobilization of Penicillin Acylase," *Org. Lett.* 2(10): 1361-1364, Jan. 28, 2000.

Carrington et al., "Polypeptide ligation occurs during post-translational modification of concanavalin A," *Nature* 313(3)64-67, Jan. 3, 1985.

Chang et al., "Subtiligase: A tool for semisynthesis of proteins," *Proceedings of the National Academy of Science USA* 91:12544-12548, Dec. 1994.

Chekan et al., "Characterization of the macrocyclase involved in the biosynthesis of RiPP cyclic peptides in plants," *PNAS* 114(25):6551-6556, Jun. 20, 2017.

Chen et al., "Activation of human prolegumain by cleavage at a C-terminal asparagine residue," *Biochemical Journal* 352:327-334, 2000.

Chen et al., "Identification of the active site of legumain links it to caspases, clostripain and gingipains in a new clan of cysteine endopeptidases," *FEBS Letters* 441:361-365, 1998.

Conlan et al., "Review: Circular Proteins and Mechanisms of Cyclization," *Peptide Science* 94(5):573-583, 2010.

Cuatrecasas, et al., "Adsorbents for Affinity Chromatography. Use of N-Hydroxysuccinimide Esters of Agarose," *Biochemistry* 11(12):2291-2299, 1972.

Dall et al., "Mechanistic and structural studies on legumain explain its zymogenicity, distinct activation pathways, and regulation," *PNAS* 110(27):10940-10945, Jul. 2, 2013.

Dall et al., "Structure and Mechanism of an Aspartimide-Dependent Peptide Ligase in Human Legumain" *Angewandte Chemie International Edition* 54(10):2917-2921, 2015.

Datta et al., "Enzyme immobilization: an overview on techniques and support materials," *3 Biotech.* 3(1):1-9, 2013.

De Souza Cândido et al., "Plant storage proteins with antimicrobial activity: novel insights into plant defense mechanisms" *The FASEB Journal* 25(10):3290-3305, 2011.

DiCosimo et al., "Industrial use of immobilized enzymes," *Chem. Soc. Rev.* 42(15): 6437-6474, 2013.

Dulaney, "Binding Interactions of Glycoproteins with Lectins," *Mol. Cell. Biochem.* 21(1):43-63, Oct. 13, 1979.

Goldstein et al., "Protein-Carbohydrate Interaction. II. Inhibition Studies on the Interaction of Concanavalin A with Polysaccharides," *Biochemistry* 4(5):876-883, 1965.

Green "Spectrophotometric Determination of Avidin and Biotin," Methods Enzymol. *Academic Press* 18(A):418-424, 1970.

Haase et al., A Specific Protease Encoded by the Conjugative DNA Transfer Systems of IncP and Ti Plasmids Is Essential for Pilus Synthesis, *Journal of Bacteriology* 179(18):5728-5735, Sep. 1997.

Halfon et al., "Autocatalytic activation of human legumain at aspartic acid residues," *FEBS Letters* 438:114-118, 1998.

Hara-Nishimura et al., "Vacuolar processing enzyme: an executor of plant cell death" *Current Opinion in Plant Biology* 8(1):404-408, 2005.

Harmand et al., "One-Pot Dual Labeling of IgG 1 and Preparation of C-to-C Fusion Proteins Through a Combination of Sortase A and Butelase 1," *Bioconjugate Chem.* 29:3245-3249, 2018.

Harris et al., "A suite of kinetically superior AEP ligases can cyclise an intrinsically disordered protein," *Sci. Rep.* 9(10820):1-13, 2019.

Harris et al., "Efficient backbone cyclization of linear peptides by a recombinant asparaginyl endopeptidase," *Nature Communications* 6(10199):1-10, Dec. 18, 2015.

Hatsugai et al., "A Plant Vacuolar Protease, VPE, Mediates Virus-Induced Hypersensitive Cell Death" *Science* 305:855-858, 2004.

Hatsugai et al., "Vacuolar processing enzyme in plant programmed cell death" *Frontiers in Plant Science* 6(234):1-11, Apr. 9, 2015.

Haywood et al., "Structural basis of ribosomal peptide macrocyclization in plants," *eLIFE* 7(e32955):1-22, 2018.

Hemu et al. "Ligase-Controlled Cyclo-oligomerization of Peptides," *Org. Lett.* 21:2029-2032, Feb. 14, 2019.

Hemu et al., "Chapter 26: Peptidomic Identification of Cysteine-Rich Peptides from Plants," Peptidomics: Methods and Strategies, eds. Schrader et al, *Methods of Molecular Biology* 1719:379-393, 2018.

Hemu et al., "Immobilized Peptide Asparaginyl Ligases Enhance Stability and Facilitate Macrocyclization and Site-Specific Ligation," *J. Org. Chem.* 85:1504-1512, 2020.

Hemu et al., "Structural determinants for peptide-bond formation by asparaginyl ligases," *PNAS* 116(24):11737-11746, Jun. 11, 2019.

Hemu et al., "Total Synthesis of Circular Bacteriocins by Butelase 1," *Journal of the American Chemical Society* 138:6968-6971, May 20, 2016.

Hiraiwa et al., "Vacuolar processing enzyme is self-catalytically activated by sequential removal of the C-terminal and N-terminal propeptides," *FEBS Letters* 447:213-216, 1999.

Humphrey et al., "VMD: Visual Molecular Dynamics," *J. Mol. Graph.* 14:33-38, 1996.

Jackson et al., "Molecular basis for the production of cyclic peptides by plant asparaginyl endopeptidases," *Nature Communications* 9(2411):1-12, 2018.

Jesionowski et al., "Enzyme immobilization by adsorption: a review," *Adsorption* 20:801-821, 2014.

Jost et al., "Structural Basis for Eliciting a Cytotoxic Effect in HER2-Overexpressing Cancer Cells via Binding to the Extracellular Domain of HER2," *Structure* 21(11):1979-1991, Nov. 5, 2013.

Kabsch, "XDS," *Acta. Cryst.* D66:125-132, 2010.

Kaur et al., "*Listeria monocytogenes* in spontaneous abortions in humans and its detection by multiplex Pcr," *J. Appl. Microbiol.* 103:1889-1896, Mar. 25, 2007.

Klibanov et al., "Immobilized Enzymes and Cells as Practical Catalysts," *Science* 219(4585):722-727, Feb. 11, 1983.

Klibanov, "Enzyme Stabilization by Immobilization," *Anal. Biochem.* 93:1-25, 1979.

Kuroyanagi et al., "Activation of Arabidopsis Vacuolar Processing Enzyme by Self-Catalytic Removal of an Auto-Inhibitory Domain of the Cterminal Propeptide," *Plant Cell Physiology* 43(2):143-151, 2002.

Liese et al., "Evaluation of immobilized enzymes for industrial applications," *Chem. Soc. Rev.* 42(15):6236-6249, 2013.

Livnah et al., "Three-dimensional structures of avidin and the avidin—biotin complex," *PNAS* 90:5076-5080, Jun. 1993.

Loo et al., "Bleogens: Cactus-Derived Anti-Candida Cysteine-Rich Peptides with Three Different Precursor Arrangements," *Frontiers in Plant Science* 8:2162, Dec. 22, 2017.

Low et al., "A review of *Listeria monocytogenes* and Listeriosis," Vet. J. 153(1):9-29, 1997.

Luo et al., "Peptide Macrocyclization Catalyzed by a Prolyl Oligopeptidase Involved in α-Amanitin Biosynthesis," *Chemistry & Biology* 21:1610-1617, Dec. 18, 2014.

Mann et al., "The structure of the cyanobactin domain of unknown function from PatG in the patellamide gene cluster," *Structural Biology Communications* F70:1597-1603, Nov. 3, 2014.

Mao et al., "Sortase-Mediated Protein Ligation: A New Method for Protein Engineering," *Journal of the American Chemical Society* 126(9):2670-2671, 2004.

Mazmanian et al., "*Staphylococcus aureus* Sortase, an Enzyme that Anchors Surface Proteins to the Cell Wall," *Science* 285:760-763, Jul. 30, 1999.

Min et al., "In vitro splicing of concanavalin A is catalyzed by asparaginyl endopeptidase," *Structural Biology* 1(8):502-504, Aug. 1994.

Mindell "Lysosomal Acidification Mechanisms" *Annual Review of Physiology* 74(1):69-86, 2012.

Müntz et al., "Legumains and their functions in plants," *TRENDS in Plant Science* 7(8):1-5, 2002.

Mylne et al., "Cyclic Peptides Arising by Evolutionary Parallelism via Asparaginyl-Endopeptidase-Mediated Biosynthesis," *The Plant Cell* 24:2765-2778, Jul. 2012.

Nguyen et al., "Butelase 1 is an Asx-specific ligase enabling peptide macrocyclization and synthesis," *Nature Chemical Biology* 10:732-738, Sep. 2014.

Nguyen et al., "Butelase 1: A Versatile Ligase for Peptide and Protein Macrocyclization," *Journal of the American Chemical Society* 137:15398-15401, 2015.

(56) References Cited

OTHER PUBLICATIONS

Nguyen et al., "Butelase-mediated cyclization and ligation of peptides and proteins," *Nature Protocols* 11(10):1977-1988, 2016.

Nguyen et al., "Butelase-Mediated Macrocyclization of Ð-Amino-Acid-Containing Peptides," *Angewandte Chemie International Edition* 55:12802-12806, 2016.

Phillips et al., "Scalable molecular dynamics with NAMD," *J. Comput. Chem.* 26:1781-1802, May 26, 2005.

Piotukh et al., "Directed Evolution of Sortase A Mutants with Altered Substrate Selectivity Profiles," *Journal of the American Chemical Society* 133:17536-17539, Oct. 11, 2011.

Rodrigues et al., "Modifying enzyme activity and selectivity by immobilization," *Chem. Soc. Rev.* 42(15):6290-6307, 2013.

Rüdiger et al., "Plant lectins: Occurrence, biochemistry, functions and applications," *Glycoconjugate* 18:589-613, 2001.

Saleemuddin et al., "Concanavalin A: A useful ligand for glycoenzyme immobilization—a review," *Enzyme Microb. Technol.* 13(4):290-295, Apr. 1991.

Saska et al., "An Asparaginyl Endopeptidase Mediates in Vivo Protein Backbone Cyclization," *J. Biol. Chem.* 282(4):29721-29728, Oct. 5, 2007.

Schechter et al., "On the Size of the Active Site in Proteases. I. Papain," *Biochem. Biophys. Res. Comm.* 27(2):157-162, 1967.

Schmidt et al., "Omniligase-1: A Powerful Tool for Peptide Head-to-Tail Cyclization," *Advanced Synthesis & Catalysis* 359(12):2050-2055, 2017.

Serra et al. "A high-throughput peptidomic strategy to decipher the molecular diversity of cyclic cysteine-rich peptides," *Sci. Rep.* 6(23005):1-13, Mar. 11, 2016.

Shen et al., "Organelle pH in the *Arabidopsis* Endomembrane System" *Molecular Plant* 6(5):1419-1437, Sep. 2013.

Shi et al., "Protein N-Glycosylation in the Baculovirus-Insect Cell System," *Curr. Drug Targets* 8(10):1116-1125, 2007.

Shrestha et al., "Chapter 19: Baculovirus Expression Vector System: An Emerging Host for High-Throughput Eukaryotic Protein Expression," *Methods in Molecular Biology* 439:269-289, 2008.

Strasser, "Biological significance of complex N-glycans in plants and their impact on plant physiology," *Front. Plant. Sci.* 5(363):1-6, Jul. 2014.

Sumner et al., "The Identification of the Hemagglutinin of the Jack Bean with Concanavalin A," *J. Bacteriol.* 32(2):227-237, Mar. 15, 1936.

Tam et al., "Thia Zip Reaction for Synthesis of Large Cyclic Peptides: Mechanisms and Applications," *J. Am. Chem. Soc.* 121:4316-4324, Apr. 27, 1999.

Tischer et al., "Immobilized Enzymes: Methods and Applications," *Topics in Current Chemistry*, vol. 200, Springer Verlag, Berlin Heidelberg, pp. 95-126, 1999.

Toplak et al., "Peptiligase, an Enzyme for Efficient Chemoenzymatic Peptide Synthesis and Cyclization in Water," *Advanced Synthesis & Catalysis* 358:2140-2147, 2016.

Trabi et al., Variations in Cyclotide Expression in *Viola* Species, *J. Nat. Prod.* 67(5):806-810, 2004.

UniProtKB—A0A384E113 (A0A384E113_9ROSI), "Peptide asparaginyl ligase," last modified: Aug. 12, 2020. (5 pages).

Vermette et al., "Immobilization and surface characterization of NeutrAvidin biotin-binding protein on different hydrogel interlayers," *J. Colloid Interface Sci.* 259:13-26, 2003.

Wang et al., "Anti-HIV Cyclotides from the Chinese Medicinal Herb *Viola Yedoensis,*" *J. Nat. Prod.* 71:47-52, 2008.

Weeks et al., "Engineering peptide ligase specificity by proteomic identification of ligation sites," *Nature Chemical Biology* 14:50-57, Nov. 20, 2017. (13 pages).

Wilchek et al., "The Avidin-Biotin Complex in Bioanalytical Applications," *Anal. Biochem.* 171(1):1-32, 1988.

Wilson, "Glycosylation of proteins in plants and invertebrates," *Curr. Opin. Struct. Biol.* 12:569-577, 2002. (11 pages).

Yang et al., "Engineering a Catalytically Efficient Recombinant Protein Ligase," *J. Am. Chem. Soc.* 139(15):5351-5358, Feb. 15, 2017.

Young et al., "Magnesium as a natural substitute for manganese in concanavalin A and other lectins," *FEBS Lett.* 161(2):247-250, Sep. 1983.

Zauner et al., "Crystal Structure of Plant Legumain Reveals a Unique Two-Chain State with fpHg-Dependent Activity Regulation," *The Plant Cell* 30:686-699, Mar. 2018.

Zauner et al., "Structural analyses of *Arabidopsis thaliana* legumain γ reveal differential recognition and processing of proteolysis and ligation substrates," *J. Biol. Chem.* 293(23):8934-8946, 2018.

Zhao et al., "Structural analysis of asparaginyl endopeptidase reveals the activation mechanism and a reversible intermediate maturation stage" *Cell Research* 24(1):344-358, 2014.

Zucca et al., "Agarose and Its Derivatives as Supports for Enzyme Immobilization," *Molecules* 21(11):1-25, 2016.

Abe et al., "Asparaginyl Endopeptidase of Jack Bean Seeds—Purification, Characterization, and High Utility In Protein Sequence Analysis," *The Journal of Biological Chemistry*, 268(5):3525-3529, Feb. 1993. (5 pages).

Becker et al., "Purification, cDNA cloning and characterization of proteinase B, an asparagine-specific endopeptidase from germinating vetch (*Vicia sativa* L.) seeds," *Eur. J. Biochem* 225:456-462, Mar. 1995. (7 pages).

Bolscher et al., "Sortase A as a tool for high-yield histatin cyclization," *The FASEB Journal* 25(8):2650-2658, Jan. 2017. (10 pages).

Cascales et al., "Naturally occurring circular proteins: distribution, biosynthesis, and evolution," *Organic and Biomolecular Chemistry* 8:5035-5047, Sep. 2010. (13 pages).

Cole et al., "Retrocyclin: A primate peptide that protects cells from infection by T- and M-tropic strains of HIV-1," *PNAS* 99(4):1813-1818, Feb. 2002. (6 pages).

Conlan et al., "Insights into Processing and Cyclization Events Associated with Biosynthesis of the Cyclic Peptide Kalata B1," *The Journal of Biological Chemistry* 287(33):28037-28046, Aug. 2012. (10 pages).

Conlan et al., "Circular Micro-Proteins and Mechanisms of Cyclization," *Current Pharmaceutical Design* 17:4318-4328, Dec. 2011. (11 pages).

Craik et al., "Plant Cyclotides: a Unique Family of Cyclic and Knotted Proteins that Defines the Cyclic Cystine Knot Structural Motif," *J. Mol. Biol.* 294:1327-1336, Dec. 1999.

Craik, "Host-Defense Activities of Cyclotides," *Toxins* 4:139-156, Feb. 2012.

Craik, "Seamless Proteins Tie Up Their Loose Ends," *Science* 311:1563-1564, Mar. 2006.

Database Geneseq [Online] "Asparaginyl endopeptidase derived from clone 107," XP002772646, retrieved from EBI Accession No. AAR43039, Mar. 25, 2003.

Database Geneseq [Online] "G. max yield enhancing protein SEQ ID:164," XP002772647, retrieved from EBI Accession No. GSP: ARZ05348, Aug. 21, 2008.

Database Geneseq [Online] "Plant isolated polypeptide sequence, SEQ ID 19351," retrieved from EBI Accession No. GSP: AYF97933, Sep. 30, 2010.

Eisenbrandt et al., "Conjugative Pili of IncP Plasmids, and the Ti Plasmids T Pilus Are Composed of Cyclic Subunits," *The Journal of Biological Chemistry* 274(32):22548-22555, Aug. 1999. (9 pages).

Gharahdaghi et al., "Mass spectrometric identification of proteins from silver-stained polyacrylamide gel: A method for the removal of silver ions to enhance sensitivity," *Electrophoresis* 20:601-605, Mar. 1999.

Gillon et al., "Biosynthesis of circular proteins in plants," *The Plant Journal* 53:505-515, Feb. 2008. (11 pages).

Gruber et al., "Distribution and Evolution of Circular Miniproteins in Flowering Plants," *The Plant Cell* 20:2471-2483, Sep. 2008.

Hackeng et al., "Protein synthesis by native chemical ligation: Expanded scope by using straightforward methodology," *PNAS* 96:10068-10073, Aug. 1999.

Ho et al., "Electrospray Ionisation Mass Spectrometry and Clinical Applications," *Clin Biochem Rev* 24:3-12, Feb. 2003.

Jack et al., "Bacteriocins of Gram-Positive Bacteria," *Microbial Reviews* 59(2):171-200, Jun. 1995.

(56)  References Cited

OTHER PUBLICATIONS

Jackson et al., "Tying up loose ends : convergence of structural markers underpinning plant peptide ligases," sequence ID No. AOA2SIGHJ2_AFREN, downloaded Mar. 24, 2023. (2 pages).

Jia et al., "Semienzymatic Cyclization of Disulfide-rich Peptides Using Sortase A," *The Journal of Biological Chemistry* 289(10):6627-6638, Mar. 2014. (12 pages).

Kembhavi et al., "The Two Cysteine Endopeptidases of Legume Seeds: Purification and Characterization by Use of Specific Fluorometric Assays," *Archives of Biochemistry and Biophysics* 303(2):208-213, Jun. 1993. (6 pages).

Kleinkauf et al., "Nonribosomal Polypeptide Synthesis: The Biosynthesis of a Cyclic Peptide Antibiotic," *Cold Spring Harb Symp Quant Biol* 34:805-813, 1969.

Koehnke et al., "The mechanism of patellamide macrocyclization revealed by the characterization of the PatG macrocyclase domain," *Nat Struct Mol Biol.* 19(8):767-772, 2012 (Author Manuscript, available in PMC Oct. 2, 2012) (17 pages).

Kohli et al., "Generality of Peptide Cyclization Catalyzed by Isolated Thioesterase Domains of Nonribosomal Peptide Synthetases," *Biochemistry* 40:7099-7108, May 2001.

Lee et al., "Development of Near-Infrared Fluorophore (NIRF)-Labeled Activity-Based Probes for in Vivo Imaging of Legumain," *ACS Chemical Biology* 5(2):233-243, Dec. 2009.

Lee et al., "Using Marine Natural Products to Discover a Protease that Catalyzes Peptide Macrocyclization of Diverse Substrates," *J Am Chem Soc.* 161(6):2122-2124, Feb. 2009. (Author Manuscript, available in PMC Feb. 18, 2010) (9 pages).

Luckett et al., "High-Resolution Structure of a Potent, Cyclic Proteinase Inhibitor from Sunflower Seeds," *J. Mol. Biol.* 290:525-533, Jul. 1999. (9 pages).

Motomayor et al., "Gamma vacuolar processing enzyme [Theobroma cacao]," NCBI Reference Sequence XP_007012236.1, run on Jul. 10, 2014, retrieved from http://www.ncbi.nlm.nih.gov/protein/590573851, 2 pages.

Myline et al., "Albumins and their processing machinery are hijacked for cyclic peptides in sunflower," *Nature Chemical Biology* 7:257-259, May 2011. (3 pages).

Nguyen et al., "Discovery and Characterization of Novel Cyclotides Originated from Chimeric Precursors Consisting of Albumin-1 Chain a and Cyclotide Domains in the Fabaceae Family," *The Journal of Biological Chemistry* 286(27):24275-24287, Jul. 2011. (21 pages).

Nguyen et al., "Novel Cyclotides and Uncyclotides with Highly Shortened Precursors from *Chassalia chartacea* and Effects of Methionine Oxidation on Bioactivities," *The Journal of Biological Chemistry* 287(21):17598-17607, May 2012. (10 pages).

Nguyen et al., GenBank Accession No. KF918345.1, "Clitoria tenratea cte peptide ligase mRNA, complete cds," run on Jun. 8, 2014, retrieved from https://www.ncbi.nlm.nih.gov/nuccore/KF918345, 2 pages.

Pauletti et al., "Improvement of oral peptide bioavailability: Peptidomimetics and prodrug strategies," *Advanced Drug Delivery Reviews* 27:235-256, Sep. 1997. (22 pages).

Popp et al., "Making and Breaking Peptide Bonds: Protein Engineering Using Sortase," *Angew. Chem. Int. Ed.* 50:5024-5032, Apr. 2011. (9 pages).

Poth et al., "Discovery of Cyclotides in the Fabaceae Plant Family Provides New Insights in the Cyclization, Evolution, and Distribution of Circular Proteins," *ACS Chem. Biol.* 6:345-355, Dec. 2010. (11 pages).

Pritz et al., "Enzymatic ligation of peptides, peptide nucleic acids and proteins by means of sortase A," *Adv. Exp. Med. Biol.* 611:107-108, Feb. 2009.

Rotari et al., "Legumain Forms from Plants and Animals Differ in Their Specificity," *Biol. Chem.* 382:953-959, Jun. 2001.

Šali et al., "Comparative Protein Modelling by Satisfaction of Spatial Restraints," *J. Mol. Biol.* 234:779-815, Dec. 1993. (37 pages).

Sieber et al., "Learning from Nature's Drug Factories: Nonribosomal Synthesis of Macrocyclic Peptides," *Journal of Bacteriology* 185(24):7036-7043, Dec. 2003. (8 pages).

Sivonen et al., "Cyanobactins—ribosomal cyclic peptides produced by cyanobacteria," *Appl Microbiol Biotechnol* 86:1213-1225, Feb. 2010. (13 pages).

Sojka et al., "IrAE—an asparaginyl endopeptidase (legumain) in the gut of the hard tick *Ixodes ricinus*," *Int J Parasitol* 37(7):713-724, 2007 (Author Manuscript, available in PMC Nov. 2, 20085) (21 pages).

Strijbis et al., "Protein Ligation in Living Cells Using Sortase," *Traffic* 13:780-789, Mar. 2012. (10 pages).

Takeda et al., "Isolation and Analysis of cDNA Encoding a Precursor of *Canavalia ensiformis* Asparaginyl Endopeptidase (Legumain)," *J. Biochem* 116:541-546, Sep. 1994. (6 pages).

Tan et al., "Plant Cyclopeptides," *Chem. Rev.* 106:840-895, Feb. 2006. (56 pages).

Tang et al., "A Cyclic Antimicrobial Peptide Produced in Primate Leukocytes by the Ligation of Two Truncated α-Defensins," *Science* 286:498-502, Oct. 1999. (6 pages).

Ton-That et al., "Purification and characterization of sortase, the transpeptidase that cleaves surface proteins of *Staphylococcus aureus* at the LPXTG motif," *PNAS* 96(22):12424-12429, Oct. 1999. (6 pages).

Trauger et al., "Peptide cyclization catalyzed by the thioesterase domain of tyrocidine synthetase," *Nature* 407:215-218, Sep. 2000. (6 pages).

Webb et al., "About MODELLER," retrieved from https://salilab.org/modeler/, on Jan. 25, 2017, 2 pages.

Wong et al., "Orally Active Peptidic Bradykinin B1 Receptor Antagonists Engineered from a Cyclotide Scaffold for Inflammatory Pain Treatment," *Angew. Chem. Int. Ed.* 51:5620-5624, Apr. 2012. (5 pages).

Wu et al., "Sortase A-Catalyzed Peptide Cyclization for the Synthesis of Macrocyclic Peptides and Glycopeptides," *Chem Commun (Camb).* 47(32):9218-9220, 2011 (Author Manuscript, available in PMC Aug. 28, 2012) (10 pages).

Xu et al., "In Vitro Protein Splicing of Purified Precursor and the Identification of a Branched Intermediate," *Cell* 75:1371-1377, Dec. 1993. (7 pages).

Xu et al., "Intein-Mediated Ligation and Cyclization of Expressed Proteins," *Methods* 24:257-277, Jul. 2001. (21 pages).

Yang et al., "asparaginyl endopeptidase [Vigna radiata]," Data Base NCBI Protein, [online], Accession No. AAK15049, Mar. 2, 2001, retrieved on Feb. 21, 2019 via Internet <URL: http://www.ncbi.nlm.nih.gov/protein/AAK15049.1>.

* cited by examiner

A    Reaction scheme

B    VyPAL2-mediated cyclization of GN14-SL

C    pH-dependent product yield

☐Hydrolysis  ■ Cyclization

A   Non-covalent immobilization via Lectin-glycan affinity binding
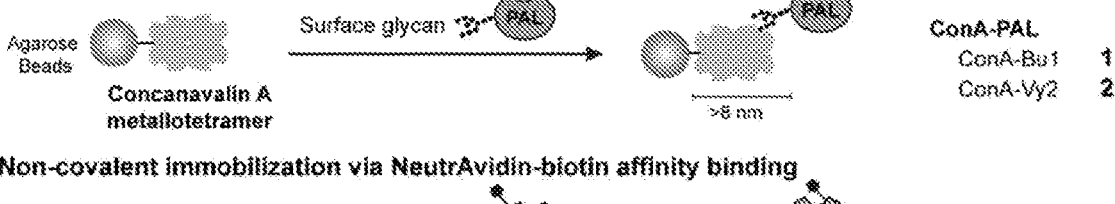
B   Non-covalent immobilization via NeutrAvidin-biotin affinity binding
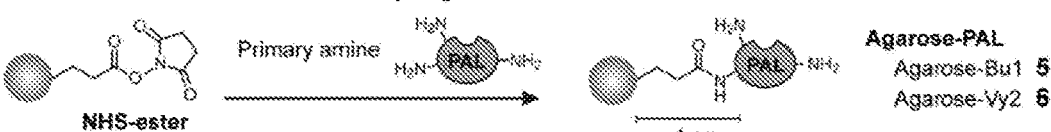
C   Covalent immobilization via direct coupling NHS-ester to amine of PALs
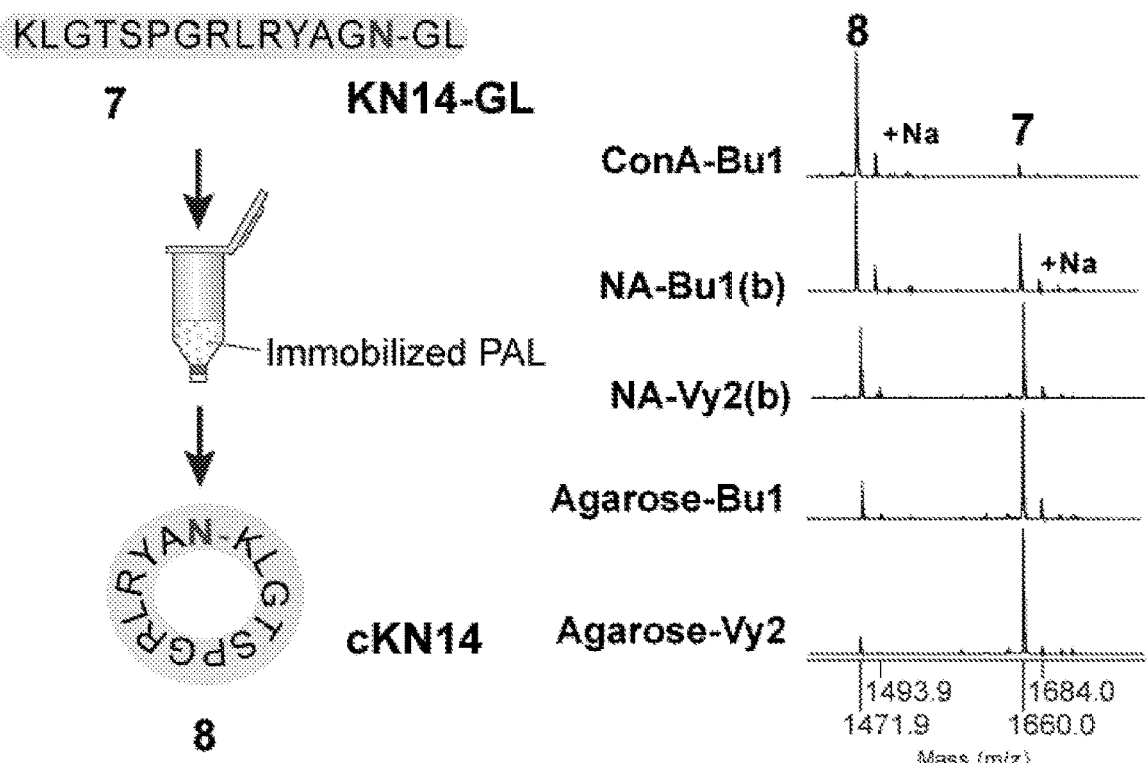
Fig. 7
Fig. 8

A     Cyclization of peptide with Pro at P2 position

12
Oxidized SFTI(D/N)-HV

13
SFTI(D/N)

B     Cyclization of naturally-cyclic protein

14
Folded AS-48K

15
Cyclic AS-48 c17
Cyclodimer c18
Cyclotrimer

A   Continuous-flow peptide ligation

B   Continuous-flow protein labeling

SEQUENCE LISTING

```
<160> NUMBER OF SEQ ID NOS: 88

<210> SEQ ID NO 1
<211> LENGTH: 269
<212> TYPE: PRT
<213> ORGANISM: Artificial
<220> FEATURE:
<223> OTHER INFORMATION: core domain of VyPAL2

<400> SEQUENCE: 1

Asp Ser Ile Gly Thr Arg Trp Ala Val Leu Ile Ala Gly Ser Lys Gly
1               5                   10                  15

Tyr His Asn Tyr Arg His Gln Ala Asp Val Cys His Met Tyr Gln Ile
            20                  25                  30

Leu Arg Lys Gly Gly Val Lys Asp Glu Asn Ile Ile Val Phe Met Tyr
        35                  40                  45

Asp Asp Ile Ala Tyr Asn Glu Ser Asn Pro Phe Pro Gly Ile Ile Ile
        50                  55                  60

Asn Lys Pro Gly Gly Glu Asn Val Tyr Lys Gly Val Pro Lys Asp Tyr
65                  70                  75                  80

Thr Gly Glu Asp Ile Asn Asn Val Asn Phe Leu Ala Ala Ile Leu Gly
                85                  90                  95

Asn Lys Ser Ala Ile Ile Gly Gly Ser Gly Lys Val Leu Asp Thr Ser
            100                 105                 110

Pro Asn Asp His Ile Phe Ile Tyr Tyr Ala Asp His Gly Ala Pro Gly
            115                 120                 125

Lys Ile Gly Met Pro Ser Lys Pro Tyr Leu Tyr Ala Asp Asp Leu Val
        130                 135                 140

Asp Thr Leu Lys Gln Lys Ala Ala Thr Gly Thr Tyr Lys Ser Met Val
145                 150                 155                 160

Phe Tyr Val Glu Ala Cys Asn Ala Gly Ser Met Phe Glu Gly Leu Leu
                165                 170                 175

Pro Glu Gly Thr Asn Ile Tyr Ala Met Ala Ala Ser Asn Ser Thr Glu
            180                 185                 190

Gly Ser Trp Ile Thr Tyr Cys Pro Gly Thr Pro Asp Phe Pro Pro Glu
            195                 200                 205

Phe Asp Val Cys Leu Gly Asp Leu Trp Ser Ile Thr Phe Leu Glu Asp
        210                 215                 220

Cys Asp Ala His Asn Leu Arg Thr Glu Thr Val His Gln Gln Phe Glu
225                 230                 235                 240

Leu Val Lys Lys Lys Ile Ala Tyr Ala Ser Thr Val Ser Gln Tyr Gly
            245                 250                 255
```

```
Asp Ile Pro Ile Ser Lys Asp Ser Leu Ser Val Tyr Met
            260                 265

<210> SEQ ID NO 2
<211> LENGTH: 332
<212> TYPE: PRT
<213> ORGANISM: Artificial
<220> FEATURE:
<223> OTHER INFORMATION: VyPAL2/1 chimeric protein

<400> SEQUENCE: 2

Met Gln Leu Phe Ala Ala Gly Val Ile Leu Phe Phe Leu Leu Ala Leu
1               5                   10                  15

Ser Gly Thr Ile Ala Gly Gly Leu Asp Val Asp Ser Leu Gln Leu Pro
            20                  25                  30

Ser Glu Ala Ala Lys Phe Phe His Asn Asp Asn Ser Thr Asn Asp Asp
        35                  40                  45

Asp Ser Ile Gly Thr Arg Trp Ala Val Leu Ile Ala Gly Ser Lys Gly
        50                  55                  60

Tyr His Asn Tyr Arg His Gln Ala Asp Val Cys His Met Tyr Gln Ile
65              70                  75                  80

Leu Arg Lys Gly Gly Val Lys Asp Glu Asn Ile Ile Val Phe Met Tyr
            85                  90                  95

Asp Asp Ile Ala Tyr Asn Glu Ser Asn Pro Phe Pro Gly Ile Ile Ile
            100                 105                 110

Asn Lys Pro Gly Gly Glu Asn Val Tyr Lys Gly Val Pro Lys Asp Tyr
            115                 120                 125

Thr Gly Glu Asp Ile Asn Asn Val Asn Phe Leu Ala Ala Ile Leu Gly
        130                 135                 140

Asn Lys Ser Ala Ile Ile Gly Gly Ser Gly Lys Val Leu Asp Thr Ser
145                 150                 155                 160

Pro Asn Asp His Ile Phe Ile Tyr Tyr Ala Asp His Gly Ala Pro Gly
                165                 170                 175

Lys Ile Gly Met Pro Ser Lys Pro Tyr Leu Tyr Ala Asp Asp Leu Val
                180                 185                 190

Asp Thr Leu Lys Gln Lys Ala Ala Thr Gly Thr Tyr Lys Ser Met Val
            195                 200                 205

Phe Tyr Val Glu Ala Cys Asn Ala Gly Ser Met Phe Glu Gly Leu Leu
            210                 215                 220

Pro Glu Gly Thr Asn Ile Tyr Ala Met Ala Ala Ser Asn Ser Thr Glu
225                 230                 235                 240

Gly Ser Trp Ile Thr Tyr Cys Pro Gly Thr Pro Asp Phe Pro Pro Glu
                245                 250                 255

Phe Asp Val Cys Leu Gly Asp Leu Trp Ser Ile Thr Phe Leu Glu Asp
            260                 265                 270

Cys Asp Ala His Asn Leu Arg Thr Glu Thr Val His Gln Gln Phe Glu
            275                 280                 285

Leu Val Lys Lys Lys Ile Ala Tyr Ala Ser Thr Val Ser Gln Tyr Gly
        290                 295                 300

Asp Ile Pro Ile Ser Lys Asp Ser Leu Ser Val Tyr Met Gly Thr Asp
305                 310                 315                 320

Pro Ala Asn Asp Asn Arg Thr Phe Val Asp Glu Asn
                325                 330

<210> SEQ ID NO 3
```

```
<211> LENGTH: 483
<212> TYPE: PRT
<213> ORGANISM: Artificial
<220> FEATURE:
<223> OTHER INFORMATION: VyPAL2/1 chimeric protein proenzyme

<400> SEQUENCE: 3

Met Gln Leu Phe Ala Ala Gly Val Ile Leu Phe Phe Leu Leu Ala Leu
1               5                   10                  15

Ser Gly Thr Ile Ala Gly Gly Leu Asp Val Asp Ser Leu Gln Leu Pro
            20                  25                  30

Ser Glu Ala Ala Lys Phe Phe His Asn Asp Asn Ser Thr Asn Asp Asp
        35                  40                  45

Asp Ser Ile Gly Thr Arg Trp Ala Val Leu Ile Ala Gly Ser Lys Gly
    50                  55                  60

Tyr His Asn Tyr Arg His Gln Ala Asp Val Cys His Met Tyr Gln Ile
65                  70                  75                  80

Leu Arg Lys Gly Gly Val Lys Asp Glu Asn Ile Ile Val Phe Met Tyr
                85                  90                  95

Asp Asp Ile Ala Tyr Asn Glu Ser Asn Pro Phe Pro Gly Ile Ile Ile
            100                 105                 110

Asn Lys Pro Gly Gly Glu Asn Val Tyr Lys Gly Val Pro Lys Asp Tyr
        115                 120                 125

Thr Gly Glu Asp Ile Asn Asn Val Asn Phe Leu Ala Ala Ile Leu Gly
    130                 135                 140

Asn Lys Ser Ala Ile Ile Gly Gly Ser Gly Lys Val Leu Asp Thr Ser
145                 150                 155                 160

Pro Asn Asp His Ile Phe Ile Tyr Tyr Ala Asp His Gly Ala Pro Gly
                165                 170                 175

Lys Ile Gly Met Pro Ser Lys Pro Tyr Leu Tyr Ala Asp Asp Leu Val
            180                 185                 190

Asp Thr Leu Lys Gln Lys Ala Ala Thr Gly Thr Tyr Lys Ser Met Val
        195                 200                 205

Phe Tyr Val Glu Ala Cys Asn Ala Gly Ser Met Phe Glu Gly Leu Leu
    210                 215                 220

Pro Glu Gly Thr Asn Ile Tyr Ala Met Ala Ala Ser Asn Ser Thr Glu
225                 230                 235                 240

Gly Ser Trp Ile Thr Tyr Cys Pro Gly Thr Pro Asp Phe Pro Pro Glu
                245                 250                 255

Phe Asp Val Cys Leu Gly Asp Leu Trp Ser Ile Thr Phe Leu Glu Asp
            260                 265                 270

Cys Asp Ala His Asn Leu Arg Thr Glu Thr Val His Gln Gln Phe Glu
        275                 280                 285

Leu Val Lys Lys Lys Ile Ala Tyr Ala Ser Thr Val Ser Gln Tyr Gly
    290                 295                 300

Asp Ile Pro Ile Ser Lys Asp Ser Leu Ser Val Tyr Met Gly Thr Asp
305                 310                 315                 320

Pro Ala Asn Asp Asn Arg Thr Phe Val Asp Glu Asn Ser Leu Arg Pro
                325                 330                 335

Pro Leu Lys Val Ile His Gln His Asp Ala Asp Leu Tyr His Ile Trp
            340                 345                 350

Cys Lys Tyr Asn Met Ala Pro Glu Gly Ser Ser Lys Lys Ile Glu Ala
        355                 360                 365

Gln Lys Gln Leu Leu Glu Leu Met Ser His Arg Ala His Val Asp Asn
    370                 375                 380
```

-continued

```
Ser Ile Thr Leu Ile Gly Lys Leu Leu Phe Gly Val Asn Lys Ala Ser
385                 390             395                 400

Lys Val Leu Asn Thr Val Arg Pro Val Gly Gln Pro Leu Val Asp Asp
                405             410                 415

Trp Gln Cys Leu Lys Ala Met Ile Arg Thr Phe Glu Thr His Cys Gly
            420             425             430

Ser Leu Ser Glu Tyr Gly Met Lys His Thr Leu Ser Phe Ala Asn Met
        435             440             445

Cys Asn Ala Gly Ile Gln Lys Glu Gln Leu Ala Glu Ala Ala Ala Gln
    450             455             460

Ala Cys Val Thr Phe Pro Ser Asn Pro Tyr Ser Ser Leu Ala Glu Gly
465             470             475             480

Phe Ser Ala
```

<210> SEQ ID NO 4
<211> LENGTH: 16
<212> TYPE: PRT
<213> ORGANISM: Artificial
<220> FEATURE:
<223> OTHER INFORMATION: Peptide substrate

<400> SEQUENCE: 4

```
Gly Ile Ser Thr Lys Ser Ile Pro Pro Ile Ser Tyr Arg Asn Ser Leu
1               5               10              15
```

<210> SEQ ID NO 5
<211> LENGTH: 484
<212> TYPE: PRT
<213> ORGANISM: Viola yedoensis

<400> SEQUENCE: 5

```
Met Gln Leu Phe Ala Ala Gly Val Ile Leu Phe Phe Leu Leu Ala Leu
1               5               10              15

Ser Gly Thr Ile Ala Gly Gly Leu Asp Val Asp Ser Leu Gln Leu Pro
                20              25              30

Ser Glu Ala Ala Lys Phe Phe His Asn Asp Asn Ser Thr Asn Asp Asp
        35              40              45

Asp Ser Ile Gly Thr Arg Trp Ala Val Leu Ile Ala Gly Ser Lys Gly
    50              55              60

Tyr His Asn Tyr Arg His Gln Ala Asp Val Cys His Met Tyr Gln Ile
65              70              75              80

Leu Arg Lys Gly Gly Val Lys Asp Glu Asn Ile Ile Val Phe Met Tyr
                85              90              95

Asp Asp Ile Ala Tyr Asn Glu Ser Asn Pro Phe Pro Gly Ile Ile Ile
            100             105             110

Asn Lys Pro Gly Gly Glu Asn Val Tyr Lys Gly Val Pro Lys Asp Tyr
        115             120             125

Thr Gly Glu Asp Ile Asn Asn Val Asn Phe Leu Ala Ala Ile Leu Gly
        130             135             140

Asn Lys Ser Ala Ile Ile Gly Gly Ser Gly Lys Val Leu Asp Thr Ser
145             150             155             160

Pro Asn Asp His Ile Phe Ile Tyr Tyr Ala Asp His Gly Ala Pro Gly
                165             170             175

Lys Ile Gly Met Pro Ser Lys Pro Tyr Leu Tyr Ala Asp Asp Leu Val
            180             185             190
```

-continued

```
Asp Thr Leu Lys Gln Lys Ala Ala Ala Gly Thr Tyr Lys Ser Met Val
        195                 200                 205

Phe Tyr Val Glu Ala Cys Asn Ala Gly Ser Met Phe Glu Gly Leu Leu
        210                 215                 220

Pro Glu Gly Met Asn Ile Tyr Ala Met Thr Ala Ser Asn Ser Thr Glu
225                 230                 235                 240

Gly Ser Leu Ile Ala Tyr Cys Ala Gly Val Thr Pro Gly Val Pro Leu
                245                 250                 255

Glu Ile Val Thr Cys Leu Gly Asp Leu Trp Ser Ile Thr Phe Leu Glu
                260                 265                 270

Asp Cys Asp Ala His Asn Leu Arg Thr Glu Thr Val His Gln Gln Phe
        275                 280                 285

Glu Leu Val Lys Lys Lys Ile Ala Tyr Ala Ser Thr Val Ser Gln Tyr
        290                 295                 300

Gly Asp Ile Pro Ile Ser Lys Asp Ser Leu Ser Val Tyr Met Gly Thr
305                 310                 315                 320

Asp Pro Ala Asn Asp Asn Arg Thr Phe Val Asp Glu Asn Ser Leu Arg
                325                 330                 335

Pro Pro Leu Lys Val Ile His Gln His Asp Ala Asp Leu Tyr His Ile
                340                 345                 350

Trp Cys Lys Tyr Asn Met Ala Pro Glu Gly Ser Ser Lys Lys Ile Glu
        355                 360                 365

Ala Gln Lys Gln Leu Leu Glu Leu Met Ser His Arg Ala His Val Asp
        370                 375                 380

Asn Ser Ile Thr Leu Ile Gly Lys Leu Leu Phe Gly Val Asn Lys Ala
385                 390                 395                 400

Ser Lys Val Leu Asn Thr Val Arg Pro Val Gly Gln Pro Leu Val Asp
                405                 410                 415

Asp Trp Gln Cys Leu Lys Ala Met Ile Arg Thr Phe Glu Thr His Cys
                420                 425                 430

Gly Ser Leu Ser Glu Tyr Gly Met Lys His Thr Leu Ser Phe Ala Asn
        435                 440                 445

Met Cys Asn Ala Gly Ile Gln Lys Glu Gln Leu Ala Glu Ala Ala Ala
        450                 455                 460

Gln Ala Cys Val Thr Phe Pro Ser Asn Pro Tyr Ser Ser Leu Ala Glu
465                 470                 475                 480

Gly Phe Ser Ala
```

<210> SEQ ID NO 6
<211> LENGTH: 483
<212> TYPE: PRT
<213> ORGANISM: Viola yedoensis

<400> SEQUENCE: 6

```
Met Gln Leu Phe Ala Ala Gly Val Ile Leu Phe Phe Leu Leu Ala Leu
1               5                   10                  15

Ser Gly Thr Ile Ala Gly Gly Leu Asp Val Asp Ser Leu Gln Leu Pro
                20                  25                  30

Ser Glu Ala Ala Lys Phe Phe His Asn Asp Asn Ser Thr Asn Asp Asp
        35                  40                  45

Asp Ser Ile Gly Thr Arg Trp Ala Val Leu Ile Ala Gly Ser Lys Gly
        50                  55                  60

Tyr His Asn Tyr Arg His Gln Ala Asp Val Cys His Met Tyr Gln Ile
65                  70                  75                  80
```

```
Leu Arg Lys Gly Gly Val Lys Asp Glu Asn Ile Ile Val Phe Met Tyr
            85              90                  95

Asp Asp Ile Ala Tyr Asn Glu Ser Asn Pro Phe Pro Gly Ile Ile Ile
            100             105             110

Asn Lys Pro Gly Gly Glu Asn Val Tyr Lys Gly Val Pro Lys Asp Tyr
            115             120             125

Thr Gly Glu Asp Ile Asn Asn Val Asn Phe Leu Ala Ala Ile Leu Gly
    130             135             140

Asn Lys Ser Ala Ile Ile Gly Gly Ser Gly Lys Val Leu Asp Thr Ser
145             150             155             160

Pro Asn Asp His Ile Phe Ile Tyr Tyr Ala Asp His Gly Ala Pro Gly
            165             170             175

Lys Ile Gly Met Pro Ser Lys Pro Tyr Leu Tyr Ala Asp Asp Leu Val
            180             185             190

Asp Thr Leu Lys Gln Lys Ala Ala Thr Gly Thr Tyr Lys Ser Met Val
            195             200             205

Phe Tyr Val Glu Ala Cys Asn Ala Gly Ser Met Phe Glu Gly Leu Leu
    210             215             220

Pro Glu Gly Thr Asn Ile Tyr Ala Met Ala Ala Ser Asn Ser Thr Glu
225             230             235             240

Gly Ser Trp Ile Thr Tyr Cys Pro Gly Thr Pro Asp Phe Pro Pro Glu
            245             250             255

Phe Asp Val Cys Leu Gly Asp Leu Trp Ser Ile Thr Phe Leu Glu Asp
            260             265             270

Cys Asp Ala His Asn Leu Arg Thr Glu Thr Val His Gln Gln Phe Glu
            275             280             285

Leu Val Lys Lys Lys Ile Ala Tyr Ala Ser Thr Val Ser Gln Tyr Gly
    290             295             300

Asp Ile Pro Ile Ser Lys Asp Ser Leu Ser Val Tyr Met Gly Thr Asp
305             310             315             320

Pro Ala Asn Asp Asn Arg Thr Phe Val Asp Glu Asn Ser Leu Arg Pro
            325             330             335

Pro Leu Lys Val Ile His Gln His Asp Ala Asp Leu Tyr His Ile Trp
            340             345             350

Cys Lys Tyr Asn Met Ala Pro Glu Gly Ser Ser Lys Lys Ile Glu Ala
            355             360             365

Gln Lys Gln Leu Leu Glu Leu Met Ser His Arg Ala His Val Asp Asn
    370             375             380

Ser Ile Thr Leu Ile Gly Lys Leu Leu Phe Gly Val Asn Lys Ala Ser
385             390             395             400

Lys Val Leu Asn Thr Val Arg Pro Val Gly Gln Pro Leu Val Asp Asp
            405             410             415

Trp Gln Cys Leu Lys Ala Met Ile Arg Thr Phe Glu Thr His Cys Gly
            420             425             430

Ser Leu Ser Glu Tyr Gly Met Lys His Thr Leu Ser Phe Ala Asn Met
            435             440             445

Cys Asn Ala Gly Ile Gln Lys Glu Gln Leu Ala Glu Ala Ala Ala Gln
    450             455             460

Ala Cys Val Thr Phe Pro Ser Asn Pro Tyr Ser Ser Leu Ala Glu Gly
465             470             475             480

Phe Ser Ala
```

-continued

```
<210> SEQ ID NO 7
<211> LENGTH: 487
<212> TYPE: PRT
<213> ORGANISM: Viola yedoensis

<400> SEQUENCE: 7

Met Gln Leu Phe Ala Ala Gly Val Ile Leu Phe Phe Leu Leu Ala Leu
1               5                   10                  15

Ser Gly Thr Ile Ala Gly Gly Leu Asp Val Asp Ser Leu Gln Leu Pro
            20                  25                  30

Ser Glu Ala Ala Lys Phe Phe His Asn Asp Asn Ser Thr Asn Asp Asp
        35                  40                  45

Asp Ser Ser Ala Gly Thr Lys Trp Ala Val Leu Ile Ala Gly Ser Lys
    50                  55                  60

Gly Tyr Gln Asn Tyr Arg His Gln Ala Asp Val Cys His Ala Tyr Gln
65                  70                  75                  80

Ile Leu Arg Arg Gly Gly Val Lys Asp Glu Asn Ile Ile Val Phe Met
                85                  90                  95

Tyr Asp Asp Ile Ala Tyr Asp Ile Arg Asn Pro Tyr Pro Gly Thr Ile
            100                 105                 110

Thr Asn Ser Pro Asp Lys Lys Asp Val Tyr Lys Gly Val Pro Lys Asp
        115                 120                 125

Tyr Thr Gly Glu Asp Val Asn Val Gln Asn Phe Leu Ala Val Ile Leu
    130                 135                 140

Gly Asn Lys Thr Ala Leu Thr Gly Gly Ser Gly Lys Val Leu Asp Thr
145                 150                 155                 160

Arg Pro Asn Asp His Ile Phe Ile Tyr Tyr Thr Asp His Gly Tyr Ala
                165                 170                 175

Gly Val Leu Gly Met Pro Thr Gln Pro Tyr Leu Tyr Ala Asn Asp Leu
            180                 185                 190

Ile Asp Thr Leu Lys Lys Lys His Ala Ser Gly Thr Tyr Glu Ser Leu
        195                 200                 205

Val Phe Tyr Val Glu Ala Cys Glu Ser Ala Ser Ile Phe Glu Gly Leu
    210                 215                 220

Leu Pro Asp Gly Leu Asn Ile Tyr Val Ser Thr Ala Ala Lys Ala Gly
225                 230                 235                 240

Glu Gly Ser Trp Val Val Tyr Cys Pro Thr Gln Gln Pro Pro Val Pro
                245                 250                 255

Ala Glu Tyr Gly Thr Cys Val Gly Asp Leu Tyr Ser Val Thr Trp Met
            260                 265                 270

Glu Asp Cys Asp Leu Tyr Asn Leu Arg Thr Gln Thr Leu His Gln Gln
        275                 280                 285

Tyr Glu Met Val Lys Lys Lys Ile Ala Tyr Ala Ser Thr Val Ser Gln
    290                 295                 300

Phe Gly Asp Leu Thr Ile Thr Lys Asp Ser Leu Phe Glu Tyr Met Gly
305                 310                 315                 320

Thr Asp Pro Ala Asn Glu Lys His His Tyr Glu Asp Gln Glu Asn Ser
            325                 330                 335

Leu Arg Pro His Val Asp Ala Val His Gln Arg Glu Ala Asp Leu Tyr
        340                 345                 350

His Phe Trp Asp Lys Tyr Gln Lys Ala Ser Glu Gly Ser Arg Asn Lys
    355                 360                 365

Val Ala Ala Arg Lys Gln Leu Val Glu Val Met Leu His Arg Met His
    370                 375                 380
```

-continued

```
Val Asp Asp Ser Ile Glu Ser Ile Ala Lys Leu Leu Phe Gly Ser Asp
385             390                 395                 400

Ala Lys Ala Ser Glu Met Met Asn Thr Ile Arg Pro Pro Gly Gln Pro
                405                 410                 415

Leu Val Ser Asp Trp Asp Cys Leu Lys Thr Met Val Arg Thr Phe Glu
                420                 425                 430

Thr His Cys Gly Ser Leu Ser Glu Tyr Gly Met Lys Tyr Thr Arg Phe
            435                 440                 445

Leu Ala Asn Met Cys Asn Ala Gly Ile Arg Lys Glu Gln Leu Ala Glu
        450                 455                 460

Ala Ala Ala Gln Ala Cys Val Thr Phe Pro Ser Asn Ser Tyr Ser Ser
465                 470                 475                 480

Leu Ala Glu Gly Phe Ser Ala
                485
```

<210> SEQ ID NO 8
<211> LENGTH: 488
<212> TYPE: PRT
<213> ORGANISM: Viola yedoensis

<400> SEQUENCE: 8

```
Met Lys Leu Leu Ala Ala Gly Val Ile Leu Val Ser Leu Leu Ala Leu
1               5                   10                  15

Ser Gly Thr Val Ala Val Ala Val Ala Gly Gly Leu Asp Val Asp Pro
                20                  25                  30

Leu Arg Leu Pro Ser Glu Ala Ala Lys Phe Phe His Asn Asp Asn Ser
            35                  40                  45

Thr Asn Asp Asp Asp Ser Ile Gly Thr Thr Trp Ala Val Leu Ile Ala
        50                  55                  60

Gly Ser Lys Gly Tyr His Asn Tyr Arg His Gln Ala Asp Val Cys His
65                  70                  75                  80

Met Tyr Gln Ile Leu Arg Lys Gly Gly Val Lys Asp Glu Asn Ile Ile
                85                  90                  95

Val Phe Met Tyr Asp Asp Ile Ala Tyr Asn Glu Ser Asn Pro Phe Pro
                100                 105                 110

Gly Ile Ile Ile Asn Lys Pro Gly Gly Glu Asn Val Tyr Lys Gly Val
            115                 120                 125

Pro Lys Asp Tyr Thr Gly Glu Asp Ile Asn Asn Val Asn Phe Leu Ala
        130                 135                 140

Ala Ile Leu Gly Asn Lys Ser Ala Ile Ile Gly Gly Ser Gly Lys Val
145                 150                 155                 160

Leu Asp Thr Ser Pro Asn Asp His Ile Phe Ile Tyr Tyr Ala Asp His
                165                 170                 175

Gly Ala Pro Gly Lys Ile Gly Met Pro Ser Lys Pro Tyr Leu Tyr Ala
            180                 185                 190

Asp Asp Leu Val Asp Thr Leu Lys Gln Lys Ala Ala Ala Gly Thr Tyr
            195                 200                 205

Lys Ser Met Val Phe Tyr Val Glu Ala Cys Asn Ala Gly Ser Met Phe
        210                 215                 220

Glu Gly Leu Leu Pro Glu Gly Met Asn Ile Tyr Ala Met Thr Ala Ser
225                 230                 235                 240

Asn Ser Thr Glu Gly Ser Leu Ile Ala Tyr Cys Ala Gly Val Thr Pro
                245                 250                 255

Gly Val Pro Leu Glu Ile Val Thr Cys Leu Gly Asp Leu Trp Ser Ile
            260                 265                 270
```

```
Thr Phe Leu Glu Asp Cys Asp Ala His Asn Leu Arg Thr Glu Thr Val
        275             280             285

His Gln Gln Phe Glu Leu Val Lys Lys Lys Ile Ala Tyr Ala Ser Thr
    290             295             300

Val Ser Gln Tyr Gly Asp Ile Pro Ile Ser Lys Asp Ser Leu Ser Val
305             310             315             320

Tyr Met Gly Thr Asp Pro Ala Asn Asp Asn Arg Thr Phe Val Asp Glu
                325             330             335

Asn Ser Leu Arg Pro Pro Leu Lys Val Ile His Gln Arg Asp Ala Tyr
            340             345             350

Leu Tyr His Leu Trp Tyr Lys Tyr Gln Asn Thr Pro Glu Gly Ser Ser
        355             360             365

Lys Lys Ile Glu Ala Gln Lys Gln Leu Leu Glu Met Met Ser His Arg
    370             375             380

Ala His Val Asp Asn Ser Ile Thr Leu Ile Gly Lys Leu Leu Phe Gly
385             390             395             400

Met Asp Lys Ala Ser Lys Met Leu Asn Ser Val Arg Pro Ala Gly Gln
                405             410             415

Pro Leu Val Asp Asp Trp Gln Cys Leu Lys Thr Met Ile Arg Thr Phe
                420             425             430

Glu Arg His Cys Gly Ser Leu Ser Glu Tyr Gly Met Lys His Thr Leu
            435             440             445

Ser Phe Ala Asn Met Cys Asn Ala Gly Ile Arg Lys Glu Gln Leu Ala
        450             455             460

Glu Ala Ala Ala Gln Ala Cys Val Thr Phe Pro Ser Asn Ser Tyr Ser
465             470             475             480

Ser Leu Ala Glu Gly Phe Ser Ala
                485
```

```
<210> SEQ ID NO 9
<211> LENGTH: 487
<212> TYPE: PRT
<213> ORGANISM: Viola yedoensis

<400> SEQUENCE: 9

Met Lys Leu Leu Ala Ala Gly Val Ile Leu Val Ser Leu Leu Ala Leu
1               5               10              15

Ser Gly Thr Val Ala Val Ala Val Ala Gly Gly Leu Asp Val Asp Pro
            20              25              30

Leu Arg Leu Pro Ser Glu Ala Ala Lys Phe Phe His Asn Asp Asn Ser
        35              40              45

Thr Asn Asp Asp Asp Ser Ile Gly Thr Thr Trp Ala Val Leu Ile Ala
    50              55              60

Gly Ser Lys Gly Tyr His Asn Tyr Arg His Gln Ala Asp Val Cys His
65              70              75              80

Met Tyr Gln Ile Leu Arg Lys Gly Gly Val Lys Asp Glu Asn Ile Ile
                85              90              95

Val Phe Met Tyr Asp Asp Ile Ala Tyr Asn Glu Ser Asn Pro Phe Pro
                100             105             110

Gly Ile Ile Ile Asn Lys Pro Gly Gly Glu Asn Val Tyr Lys Gly Val
        115             120             125

Pro Lys Asp Tyr Thr Gly Glu Asp Ile Asn Asn Val Asn Phe Leu Ala
        130             135             140
```

-continued

```
Ala Ile Leu Gly Asn Lys Ser Ala Ile Ile Gly Gly Ser Gly Lys Val
145                 150                 155                 160

Leu Asp Thr Ser Pro Asn Asp His Ile Phe Ile Tyr Tyr Ala Asp His
                165                 170                 175

Gly Ala Pro Gly Lys Ile Gly Met Pro Ser Lys Pro Tyr Leu Tyr Ala
                180                 185                 190

Asp Asp Leu Val Asp Thr Leu Lys Gln Lys Ala Ala Thr Gly Thr Tyr
                195                 200                 205

Lys Ser Met Val Phe Tyr Val Glu Ala Cys Asn Ala Gly Ser Met Phe
        210                 215                 220

Glu Gly Leu Leu Pro Glu Gly Thr Asn Ile Tyr Ala Met Ala Ala Ser
225                 230                 235                 240

Asn Ser Thr Glu Gly Ser Trp Ile Thr Tyr Cys Pro Gly Thr Pro Asp
                245                 250                 255

Phe Pro Pro Glu Phe Asp Val Cys Leu Gly Asp Leu Trp Ser Ile Thr
                260                 265                 270

Phe Leu Glu Asp Cys Asp Ala His Asn Leu Arg Thr Glu Thr Val His
        275                 280                 285

Gln Gln Phe Glu Leu Val Lys Lys Lys Ile Ala Tyr Ala Ser Thr Val
        290                 295                 300

Ser Gln Tyr Gly Asp Ile Pro Ile Ser Lys Asp Ser Leu Ser Val Tyr
305                 310                 315                 320

Met Gly Thr Asp Pro Ala Asn Asp Asn Arg Thr Phe Val Asp Glu Asn
                325                 330                 335

Ser Leu Arg Pro Pro Leu Lys Val Ile His Gln Arg Asp Ala Tyr Leu
                340                 345                 350

Tyr His Leu Trp Tyr Lys Tyr Gln Asn Thr Pro Glu Gly Ser Ser Lys
        355                 360                 365

Lys Ile Glu Ala Gln Lys Gln Leu Leu Glu Met Met Ser His Arg Ala
        370                 375                 380

His Val Asp Asn Ser Ile Thr Leu Ile Gly Lys Leu Leu Phe Gly Met
385                 390                 395                 400

Asp Lys Ala Ser Lys Met Leu Asn Ser Val Arg Pro Ala Gly Gln Pro
                405                 410                 415

Leu Val Asp Asp Trp Gln Cys Leu Lys Thr Met Ile Arg Thr Phe Glu
                420                 425                 430

Arg His Cys Gly Ser Leu Ser Glu Tyr Gly Met Lys His Thr Leu Ser
        435                 440                 445

Phe Ala Asn Met Cys Asn Ala Gly Ile Arg Lys Glu Gln Leu Ala Glu
        450                 455                 460

Ala Ala Ala Gln Ala Cys Val Thr Phe Pro Ser Asn Ser Tyr Ser Ser
465                 470                 475                 480

Leu Ala Glu Gly Phe Ser Ala
                485
```

```
<210> SEQ ID NO 10
<211> LENGTH: 493
<212> TYPE: PRT
<213> ORGANISM: Viola yedoensis

<400> SEQUENCE: 10

Met Glu Ala Tyr Arg Ser Phe Phe Asn Tyr Val Ile Phe Phe Ser Val
1               5                   10                  15
```

-continued

```
Val Leu Cys Leu Phe Gly Ala Gln Ala Thr Arg Val Ser Arg Pro Phe
         20                  25                  30

Val Pro Gly Ile Leu Met Pro Thr Asp Arg Val Gly Thr Glu Pro Asp
         35                  40                  45

Gln Ala Asp Asp Val Asp Gly Asp Glu Ile Gly Thr Arg Trp Ala Val
    50                  55                  60

Leu Val Ala Gly Ser Asn Gly Phe Gly Asn Tyr Arg His Gln Ala Asp
65                  70                  75                  80

Val Cys His Ala Tyr Gln Leu Leu Arg Lys Gly Gly Leu Lys Glu Glu
                85                  90                  95

Asn Ile Val Val Phe Met Tyr Asp Asp Ile Ala Thr Asn Gln Leu Asn
             100                 105                 110

Pro Arg Pro Gly Ile Ile Ile Asn His Pro Gln Gly Glu Asp Val Tyr
             115                 120                 125

His Gly Val Pro Lys Asp Tyr Thr Gly Ala Glu Val Asn Ala His Asn
    130                 135                 140

Leu Tyr Ala Val Leu Leu Gly Asp Lys Ser Ala Val Lys Gly Gly Ser
145                 150                 155                 160

Gly Lys Val Val Asn Ser Lys Pro Asp Asp Arg Ile Phe Val Tyr Tyr
                165                 170                 175

Ser Asp His Gly Gly Pro Gly Val Leu Gly Met Pro Asn Leu Pro Tyr
             180                 185                 190

Val Tyr Ala Met Asp Phe Ile Asp Thr Leu Lys Lys Lys His Ala Ala
         195                 200                 205

Asn Ser Tyr Arg Glu Met Val Val Tyr Val Glu Ala Cys Glu Ser Gly
    210                 215                 220

Ser Leu Phe Glu Gly Val Met Pro Lys Asp Leu Asn Ile Tyr Val Thr
225                 230                 235                 240

Thr Ala Ser Asn Ala Gln Glu Asn Ser Trp Gly Thr Tyr Cys Pro Gly
             245                 250                 255

Glu Gly Ala Pro Pro Glu Tyr Asn Thr Cys Leu Gly Asp Leu Tyr Ser
             260                 265                 270

Val Ala Trp Met Glu Asp Ser Glu Ser His Asn Leu Lys Lys Glu Ala
         275                 280                 285

Ile Lys Asp Gln Tyr Lys Thr Val Lys Ala Arg Thr Ser Asp Ser Ser
    290                 295                 300

Thr Tyr His Ser Gly Ser His Val Met Glu Tyr Gly Asn Arg Ser Ile
305                 310                 315                 320

Arg Ala Glu Lys Leu Tyr Leu Tyr Gln Gly Phe Asp Pro Ala Thr Val
             325                 330                 335

Asn Phe Pro Pro Asn Asn Gly Leu Leu Lys Pro Met Glu Val Val Asn
             340                 345                 350

Gln Arg Asp Ala Glu Leu Val Phe Met Trp Gln Met Tyr Lys Lys Ser
         355                 360                 365

Glu Glu Gly Ser Glu Glu Lys Thr Glu Ile Leu Asn Leu Ile Lys Glu
    370                 375                 380

Thr Met Arg His Arg Asn His Leu Asp Gly Ser Ile Lys Leu Ile Gly
385                 390                 395                 400

Thr Leu Leu Phe Gly Pro Lys Glu Gly Ser Ser Val Leu Gln Ser Val
             405                 410                 415

Arg Lys Pro Gly Ser Pro Leu Val Asp Asp Trp Lys Cys Leu Lys Ser
         420                 425                 430
```

-continued

```
Met Val Arg Ser Phe Glu Arg His Cys Gly Ser Leu Thr Gln Tyr Gly
        435             440             445

Met Lys His Met Arg Ala Phe Ala Asn Ile Cys Asn Ser Gly Ile Pro
        450             455             460

Arg Ala Ser Met Glu Glu Ala Cys Gly Val Ala Cys Ser Gly His Asp
465             470             475             480

Val Gly Glu Trp Asn Pro Phe Ile Arg Gly Tyr Ser Ala
                485             490

<210> SEQ ID NO 11
<211> LENGTH: 493
<212> TYPE: PRT
<213> ORGANISM: Viola yedoensis

<400> SEQUENCE: 11

Met Glu Ala Tyr Arg Ser Phe Phe Asn Tyr Val Ile Phe Phe Ser Val
1               5               10              15

Val Leu Cys Leu Phe Gly Ala Gln Ala Thr Arg Val Ser Arg Pro Phe
        20              25              30

Val Pro Gly Ile Leu Met Pro Thr Asp Arg Val Gly Thr Glu Pro Asp
        35              40              45

Gln Ala Asp Asp Val Asp Gly Asp Glu Ile Gly Thr Arg Trp Ala Val
        50              55              60

Leu Val Ala Gly Ser Asn Gly Phe Gly Asn Tyr Arg His Gln Ala Asp
65              70              75              80

Val Cys His Ala Tyr Gln Leu Leu Arg Lys Gly Gly Leu Lys Glu Glu
                85              90              95

Asn Ile Val Val Phe Met Tyr Asp Asp Ile Ala Thr Asn Gln Leu Asn
                100             105             110

Pro Arg Pro Gly Ile Ile Ile Asn His Pro Gln Gly Glu Asp Val Tyr
        115             120             125

His Gly Val Pro Lys Asp Tyr Thr Gly Ala Glu Val Asn Ala His Asn
        130             135             140

Leu Tyr Ala Val Leu Leu Gly Asp Lys Ser Ala Val Lys Gly Gly Ser
145             150             155             160

Gly Lys Val Val Asn Ser Lys Pro Asp Asp Arg Ile Phe Val Tyr Tyr
                165             170             175

Ser Asp His Gly Gly Pro Gly Val Leu Gly Met Pro Asn Leu Pro Tyr
        180             185             190

Val Tyr Ala Met Asp Phe Ile Asp Thr Leu Lys Lys Lys His Ala Ala
        195             200             205

Asn Ser Tyr Arg Glu Met Val Val Tyr Val Glu Ala Cys Glu Ser Gly
        210             215             220

Ser Asn Phe Glu Gly Val Met Pro Glu Asp Leu Asn Ile Tyr Val Thr
225             230             235             240

Thr Ala Ser Asn Ala Gln Glu Asn Ser Trp Gly Thr Tyr Cys Pro Gly
                245             250             255

Glu Gly Ala Pro Pro Glu Tyr Asn Thr Cys Leu Gly Asp Leu Tyr Ser
                260             265             270

Val Ala Trp Met Glu Asp Ser Glu Ser His Asn Leu Lys Lys Glu Ala
        275             280             285

Ile Lys Asp Gln Tyr Lys Thr Val Lys Ala Arg Thr Ser Asp Ser Ser
        290             295             300

Thr Tyr His Ser Gly Ser His Val Met Glu Tyr Gly Asn Arg Ser Ile
305             310             315             320
```

```
Arg Gly Glu Lys Leu Tyr Leu Tyr Gln Gly Phe Asp Pro Ala Thr Val
            325             330             335

Asn Phe Pro Pro Asn Asn Gly Leu Pro Lys Pro Met Glu Val Val Asn
            340             345             350

Gln Arg Asp Ala Glu Leu Val Phe Met Trp Gln Met Tyr Lys Lys Ser
            355             360             365

Lys Glu Gly Ser Glu Glu Lys Thr Glu Ile Leu Asn Gln Ile Lys Glu
            370             375             380

Thr Met Arg His Arg Asn His Leu Asp Gly Ser Ile Lys Leu Ile Gly
385             390             395             400

Thr Leu Leu Phe Gly Pro Lys Lys Gly Ser Ser Ile Leu Gln Ser Val
            405             410             415

Arg Thr Pro Gly Ser Pro Leu Val Asp Asp Trp Lys Cys Leu Lys Ser
            420             425             430

Met Val Arg Ser Phe Glu Arg His Cys Gly Ser Leu Thr Gln Tyr Gly
            435             440             445

Met Lys His Met Arg Ala Phe Ala Asn Ile Cys Asn Tyr Gly Ile Ser
            450             455             460

Gln Ala Ser Met Glu Glu Ala Cys Gly Val Ala Cys Gly Gly His Asp
465             470             475             480

Val Gly Glu Ser His Pro Phe Ile Arg Gly Tyr Ser Ala
                485             490
```

```
<210> SEQ ID NO 12
<211> LENGTH: 499
<212> TYPE: PRT
<213> ORGANISM: Viola yedoensis

<400> SEQUENCE: 12

Met Thr Arg Val Ala Thr Gly Ala Ile Leu Leu Phe Met Val Ala Leu
1               5               10              15

Ala Gly Ile Glu Ala Gly Arg Gln Asp Ile Asp His Asp Val Leu Arg
            20              25              30

Leu Pro Thr Glu Val Ser Asn Phe Phe Arg Asn Asn Asn Asn Asn Lys
            35              40              45

Asn Lys Asn Asp Lys Asn Asp Asn Gly Val Asp Ser Thr Gly Thr Arg
            50              55              60

Trp Ala Val Leu Ile Ala Gly Ser Asn Gly Tyr Trp Asn Tyr Arg His
65              70              75              80

Gln Ala Asp Val Cys His Ala Tyr Gln Ile Leu Lys Lys Gly Gly Leu
            85              90              95

Lys Asp Glu Asn Ile Ile Val Phe Met Tyr Asp Asp Ile Ala Asn Asp
            100             105             110

Ile Glu Asn Pro Arg Pro Gly Ile Ile Ile Asn Asn Pro Lys Gly Glu
            115             120             125

Asp Val Tyr Lys Gly Val Pro Lys Asp Tyr Thr Gly Glu Gln Val Thr
            130             135             140

Ala Gly Asn Phe Phe Asn Val Ile Leu Gly Asn Lys Thr Gly Leu Thr
145             150             155             160

Gly Gly Ser Gly Lys Val Val Asn Ser Gly Pro Asn Asp His Ile Phe
            165             170             175

Ile Tyr Tyr Thr Asp His Gly Gly Pro Gly Ile Leu Gly Met Pro Thr
            180             185             190
```

-continued

```
Ser Pro Tyr Ile Tyr Ala Asp Asp Leu Val Asp Val Leu Lys Lys Lys
        195                 200                 205

His Ala Ser Gly Thr Tyr Lys Ser Leu Val Phe Tyr Val Glu Ala Cys
    210                 215                 220

Glu Ser Gly Ser Ile Phe Glu Gly Ile Leu Pro Lys Gly Leu Asn Ile
225                 230                 235                 240

Tyr Ala Thr Thr Ala Ser Asn Ala Val Glu Ser Ser Trp Gly Thr Tyr
                245                 250                 255

Cys Pro Gly Glu Asn Pro Gly Pro Pro Glu Glu Tyr Asp Thr Cys Leu
                260                 265                 270

Gly Asp Leu Tyr Ser Val Ala Trp Met Glu Asp Ser Asp Val His Asn
            275                 280                 285

Leu Gln Thr Glu Thr Leu His Gln Gln Tyr Gln Leu Val Lys Asp Arg
        290                 295                 300

Thr Gly Lys Arg Asn Asn Gly Tyr Gly Ser His Val Met Gln Tyr Gly
305                 310                 315                 320

Asp Val Pro Leu Ser Lys Asp Ser Leu Phe Val Tyr Met Gly Thr Asn
                325                 330                 335

Pro Ala Asn Asp Asn Tyr Thr Phe Met Asp Asn Asn Ala Leu Arg Gln
                340                 345                 350

Pro Ser Lys Ala Val Asn Gln Arg Asp Ala Asp Leu Leu His Phe Trp
            355                 360                 365

His Lys Tyr Arg Lys Ala Pro Glu Gly Ser Pro Arg Lys Met Glu Ala
    370                 375                 380

Gln Lys Gln Phe Val Glu Met Met Ser His Arg Leu His Leu Asp Gln
385                 390                 395                 400

Ser Ile Lys Phe Ile Gly Arg Leu Leu Phe Gly Ile Asp Lys Ala Ser
                405                 410                 415

Glu Val Leu Ser Thr Val Arg Pro Ala Gly Gln Pro Leu Val Asp Asp
            420                 425                 430

Trp Asp Cys Leu Lys Thr Leu Val Arg Thr Phe Glu Thr His Cys Gly
            435                 440                 445

Ser Leu Ser Gln Tyr Gly Met Lys His Met Arg Ser Leu Ala Asn Leu
    450                 455                 460

Cys Asn Ala Gly Ile Arg Lys Glu Lys Met Ala Glu Ala Ser Val Gln
465                 470                 475                 480

Ala Cys Ala Thr Val Pro Ser Asn Pro Trp Ser Ser Leu Lys Lys Gly
                485                 490                 495

Phe Ser Ala
```

```
<210> SEQ ID NO 13
<211> LENGTH: 498
<212> TYPE: PRT
<213> ORGANISM: Viola yedoensis

<400> SEQUENCE: 13
```

```
Met Thr Arg Leu Ala Ser Gly Ala Ile Leu Leu Phe Leu Phe Ala Val
1               5                   10                  15

Ala Gly Ile Glu Ala Gly Arg Gln Asp Ile Asp Asp Val Leu Arg Leu
            20                  25                  30

Pro Thr Glu Val Ser Asn Phe Phe Arg Asn Asn Asn Asn Lys Asn
        35                  40                  45

Asn Asn Asp Lys Asn Ala Asn Gly Asp Asp Ser Thr Gly Thr Arg Trp
    50                  55                  60
```

-continued

```
Ala Val Leu Ile Ala Gly Ser Asn Gly Tyr Trp Asn Tyr Arg His Gln
65                  70                  75                  80

Ala Asp Val Cys His Ala Tyr Gln Ile Leu Lys Lys Gly Gly Leu Lys
                85                  90                  95

Asp Glu Asn Ile Ile Val Phe Met Tyr Asp Asp Ile Ala Asn Asp Ile
            100                 105                 110

Glu Asn Pro Arg Pro Gly Ile Ile Ile Asn Asn Pro Lys Gly Glu Asp
        115                 120                 125

Val Tyr Ile Gly Val Pro Lys Asp Tyr Thr Gly Glu Gln Val Thr Ala
    130                 135                 140

Gly Asn Phe Tyr Asn Val Ile Leu Gly Asn Lys Thr Gly Leu Thr Gly
145                 150                 155                 160

Gly Ser Gly Lys Val Val Asn Ser Gly Pro Asn Asp His Ile Phe Ile
                165                 170                 175

Tyr Tyr Thr Asp His Gly Gly Pro Gly Ile Leu Gly Met Pro Thr Ser
            180                 185                 190

Pro Tyr Ile Tyr Ala Asp Asp Leu Val Asp Val Leu Lys Lys Lys His
        195                 200                 205

Ala Ser Gly Thr Tyr Lys Ser Leu Val Phe Tyr Val Glu Ala Cys Glu
    210                 215                 220

Ser Gly Ser Ile Phe Glu Gly Ile Leu Pro Lys Gly Leu Asn Ile Tyr
225                 230                 235                 240

Ala Thr Thr Ala Ser Asn Ala Val Glu Ser Ser Trp Gly Thr Tyr Cys
                245                 250                 255

Pro Gly Glu His Pro Ser Pro Pro Gln Glu Tyr Asp Thr Cys Leu Gly
            260                 265                 270

Asp Leu Tyr Ser Val Ala Trp Met Glu Asp Ser Asp Val His Asn Leu
        275                 280                 285

Gln Thr Glu Thr Leu His Gln Gln Tyr Gln Leu Val Lys Asp Arg Thr
    290                 295                 300

Gly Asn Gly Tyr Asn Gly Tyr Gly Ser His Val Met Gln Tyr Gly Asp
305                 310                 315                 320

Val Pro Leu Ser Lys Asp Asn Leu Phe Glu Tyr Met Gly Thr Asn Pro
                325                 330                 335

Ala Asn Asp Asn Tyr Thr Phe Met Asp Asp Asn Ala Leu Arg Gln Pro
            340                 345                 350

Ser Lys Ala Val Asn Gln Arg Asp Ala Asp Leu Leu His Phe Trp His
        355                 360                 365

Lys Tyr Arg Lys Ala Pro Glu Gly Ser Pro Arg Lys Met Glu Ala Gln
    370                 375                 380

Lys Gln Phe Ile Glu Met Met Thr His Arg Leu His Leu Asp Gln Ser
385                 390                 395                 400

Ile Lys Phe Ile Gly Arg Leu Leu Phe Gly Ile Asp Lys Ala Ser Glu
                405                 410                 415

Val Leu Ser Thr Val Arg Pro Ala Gly Gln Pro Leu Val Asp Asp Trp
            420                 425                 430

Asn Cys Leu Lys Thr Leu Val Arg Thr Phe Glu Thr His Cys Gly Ser
        435                 440                 445

Leu Ser Gln Tyr Gly Met Lys His Met Arg Ser Leu Ala Asn Leu Cys
    450                 455                 460

Asn Ala Gly Ile Arg Lys Glu Lys Met Ala Glu Ala Ser Ala Gln Ala
465                 470                 475                 480
```

-continued

```
Cys Ala Thr Val Pro Ser Asn Pro Trp Ser Ser Leu Lys Lys Gly Phe
            485                 490                 495

Ser Ala

<210> SEQ ID NO 14
<211> LENGTH: 467
<212> TYPE: PRT
<213> ORGANISM: Viola canadensis

<400> SEQUENCE: 14

Met Ala Thr Leu Val Leu Leu Phe Leu Leu Ala Phe Ser Gly Phe Ala
1               5                   10                  15

Ala Gly Gly Arg Asp Ile Thr Gly Asp Gly Phe Leu Arg Leu Pro Ser
            20                  25                  30

His Gly Asn Gly Asn Ser Gly Asp Val Asp Ser Lys Ala Gly Thr Lys
        35                  40                  45

Trp Ala Val Leu Ile Ala Gly Ser Lys Gly Tyr Gln Asn Tyr Arg His
    50                  55                  60

Gln Ala Asp Val Cys His Ala Tyr Gln Ile Leu Arg Lys Gly Gly Val
65                  70                  75                  80

Lys Asp Glu Asn Ile Ile Val Phe Met Tyr Asp Asp Ile Ala Tyr Asp
                85                  90                  95

Ile Arg Asn Pro Tyr Pro Gly Thr Ile Ile Asn Ser Pro Asp Lys Lys
                100                 105                 110

Asp Val Tyr Lys Gly Val Pro Lys Asp Tyr Thr Gly Glu Asp Val Asn
            115                 120                 125

Val Gln Asn Phe Leu Ala Val Ile Leu Gly Asn Lys Thr Ala Leu Thr
        130                 135                 140

Gly Gly Ser Gly Lys Val Leu Asp Thr Arg Pro Asn Asp His Ile Phe
145                 150                 155                 160

Ile Tyr Tyr Thr Asp His Gly Tyr Pro Gly Val Leu Gly Met Pro Thr
                165                 170                 175

Glu Pro Tyr Leu Tyr Ala Asn Asp Leu Ile Asp Thr Leu Lys Lys Lys
                180                 185                 190

His Ala Leu Gly Thr Tyr Glu Gly Leu Val Phe Tyr Val Glu Ala Cys
            195                 200                 205

Glu Ser Ala Ser Ile Phe Glu Gly Leu Leu Pro Asp Gly Leu Asn Ile
        210                 215                 220

Tyr Val Ser Thr Ala Ala Lys Ala Gly Glu Gly Ser Trp Val Ala Tyr
225                 230                 235                 240

Cys Pro Ser Gln Glu Pro Pro Val Pro Ala Glu Tyr Gly Thr Cys Val
                245                 250                 255

Gly Asp Leu Tyr Ser Val Thr Trp Met Glu Asp Ser Asp Val Tyr Asn
            260                 265                 270

Leu Arg Thr Gln Thr Leu His Gln Gln Tyr Glu Leu Val Lys Asn Lys
        275                 280                 285

Ile Ala Tyr Ala Ser Thr Val Ser Gln Phe Gly Asp Phe Pro Ile Ser
    290                 295                 300

Lys Asp Ser Leu Phe Glu Tyr Met Gly Thr Asp Pro Ala Asn Glu Lys
305                 310                 315                 320

Arg Gln Tyr Glu Asp Glu Glu Lys Ser Ser Ser Pro His Val Gly Ala
                325                 330                 335

Val His Gln Arg Glu Ala Asp Leu His His Phe Trp Asp Lys Tyr Gln
            340                 345                 350
```

-continued

```
Lys Ala Ser Glu Gly Ser Arg Asn Lys Val Asp Ala Arg Lys Gln Leu
        355                 360                 365

Val Glu Val Met Leu His Arg Met His Val Asp Asp Ser Ile Glu Ser
    370                 375                 380

Ile Ala Lys Leu Leu Phe Gly Ser Gly Ala Lys Ala Ser Glu Met Met
385                 390                 395                 400

Asn Thr Ile Arg Pro Pro Gly Gln Pro Leu Val Ser Asp Trp Asp Cys
                405                 410                 415

Leu Lys Thr Met Val Arg Thr Phe Glu Thr His Cys Gly Ser Leu Ser
                420                 425                 430

Glu Tyr Gly Met Lys Tyr Thr Arg Phe Leu Ala Asn Ile Cys Asn Ser
        435                 440                 445

Gly Ile Gln Lys Glu Lys Met Gly Glu Ala Ser Ala Gln Val Cys Leu
    450                 455                 460

Asn Phe Pro
465

<210> SEQ ID NO 15
<211> LENGTH: 6
<212> TYPE: PRT
<213> ORGANISM: Artificial
<220> FEATURE:
<223> OTHER INFORMATION: MLA motif

<400> SEQUENCE: 15

Lys Lys Ile Ala Tyr Ala
1               5

<210> SEQ ID NO 16
<211> LENGTH: 6
<212> TYPE: PRT
<213> ORGANISM: Artificial
<220> FEATURE:
<223> OTHER INFORMATION: MLA motif

<400> SEQUENCE: 16

Asn Lys Ile Ala Tyr Ala
1               5

<210> SEQ ID NO 17
<211> LENGTH: 166
<212> TYPE: PRT
<213> ORGANISM: Artificial
<220> FEATURE:
<223> OTHER INFORMATION: VyPAL1 cap sequence

<400> SEQUENCE: 17

Gly Thr Asp Pro Ala Asn Asp Asn Arg Thr Phe Val Asp Glu Asn Ser
1               5                   10                  15

Leu Arg Pro Pro Leu Lys Val Ile His Gln His Asp Ala Asp Leu Tyr
        20                  25                  30

His Ile Trp Cys Lys Tyr Asn Met Ala Pro Glu Gly Ser Ser Lys Lys
        35                  40                  45

Ile Glu Ala Gln Lys Gln Leu Leu Glu Leu Met Ser His Arg Ala His
    50                  55                  60

Val Asp Asn Ser Ile Thr Leu Ile Gly Lys Leu Leu Phe Gly Val Asn
65                  70                  75                  80

Lys Ala Ser Lys Val Leu Asn Thr Val Arg Pro Val Gly Gln Pro Leu
                85                  90                  95
```

-continued

```
Val Asp Asp Trp Gln Cys Leu Lys Ala Met Ile Arg Thr Phe Glu Thr
            100                 105                 110

His Cys Gly Ser Leu Ser Glu Tyr Gly Met Lys His Thr Leu Ser Phe
            115                 120                 125

Ala Asn Met Cys Asn Ala Gly Ile Gln Lys Glu Gln Leu Ala Glu Ala
            130                 135                 140

Ala Ala Gln Ala Cys Val Thr Phe Pro Ser Asn Pro Tyr Ser Ser Leu
145                 150                 155                 160

Ala Glu Gly Phe Ser Ala
                165

<210> SEQ ID NO 18
<211> LENGTH: 281
<212> TYPE: PRT
<213> ORGANISM: Artificial
<220> FEATURE:
<223> OTHER INFORMATION: active fragment of Clitoria ternatea butelase-1

<400> SEQUENCE: 18

Val Glu Gly Thr Arg Trp Ala Val Leu Val Ala Gly Ser Lys Gly Tyr
1               5                   10                  15

Val Asn Tyr Arg His Gln Ala Asp Val Cys His Ala Tyr Gln Ile Leu
            20                  25                  30

Lys Lys Gly Gly Leu Lys Asp Glu Asn Ile Ile Val Phe Met Tyr Asp
            35                  40                  45

Asp Ile Ala Tyr Asn Glu Ser Asn Pro His Pro Gly Val Ile Ile Asn
            50                  55                  60

His Pro Tyr Gly Ser Asp Val Tyr Lys Gly Val Pro Lys Asp Tyr Val
65                  70                  75                  80

Gly Glu Asp Ile Asn Pro Pro Asn Phe Tyr Ala Val Leu Leu Ala Asn
                85                  90                  95

Lys Ser Ala Leu Thr Gly Thr Gly Ser Gly Lys Val Leu Asp Ser Gly
            100                 105                 110

Pro Asn Asp His Val Phe Ile Tyr Tyr Thr Asp His Gly Gly Ala Gly
            115                 120                 125

Val Leu Gly Met Pro Ser Lys Pro Tyr Ile Ala Ala Ser Asp Leu Asn
            130                 135                 140

Asp Val Leu Lys Lys Lys His Ala Ser Gly Thr Tyr Lys Ser Ile Val
145                 150                 155                 160

Phe Tyr Val Glu Ser Cys Glu Ser Gly Ser Met Phe Asp Gly Leu Leu
                165                 170                 175

Pro Glu Asp His Asn Ile Tyr Val Met Gly Ala Ser Asp Thr Gly Glu
            180                 185                 190

Ser Ser Trp Val Thr Tyr Cys Pro Leu Gln His Pro Ser Pro Pro Pro
            195                 200                 205

Glu Tyr Asp Val Cys Val Gly Asp Leu Phe Ser Val Ala Trp Leu Glu
            210                 215                 220

Asp Cys Asp Val His Asn Leu Gln Thr Glu Thr Phe Gln Gln Gln Tyr
225                 230                 235                 240

Glu Val Val Lys Asn Lys Thr Ile Val Ala Leu Ile Glu Asp Gly Thr
                245                 250                 255

His Val Val Gln Tyr Gly Asp Val Gly Leu Ser Lys Gln Thr Leu Phe
                260                 265                 270

Val Tyr Met Gly Thr Asp Pro Ala Asn
            275                 280
```

```
<210> SEQ ID NO 19
<211> LENGTH: 75
<212> TYPE: PRT
<213> ORGANISM: Artificial
<220> FEATURE:
<223> OTHER INFORMATION: Modified Bacteriocin AS-48K

<400> SEQUENCE: 19

Val Val Glu Ala Gly Gly Trp Val Thr Thr Ile Val Ser Ile Leu Thr
1               5                   10                  15

Ala Val Gly Ser Gly Gly Leu Ser Leu Leu Ala Ala Ala Gly Arg Glu
                20                  25                  30

Ser Ile Lys Ala Tyr Leu Lys Lys Glu Ile Lys Lys Lys Gly Lys Arg
            35                  40                  45

Ala Val Ile Ala Trp Met Ala Lys Glu Phe Gly Ile Pro Ala Ala Val
        50                  55                  60

Ala Gly Thr Val Leu Asn His Val Lys Lys Lys
65                  70                  75

<210> SEQ ID NO 20
<211> LENGTH: 31
<212> TYPE: PRT
<213> ORGANISM: Oldenlandia affinis

<400> SEQUENCE: 20

Gly Leu Pro Val Cys Gly Glu Thr Cys Val Gly Gly Thr Cys Asn Thr
1               5                   10                  15

Pro Gly Cys Thr Cys Ser Trp Pro Val Cys Thr Arg Asn Gly Leu
                20                  25                  30

<210> SEQ ID NO 21
<211> LENGTH: 16
<212> TYPE: PRT
<213> ORGANISM: Conus sp.

<400> SEQUENCE: 21

Gly Val Cys Cys Gly Tyr Lys Leu Cys His Pro Cys Ala Gly Asn His
1               5                   10                  15

<210> SEQ ID NO 22
<211> LENGTH: 25
<212> TYPE: PRT
<213> ORGANISM: Artificial
<220> FEATURE:
<223> OTHER INFORMATION: Thanatin analog

<400> SEQUENCE: 22

Gly Ile Ser Lys Lys Pro Val Pro Ile Ile Tyr Cys Asn Arg Arg Thr
1               5                   10                  15

Gly Lys Cys Gln Arg Met Asn His Val
                20                  25

<210> SEQ ID NO 23
<211> LENGTH: 42
<212> TYPE: PRT
<213> ORGANISM: Homo sapiens

<400> SEQUENCE: 23

Ser Ala Asp Ser His Glu Lys Arg His His Gly Tyr Arg Arg Lys Phe
1               5                   10                  15
```

```
His Glu Lys His His Ser His Arg Glu Phe Pro Phe Tyr Gly Asp Tyr
         20              25              30

Gly Ser Asn Tyr Leu Tyr Asp Asn His Val
         35              40

<210> SEQ ID NO 24
<211> LENGTH: 43
<212> TYPE: PRT
<213> ORGANISM: Homo sapiens

<400> SEQUENCE: 24

Gly Leu Pro Asp Ser His Glu Lys Arg His His Gly Tyr Arg Arg Lys
1               5               10              15

Phe His Glu Lys His His Ser His Arg Glu Phe Pro Phe Tyr Gly Asp
         20              25              30

Tyr Gly Ser Asn Tyr Leu Tyr Asp Asn His Val
         35              40

<210> SEQ ID NO 25
<211> LENGTH: 36
<212> TYPE: PRT
<213> ORGANISM: Homo sapiens

<400> SEQUENCE: 25

Gly Ala Asp Ser His Ala Lys Arg His His Gly Tyr Lys Arg Lys Phe
1               5               10              15

His Glu Lys His His Ser His Arg Gly Tyr Arg Ser Asn Tyr Leu Tyr
         20              25              30

Asp Asn His Val
         35

<210> SEQ ID NO 26
<211> LENGTH: 36
<212> TYPE: PRT
<213> ORGANISM: Homo sapiens

<400> SEQUENCE: 26

Gly Leu Asp Ser His Ala Lys Arg His His Gly Tyr Lys Arg Lys Phe
1               5               10              15

His Glu Lys His His Ser His Arg Gly Tyr Arg Ser Asn Tyr Leu Tyr
         20              25              30

Asp Asn His Val
         35

<210> SEQ ID NO 27
<211> LENGTH: 26
<212> TYPE: PRT
<213> ORGANISM: Artificial
<220> FEATURE:
<223> OTHER INFORMATION: modified human neuromedin U

<400> SEQUENCE: 27

Arg Val Asp Glu Glu Phe Gln Ser Pro Phe Ala Ser Gln Ser Arg Gly
1               5               10              15

Tyr Phe Leu Phe Arg Pro Arg Asn His Val
         20              25

<210> SEQ ID NO 28
<211> LENGTH: 33
<212> TYPE: PRT
<213> ORGANISM: Artificial
```

-continued

```
<220> FEATURE:
<223> OTHER INFORMATION: modified human salusin alpha

<400> SEQUENCE: 28

Gly Ile Ser Gly Ala Leu Pro Pro Ala Pro Ala Ala Pro Arg Pro Ala
1               5                   10                  15

Leu Arg Ala Gln Arg Ala Gly Pro Ala Gly Pro Gly Ala Lys Asn His
            20                  25                  30

Val

<210> SEQ ID NO 29
<211> LENGTH: 28
<212> TYPE: PRT
<213> ORGANISM: Artificial
<220> FEATURE:
<223> OTHER INFORMATION: modified rat neuromedin U

<400> SEQUENCE: 29

Gly Ile Lys Tyr Lys Val Asn Glu Tyr Gln Gly Pro Val Ala Pro Ser
1               5                   10                  15

Gly Gly Phe Phe Leu Phe Arg Pro Arg Asn His Val
            20                  25

<210> SEQ ID NO 30
<211> LENGTH: 40
<212> TYPE: PRT
<213> ORGANISM: Artificial
<220> FEATURE:
<223> OTHER INFORMATION: modified human apelin

<400> SEQUENCE: 30

Gly Leu Val Gln Pro Arg Gly Ser Arg Asn Gly Pro Gly Pro Trp Gln
1               5                   10                  15

Gly Gly Arg Arg Lys Phe Arg Arg Gln Arg Pro Arg Leu Ser His Lys
            20                  25                  30

Gly Pro Met Pro Phe Asn His Val
            35                  40

<210> SEQ ID NO 31
<211> LENGTH: 32
<212> TYPE: PRT
<213> ORGANISM: Artificial
<220> FEATURE:
<223> OTHER INFORMATION: modified human galanin

<400> SEQUENCE: 31

Gly Leu Thr Ser Gly Trp Thr Leu Asn Ser Ala Gly Tyr Leu Leu Gly
1               5                   10                  15

Pro His Ala Val Gly Asn His Arg Ser Phe Ser Asp Lys Asn His Val
            20                  25                  30

<210> SEQ ID NO 32
<211> LENGTH: 10
<212> TYPE: PRT
<213> ORGANISM: Artificial
<220> FEATURE:
<223> OTHER INFORMATION: Artificial peptide

<400> SEQUENCE: 32

Gly Leu Pro Pro Pro Ile Phe Asn His Val
1               5                   10

<210> SEQ ID NO 33
```

```
<211> LENGTH: 10
<212> TYPE: PRT
<213> ORGANISM: Artificial
<220> FEATURE:
<223> OTHER INFORMATION: Artificial peptide

<400> SEQUENCE: 33

Ser Leu Pro Pro Pro Ile Phe Asn His Val
1               5                   10

<210> SEQ ID NO 34
<211> LENGTH: 10
<212> TYPE: PRT
<213> ORGANISM: Artificial
<220> FEATURE:
<223> OTHER INFORMATION: Artificial peptide

<400> SEQUENCE: 34

His Leu Pro Pro Pro Ile Phe Asn His Val
1               5                   10

<210> SEQ ID NO 35
<211> LENGTH: 10
<212> TYPE: PRT
<213> ORGANISM: Artificial
<220> FEATURE:
<223> OTHER INFORMATION: Artificial peptide

<400> SEQUENCE: 35

Glu Ile Asn Ser Thr Glu Ile Asn His Val
1               5                   10

<210> SEQ ID NO 36
<211> LENGTH: 9
<212> TYPE: PRT
<213> ORGANISM: Artificial
<220> FEATURE:
<223> OTHER INFORMATION: Artificial peptide

<400> SEQUENCE: 36

Arg Val Thr Arg Pro Val Asn His Val
1               5

<210> SEQ ID NO 37
<211> LENGTH: 8
<212> TYPE: PRT
<213> ORGANISM: Artificial
<220> FEATURE:
<223> OTHER INFORMATION: Artificial peptide

<400> SEQUENCE: 37

Lys Ala Leu Val Ile Asn His Val
1               5

<210> SEQ ID NO 38
<211> LENGTH: 6
<212> TYPE: PRT
<213> ORGANISM: Artificial
<220> FEATURE:
<223> OTHER INFORMATION: Artificial peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 38

Xaa Ile Gly Gly Ile Arg
1               5
```

-continued

```
<210> SEQ ID NO 39
<211> LENGTH: 6
<212> TYPE: PRT
<213> ORGANISM: Artificial
<220> FEATURE:
<223> OTHER INFORMATION: Artificial peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 39

Leu Xaa Gly Gly Ile Arg
1               5

<210> SEQ ID NO 40
<211> LENGTH: 5
<212> TYPE: PRT
<213> ORGANISM: Artificial
<220> FEATURE:
<223> OTHER INFORMATION: Artificial peptide

<400> SEQUENCE: 40

Tyr Arg Asn His Val
1               5

<210> SEQ ID NO 41
<211> LENGTH: 5
<212> TYPE: PRT
<213> ORGANISM: Artificial
<220> FEATURE:
<223> OTHER INFORMATION: Artificial peptide

<400> SEQUENCE: 41

Gly Leu Pro Val Arg
1               5

<210> SEQ ID NO 42
<211> LENGTH: 5
<212> TYPE: PRT
<213> ORGANISM: Artificial
<220> FEATURE:
<223> OTHER INFORMATION: Artificial peptide

<400> SEQUENCE: 42

Thr Arg Asn His Val
1               5

<210> SEQ ID NO 43
<211> LENGTH: 263
<212> TYPE: PRT
<213> ORGANISM: Artificial
<220> FEATURE:
<223> OTHER INFORMATION: peptide construct GFP + NHV

<400> SEQUENCE: 43

Met His His His His His His Ser Ser Gly Val Asp Leu Gly Thr Glu
1               5                   10                  15

Asn Leu Tyr Phe Gln Ser Met Ser Lys Gly Glu Glu Leu Phe Thr Gly
                20                  25                  30

Val Val Pro Ile Leu Val Glu Leu Asp Gly Asp Val Asn Gly His Lys
            35                  40                  45

Phe Ser Val Ser Gly Glu Gly Glu Gly Asp Ala Thr Tyr Gly Lys Leu
        50                  55                  60
```

-continued

```
Thr Leu Lys Phe Ile Cys Thr Thr Gly Lys Leu Pro Val Pro Trp Pro
65                  70                  75                  80

Thr Leu Val Thr Thr Leu Thr Tyr Gly Val Gln Cys Phe Ser Arg Tyr
                85                  90                  95

Pro Asp His Met Lys Gln His Asp Phe Phe Lys Ser Ala Met Pro Glu
                100                 105                 110

Gly Tyr Val Gln Glu Arg Thr Ile Phe Phe Lys Asp Asp Gly Asn Tyr
                115                 120                 125

Lys Thr Arg Ala Glu Val Lys Phe Glu Gly Asp Thr Leu Val Asn Arg
        130                 135                 140

Ile Glu Leu Lys Gly Ile Asp Phe Lys Glu Asp Gly Asn Ile Leu Gly
145                 150                 155                 160

His Lys Leu Glu Tyr Asn Tyr Asn Ser His Asn Val Tyr Ile Met Ala
                165                 170                 175

Asp Lys Gln Lys Asn Gly Ile Lys Val Asn Phe Lys Ile Arg His Asn
                180                 185                 190

Ile Glu Asp Gly Ser Val Gln Leu Ala Asp His Tyr Gln Gln Asn Thr
                195                 200                 205

Pro Ile Gly Asp Gly Pro Val Leu Leu Pro Asp Asn His Tyr Leu Ser
        210                 215                 220

Thr Gln Ser Ala Leu Ser Lys Asp Pro Asn Glu Lys Arg Asp His Met
225                 230                 235                 240

Val Leu Leu Glu Phe Val Thr Ala Ala Gly Ile Thr Leu Gly Met Asp
                245                 250                 255

Glu Leu Tyr Lys Asn His Val
                260
```

```
<210> SEQ ID NO 44
<211> LENGTH: 5
<212> TYPE: PRT
<213> ORGANISM: Artificial
<220> FEATURE:
<223> OTHER INFORMATION: Artificial peptide with K at position 4 being
      biotinylated

<400> SEQUENCE: 44

Gly Ile Gly Lys Arg
1               5
```

```
<210> SEQ ID NO 45
<211> LENGTH: 129
<212> TYPE: PRT
<213> ORGANISM: Artificial
<220> FEATURE:
<223> OTHER INFORMATION: human anti-ABL scFv fragment

<400> SEQUENCE: 45

Met His His His His His His Ser Ser Gly Val Asp Leu Gly Thr Glu
1               5                   10                  15

Asn Leu Tyr Phe Gln Ser Met Gly Gly Ser Gly Ser Ser Val Ser Ser
                20                  25                  30

Val Pro Thr Lys Leu Glu Val Val Asp Ala Thr Pro Thr Ser Leu Lys
        35                  40                  45

Ile Ser Trp Asp Ala Tyr Tyr Ser Ser Trp Gln Asn Val Lys Tyr Tyr
        50                  55                  60

Arg Ile Thr Tyr Gly Glu Thr Gly Gly Asp Ser Pro Val Gln Glu Phe
65                  70                  75                  80
```

-continued

```
Thr Val Pro Gly Tyr Tyr Ser Thr Ala Thr Ile Ser Gly Leu Lys Pro
            85              90              95

Gly Val Asp Tyr Thr Ile Thr Val Tyr Ala Tyr Asp Thr Phe Phe Pro
            100             105             110

Gly Tyr Glu Pro Asn Ser Pro Ile Ser Ile Asn Tyr Arg Thr Asn His
        115             120             125

Val

<210> SEQ ID NO 46
<211> LENGTH: 184
<212> TYPE: PRT
<213> ORGANISM: Artificial
<220> FEATURE:
<223> OTHER INFORMATION: darpin specific for ERK

<400> SEQUENCE: 46

Met His His His His His His Ser Ser Gly Val Asp Leu Gly Thr Glu
1               5               10              15

Asn Leu Tyr Phe Gln Ser Met Gly Ser Asp Leu Gly Lys Lys Leu Leu
            20              25              30

Glu Ala Ala Arg Ala Gly Gln Asp Asp Glu Val Arg Ile Leu Met Ala
        35              40              45

Asn Gly Ala Asp Val Asn Ala His Asp Gln Gly Ser Thr Pro Leu
        50              55              60

His Leu Ala Ala Trp Ile Gly His Pro Glu Ile Val Glu Val Leu Leu
65              70              75              80

Lys His Gly Ala Asp Val Asn Ala Arg Asp Thr Asp Gly Trp Thr Pro
            85              90              95

Leu His Leu Ala Ala Asp Asn Gly His Leu Glu Ile Val Glu Val Leu
            100             105             110

Leu Lys Tyr Gly Ala Asp Val Asn Ala Gln Asp Ala Tyr Gly Leu Thr
        115             120             125

Pro Leu His Leu Ala Ala Asp Arg Gly His Leu Glu Ile Val Glu Val
        130             135             140

Leu Leu Lys His Gly Ala Asp Val Asn Ala Gln Asp Lys Phe Gly Lys
145             150             155             160

Thr Ala Phe Asp Ile Ser Ile Asp Asn Gly Asn Glu Asp Leu Ala Glu
            165             170             175

Ile Leu Gln Lys Leu Asn His Val
            180

<210> SEQ ID NO 47
<211> LENGTH: 12
<212> TYPE: PRT
<213> ORGANISM: Artificial
<220> FEATURE:
<223> OTHER INFORMATION: Synthetic peptide

<400> SEQUENCE: 47

Gly Leu Tyr Arg Arg Gly Arg Leu Tyr Arg Arg Asn
1               5               10

<210> SEQ ID NO 48
<211> LENGTH: 14
<212> TYPE: PRT
<213> ORGANISM: Artificial
<220> FEATURE:
<223> OTHER INFORMATION: Synthetic peptide
```

<400> SEQUENCE: 48

Gly Ile Ser Thr Lys Ser Ile Pro Pro Ile Ser Tyr Arg Asn
1               5               10

<210> SEQ ID NO 49
<211> LENGTH: 187
<212> TYPE: PRT
<213> ORGANISM: Artificial
<220> FEATURE:
<223> OTHER INFORMATION: Synthetic peptide 6xHis-TEV-GLGSG-DARPin9_26-
      GSGS-NGL

<400> SEQUENCE: 49

Gly His His His His His His Gly Thr Glu Asn Leu Tyr Phe Gln Gly
1               5               10                  15

Leu Gly Ser Gly Ser Asp Leu Gly Lys Lys Leu Leu Glu Ala Ala Arg
            20              25                  30

Ala Gly Gln Asp Asp Glu Val Arg Ile Leu Met Ala Asn Gly Ala Asp
        35              40                  45

Val Asn Ala Lys Asp Phe Tyr Gly Ile Thr Pro Leu His Leu Ala Ala
    50              55                  60

Ala Tyr Gly His Leu Glu Ile Val Glu Val Leu Leu Lys His Gly Ala
65              70                  75                  80

Asp Val Asn Ala His Asp Trp Asn Gly Trp Thr Pro Leu His Leu Ala
            85              90                  95

Ala Lys Tyr Gly His Leu Glu Ile Val Glu Val Leu Leu Lys His Gly
            100             105                 110

Ala Asp Val Asn Ala Ile Asp Asn Ala Gly Lys Thr Pro Leu His Leu
            115             120                 125

Ala Ala Ala His Gly His Leu Glu Ile Val Glu Val Leu Leu Lys Tyr
        130             135                 140

Gly Ala Asp Val Asn Ala Gln Asp Lys Phe Gly Lys Thr Pro Phe Asp
145             150                 155                 160

Leu Ala Ile Asp Asn Gly Asn Glu Asp Ile Ala Glu Val Leu Gln Lys
            165             170                 175

Ala Ala Lys Leu Gly Ser Gly Ser Asn Gly Leu
            180             185

<210> SEQ ID NO 50
<211> LENGTH: 8
<212> TYPE: PRT
<213> ORGANISM: Artificial
<220> FEATURE:
<223> OTHER INFORMATION: Peptide inhibitor

<400> SEQUENCE: 50

Leu Lys Val Ile His Asn Ser Leu
1               5

<210> SEQ ID NO 51
<211> LENGTH: 16
<212> TYPE: PRT
<213> ORGANISM: Artificial
<220> FEATURE:
<223> OTHER INFORMATION: Peptide substrate

<400> SEQUENCE: 51

Lys Leu Gly Thr Ser Pro Gly Arg Leu Arg Tyr Ala Gly Asn Gly Leu
1               5               10                  15

-continued

```
<210> SEQ ID NO 52
<211> LENGTH: 16
<212> TYPE: PRT
<213> ORGANISM: Artificial
<220> FEATURE:
<223> OTHER INFORMATION: GN14-HV

<400> SEQUENCE: 52

Gly Ile Ser Thr Lys Ser Ile Pro Pro Ile Ser Tyr Arg Asn His Val
1               5                   10                  15

<210> SEQ ID NO 53
<211> LENGTH: 18
<212> TYPE: PRT
<213> ORGANISM: Artificial
<220> FEATURE:
<223> OTHER INFORMATION: GN14-SLAN

<400> SEQUENCE: 53

Gly Ile Ser Thr Lys Ser Ile Pro Pro Ile Ser Tyr Arg Asn Ser Leu
1               5                   10                  15

Ala Asn

<210> SEQ ID NO 54
<211> LENGTH: 16
<212> TYPE: PRT
<213> ORGANISM: Artificial
<220> FEATURE:
<223> OTHER INFORMATION: SFTI analog

<400> SEQUENCE: 54

Gly Arg Cys Thr Lys Ser Ile Pro Pro Ile Cys Phe Pro Asn His Val
1               5                   10                  15

<210> SEQ ID NO 55
<211> LENGTH: 7
<212> TYPE: PRT
<213> ORGANISM: Artificial
<220> FEATURE:
<223> OTHER INFORMATION: RV7 peptide

<400> SEQUENCE: 55

Arg Leu Tyr Arg Asn His Val
1               5

<210> SEQ ID NO 56
<211> LENGTH: 6
<212> TYPE: PRT
<213> ORGANISM: Artificial
<220> FEATURE:
<223> OTHER INFORMATION: Peptide substrate

<400> SEQUENCE: 56

Arg Tyr Ala Asn Gly Ile
1               5

<210> SEQ ID NO 57
<211> LENGTH: 6
<212> TYPE: PRT
<213> ORGANISM: Artificial
<220> FEATURE:
<223> OTHER INFORMATION: synthetic peptide, K labeled with FAM

<400> SEQUENCE: 57

Gly Leu Ala Lys Arg Gly
1               5
```

-continued

```
<210> SEQ ID NO 58
<211> LENGTH: 10
<212> TYPE: PRT
<213> ORGANISM: Artificial
<220> FEATURE:
<223> OTHER INFORMATION: ligated peptide, K labeled with FAM

<400> SEQUENCE: 58

Arg Tyr Ala Asn Gly Leu Ala Lys Arg Gly
1               5                   10

<210> SEQ ID NO 59
<211> LENGTH: 16
<212> TYPE: PRT
<213> ORGANISM: Artificial
<220> FEATURE:
<223> OTHER INFORMATION: Artificial peptide

<400> SEQUENCE: 59

Gly Ile Ser Thr Lys Ser Ile Pro Pro Ile Ser Tyr Arg Asn Ser Leu
1               5                   10                  15

<210> SEQ ID NO 60
<211> LENGTH: 18
<212> TYPE: PRT
<213> ORGANISM: Artificial
<220> FEATURE:
<223> OTHER INFORMATION: Artificial peptide

<400> SEQUENCE: 60

Gly Ile Ser Thr Lys Ser Ile Pro Pro Ile Ser Tyr Arg Asn Ser Leu
1               5                   10                  15

Ala Asn

<210> SEQ ID NO 61
<211> LENGTH: 18
<212> TYPE: PRT
<213> ORGANISM: Artificial
<220> FEATURE:
<223> OTHER INFORMATION: Artificial peptide

<400> SEQUENCE: 61

Gly Ile Ser Thr Lys Ser Ile Pro Pro Ile Ser Tyr Arg Asn Ser Ile
1               5                   10                  15

Gln Gln

<210> SEQ ID NO 62
<211> LENGTH: 17
<212> TYPE: PRT
<213> ORGANISM: Artificial
<220> FEATURE:
<223> OTHER INFORMATION: Artificial peptide

<400> SEQUENCE: 62

Gly Ile Ser Thr Lys Ser Ile Pro Pro Ile Ser Tyr Arg Asn Ser Ile
1               5                   10                  15

Gln

<210> SEQ ID NO 63
<211> LENGTH: 16
<212> TYPE: PRT
<213> ORGANISM: Artificial
<220> FEATURE:
<223> OTHER INFORMATION: Artificial peptide
```

```
<400> SEQUENCE: 63

Gly Ile Ser Thr Lys Ser Ile Pro Pro Ile Ser Tyr Arg Asn Ser Ile
1               5                   10                  15

<210> SEQ ID NO 64
<211> LENGTH: 18
<212> TYPE: PRT
<213> ORGANISM: Artificial
<220> FEATURE:
<223> OTHER INFORMATION: Artificial peptide

<400> SEQUENCE: 64

Gly Ile Ser Thr Lys Ser Ile Pro Pro Ile Ser Tyr Arg Asn Ser Leu
1               5                   10                  15

Ala Met

<210> SEQ ID NO 65
<211> LENGTH: 17
<212> TYPE: PRT
<213> ORGANISM: Artificial
<220> FEATURE:
<223> OTHER INFORMATION: Artificial peptide

<400> SEQUENCE: 65

Gly Ile Ser Thr Lys Ser Ile Pro Pro Ile Ser Tyr Arg Asn Ser Leu
1               5                   10                  15

Ala

<210> SEQ ID NO 66
<211> LENGTH: 18
<212> TYPE: PRT
<213> ORGANISM: Artificial
<220> FEATURE:
<223> OTHER INFORMATION: Artificial peptide

<400> SEQUENCE: 66

Gly Ile Ser Thr Lys Ser Ile Pro Pro Ile Ser Tyr Arg Asn Ser Leu
1               5                   10                  15

Asp Asn

<210> SEQ ID NO 67
<211> LENGTH: 18
<212> TYPE: PRT
<213> ORGANISM: Artificial
<220> FEATURE:
<223> OTHER INFORMATION: Artificial peptide

<400> SEQUENCE: 67

Gly Ile Ser Thr Lys Ser Ile Pro Pro Ile Ser Tyr Arg Asn Ser Leu
1               5                   10                  15

Asp Ile

<210> SEQ ID NO 68
<211> LENGTH: 17
<212> TYPE: PRT
<213> ORGANISM: Artificial
<220> FEATURE:
<223> OTHER INFORMATION: Artificial peptide

<400> SEQUENCE: 68

Gly Ile Ser Thr Lys Ser Ile Pro Pro Ile Ser Tyr Arg Asn Ser Leu
1               5                   10                  15

Asp
```

```
<210> SEQ ID NO 69
<211> LENGTH: 18
<212> TYPE: PRT
<213> ORGANISM: Artificial
<220> FEATURE:
<223> OTHER INFORMATION: Artificial peptide

<400> SEQUENCE: 69

Gly Ile Ser Thr Lys Ser Ile Pro Pro Ile Ser Tyr Arg Asn Ser Leu
1               5                   10                  15

Ser Gly

<210> SEQ ID NO 70
<211> LENGTH: 17
<212> TYPE: PRT
<213> ORGANISM: Artificial
<220> FEATURE:
<223> OTHER INFORMATION: Artificial peptide

<400> SEQUENCE: 70

Gly Ile Ser Thr Lys Ser Ile Pro Pro Ile Ser Tyr Arg Asn Ser Leu
1               5                   10                  15

Ser

<210> SEQ ID NO 71
<211> LENGTH: 15
<212> TYPE: PRT
<213> ORGANISM: Artificial
<220> FEATURE:
<223> OTHER INFORMATION: Artificial peptide

<400> SEQUENCE: 71

Gly Ile Ser Thr Lys Ser Ile Pro Pro Ile Ser Tyr Arg Asn Ser
1               5                   10                  15

<210> SEQ ID NO 72
<211> LENGTH: 18
<212> TYPE: PRT
<213> ORGANISM: Artificial
<220> FEATURE:
<223> OTHER INFORMATION: Artificial peptide

<400> SEQUENCE: 72

Gly Ile Ser Thr Lys Ser Ile Pro Pro Ile Ser Tyr Arg Asn His Val
1               5                   10                  15

Ile Ala

<210> SEQ ID NO 73
<211> LENGTH: 17
<212> TYPE: PRT
<213> ORGANISM: Artificial
<220> FEATURE:
<223> OTHER INFORMATION: Artificial peptide

<400> SEQUENCE: 73

Gly Ile Ser Thr Lys Ser Ile Pro Pro Ile Ser Tyr Arg Asn His Val
1               5                   10                  15

Ile

<210> SEQ ID NO 74
<211> LENGTH: 16
<212> TYPE: PRT
<213> ORGANISM: Artificial
```

```
<220> FEATURE:
<223> OTHER INFORMATION: Artificial peptide

<400> SEQUENCE: 74

Gly Ile Ser Thr Lys Ser Ile Pro Pro Ile Ser Tyr Arg Asn His Val
1               5                   10                  15

<210> SEQ ID NO 75
<211> LENGTH: 15
<212> TYPE: PRT
<213> ORGANISM: Artificial
<220> FEATURE:
<223> OTHER INFORMATION: Artificial peptide

<400> SEQUENCE: 75

Gly Ile Ser Thr Lys Ser Ile Pro Pro Ile Ser Tyr Arg Asn His
1               5                   10                  15

<210> SEQ ID NO 76
<211> LENGTH: 16
<212> TYPE: PRT
<213> ORGANISM: Artificial
<220> FEATURE:
<223> OTHER INFORMATION: Artificial peptide

<400> SEQUENCE: 76

Gly Ile Ser Thr Lys Ser Ile Pro Pro Ile Ser Tyr Arg Asp Gly Ile
1               5                   10                  15

<210> SEQ ID NO 77
<211> LENGTH: 16
<212> TYPE: PRT
<213> ORGANISM: Artificial
<220> FEATURE:
<223> OTHER INFORMATION: Artificial peptide

<400> SEQUENCE: 77

Gly Ile Ser Thr Lys Ser Ile Pro Pro Ile Ser Tyr Arg Asp Ser Leu
1               5                   10                  15

<210> SEQ ID NO 78
<211> LENGTH: 14
<212> TYPE: PRT
<213> ORGANISM: Artificial
<220> FEATURE:
<223> OTHER INFORMATION: Artificial peptide
<220> FEATURE:
<221> NAME/KEY: misc_feature
<222> LOCATION: (13)..(13)
<223> OTHER INFORMATION: Xaa can be any naturally occurring amino acid

<400> SEQUENCE: 78

Gly Leu Tyr Arg Arg Gly Arg Leu Tyr Arg Arg Asn Xaa Leu
1               5                   10

<210> SEQ ID NO 79
<211> LENGTH: 14
<212> TYPE: PRT
<213> ORGANISM: Artificial
<220> FEATURE:
<223> OTHER INFORMATION: Artificial peptide
<220> FEATURE:
<221> NAME/KEY: misc_feature
<222> LOCATION: (14)..(14)
<223> OTHER INFORMATION: Xaa can be any naturally occurring amino acid
```

<400> SEQUENCE: 79

Gly Leu Tyr Arg Arg Gly Arg Leu Tyr Arg Arg Asn Gly Xaa
1               5                   10

<210> SEQ ID NO 80
<211> LENGTH: 488
<212> TYPE: PRT
<213> ORGANISM: Clitoria ternatea

<400> SEQUENCE: 80

Met Ala Val Asp His Cys Phe Leu Lys Lys Thr Cys Tyr Tyr Gly
1               5                   10                  15

Phe Val Leu Trp Ser Trp Met Leu Met Met Ser Leu His Ser Lys Ala
                20                  25                  30

Ala Arg Leu Asn Pro Gln Lys Glu Trp Asp Ser Val Ile Arg Leu Pro
            35                  40                  45

Thr Glu Pro Val Asp Ala Asp Thr Asp Glu Val Gly Thr Arg Trp Ala
        50                  55                  60

Val Leu Val Ala Gly Ser Asn Gly Tyr Glu Asn Tyr Arg His Gln Ala
65                  70                  75                  80

Asp Val Cys His Ala Tyr Gln Leu Leu Ile Lys Gly Gly Leu Lys Glu
                85                  90                  95

Glu Asn Ile Val Val Phe Met Tyr Asp Asp Ile Ala Trp His Glu Leu
                100                 105                 110

Asn Pro Arg Pro Gly Val Ile Ile Asn Asn Pro Arg Gly Glu Asp Val
            115                 120                 125

Tyr Ala Gly Val Pro Lys Asp Tyr Thr Gly Glu Asp Val Thr Ala Glu
        130                 135                 140

Asn Leu Phe Ala Val Ile Leu Gly Asp Arg Ser Lys Val Lys Gly Gly
145                 150                 155                 160

Ser Gly Lys Val Ile Asn Ser Lys Pro Glu Asp Arg Ile Phe Ile Phe
                165                 170                 175

Tyr Ser Asp His Gly Gly Pro Gly Val Leu Gly Met Pro Asn Glu Gln
                180                 185                 190

Ile Leu Tyr Ala Met Asp Phe Ile Asp Val Leu Lys Lys Lys His Ala
            195                 200                 205

Ser Gly Gly Tyr Arg Glu Met Val Ile Tyr Val Glu Ala Cys Glu Ser
        210                 215                 220

Gly Ser Leu Phe Glu Gly Ile Met Pro Lys Asp Leu Asn Val Phe Val
225                 230                 235                 240

Thr Thr Ala Ser Asn Ala Gln Glu Asn Ser Trp Gly Thr Tyr Cys Pro
                245                 250                 255

Gly Thr Glu Pro Ser Pro Pro Glu Tyr Thr Thr Cys Leu Gly Asp
                260                 265                 270

Leu Tyr Ser Val Ala Trp Met Glu Asp Ser Glu Ser His Asn Leu Arg
            275                 280                 285

Arg Glu Thr Val Asn Gln Gln Tyr Arg Ser Val Lys Glu Arg Thr Ser
        290                 295                 300

Asn Phe Lys Asp Tyr Ala Met Gly Ser His Val Met Gln Tyr Gly Asp
305                 310                 315                 320

Thr Asn Ile Thr Ala Glu Lys Leu Tyr Leu Phe Gln Gly Phe Asp Pro
                325                 330                 335

Ala Thr Val Asn Leu Pro Pro His Asn Gly Arg Ile Glu Ala Lys Met
            340                 345                 350

-continued

```
Glu Val Val His Gln Arg Asp Ala Glu Leu Leu Phe Met Trp Gln Met
        355                 360                 365

Tyr Gln Arg Ser Asn His Leu Leu Gly Lys Lys Thr His Ile Leu Lys
    370                 375                 380

Gln Ile Ala Glu Thr Val Lys His Arg Asn His Leu Asp Gly Ser Val
385                 390                 395                 400

Glu Leu Ile Gly Val Leu Leu Tyr Gly Pro Gly Lys Gly Ser Pro Val
                405                 410                 415

Leu Gln Ser Val Arg Asp Pro Gly Leu Pro Leu Val Asp Asn Trp Ala
                420                 425                 430

Cys Leu Lys Ser Met Val Arg Val Phe Glu Ser His Cys Gly Ser Leu
                435                 440                 445

Thr Gln Tyr Gly Met Lys His Met Arg Ala Phe Ala Asn Ile Cys Asn
    450                 455                 460

Ser Gly Val Ser Glu Ser Ser Met Glu Glu Ala Cys Met Val Ala Cys
465                 470                 475                 480

Gly Gly His Asp Ala Gly His Leu
                485

<210> SEQ ID NO 81
<211> LENGTH: 474
<212> TYPE: PRT
<213> ORGANISM: Oldenlandia affinis

<400> SEQUENCE: 81

Met Val Arg Tyr Leu Ala Gly Ala Val Leu Leu Leu Val Val Leu Ser
1               5                   10                  15

Val Ala Ala Ala Val Ser Gly Ala Arg Asp Gly Asp Tyr Leu His Leu
            20                  25                  30

Pro Ser Glu Val Ser Arg Phe Phe Arg Pro Gln Glu Thr Asn Asp Asp
        35                  40                  45

His Gly Glu Asp Ser Val Gly Thr Arg Trp Ala Val Leu Ile Ala Gly
    50                  55                  60

Ser Lys Gly Tyr Ala Asn Tyr Arg His Gln Ala Gly Val Cys His Ala
65                  70                  75                  80

Tyr Gln Ile Leu Lys Arg Gly Gly Leu Lys Asp Glu Asn Ile Val Val
                85                  90                  95

Phe Met Tyr Asp Asp Ile Ala Tyr Asn Glu Ser Asn Pro Arg Pro Gly
            100                 105                 110

Val Ile Ile Asn Ser Pro His Gly Ser Asp Val Tyr Ala Gly Val Pro
        115                 120                 125

Lys Asp Tyr Thr Gly Glu Glu Val Asn Ala Lys Asn Phe Leu Ala Ala
    130                 135                 140

Ile Leu Gly Asn Lys Ser Ala Ile Thr Gly Gly Ser Gly Lys Val Val
145                 150                 155                 160

Asp Ser Gly Pro Asn Asp His Ile Phe Ile Tyr Tyr Thr Asp His Gly
                165                 170                 175

Ala Ala Gly Val Ile Gly Met Pro Ser Lys Pro Tyr Leu Tyr Ala Asp
            180                 185                 190

Glu Leu Asn Asp Ala Leu Lys Lys Lys His Ala Ser Gly Thr Tyr Lys
        195                 200                 205

Ser Leu Val Phe Tyr Leu Glu Ala Cys Glu Ser Gly Ser Met Phe Glu
    210                 215                 220
```

-continued

```
Gly Ile Leu Pro Glu Asp Leu Asn Ile Tyr Ala Leu Thr Ser Thr Asn
225             230             235             240

Thr Thr Glu Ser Ser Trp Cys Tyr Tyr Cys Pro Ala Gln Glu Asn Pro
            245             250             255

Pro Pro Pro Glu Tyr Asn Val Cys Leu Gly Asp Leu Phe Ser Val Ala
            260             265             270

Trp Leu Glu Asp Ser Asp Val Gln Asn Ser Trp Tyr Glu Thr Leu Asn
        275             280             285

Gln Gln Tyr His His Val Asp Lys Arg Ile Ser His Ala Ser His Ala
    290             295             300

Thr Gln Tyr Gly Asn Leu Lys Leu Gly Glu Glu Gly Leu Phe Val Tyr
305             310             315             320

Met Gly Ser Asn Pro Ala Asn Asp Asn Tyr Thr Ser Leu Asp Gly Asn
            325             330             335

Ala Leu Thr Pro Ser Ser Ile Val Val Asn Gln Arg Asp Ala Asp Leu
            340             345             350

Leu His Leu Trp Glu Lys Phe Arg Lys Ala Pro Glu Gly Ser Ala Arg
        355             360             365

Lys Glu Glu Ala Gln Thr Gln Ile Phe Lys Ala Met Ser His Arg Val
    370             375             380

His Ile Asp Ser Ser Ile Lys Leu Ile Gly Lys Leu Leu Phe Gly Ile
385             390             395             400

Glu Lys Cys Thr Glu Ile Leu Asn Ala Val Arg Pro Ala Gly Gln Pro
            405             410             415

Leu Val Asp Asp Trp Ala Cys Leu Arg Ser Leu Val Gly Thr Phe Glu
            420             425             430

Thr His Cys Gly Ser Leu Ser Glu Tyr Gly Met Arg His Thr Arg Thr
        435             440             445

Ile Ala Asn Ile Cys Asn Ala Gly Ile Ser Glu Glu Gln Met Ala Glu
    450             455             460

Ala Ala Ser Gln Ala Cys Ala Ser Ile Pro
465             470
```

```
<210> SEQ ID NO 82
<211> LENGTH: 488
<212> TYPE: PRT
<213> ORGANISM: Oldenlandia affinis

<400> SEQUENCE: 82
```

```
Met Val Arg Tyr Pro Ala Gly Ala Val Leu Leu Leu Val Val Leu Ser
1               5               10              15

Val Val Ala Val Asp Gly Ala Arg Asp Gly Tyr Leu Lys Leu Pro Ser
            20              25              30

Glu Val Ser Asp Phe Phe Arg Pro Arg Asn Thr Asn Asp Gly Asp Asp
        35              40              45

Ser Val Gly Thr Arg Trp Ala Val Leu Leu Ala Gly Ser Asn Gly Tyr
    50              55              60

Trp Asn Tyr Arg His Gln Ala Asp Leu Cys His Ala Tyr Gln Ile Leu
65              70              75              80

Lys Arg Gly Gly Leu Lys Asp Glu Asn Ile Val Val Phe Met Tyr Asp
            85              90              95

Asp Ile Ala Tyr Asn Glu Glu Asn Pro Arg Pro Gly Val Ile Ile Asn
            100             105             110
```

-continued

```
Ser Pro His Gly Ser Asp Val Tyr Ala Gly Val Pro Lys Asp Tyr Thr
        115                 120                 125

Gly Asp Gln Val Asn Ala Lys Asn Phe Leu Ala Ala Ile Leu Gly Asn
    130                 135                 140

Lys Ser Ala Ile Thr Gly Gly Ser Gly Lys Val Val Asn Ser Gly Pro
145                 150                 155                 160

Asn Asp His Ile Phe Ile Tyr Tyr Thr Asp His Gly Gly Pro Gly Val
                165                 170                 175

Leu Gly Met Pro Val Gly Pro Tyr Ile Tyr Ala Asp Asp Leu Ile Asp
            180                 185                 190

Thr Leu Lys Lys Lys His Ala Ser Gly Thr Tyr Lys Ser Leu Val Phe
        195                 200                 205

Tyr Leu Glu Ala Cys Glu Ser Gly Ser Met Phe Glu Gly Leu Leu Pro
    210                 215                 220

Glu Gly Leu Asn Ile Tyr Ala Thr Thr Ala Ser Asn Ala Glu Glu Ser
225                 230                 235                 240

Ser Trp Gly Thr Tyr Cys Pro Gly Glu Tyr Pro Ser Pro Pro Glu
            245                 250                 255

Tyr Asp Thr Cys Leu Gly Asp Leu Tyr Ser Val Ala Trp Met Glu Asp
            260                 265                 270

Ser Glu Val His Asn Leu Arg Ser Glu Thr Leu Lys Gln Gln Tyr His
        275                 280                 285

Leu Val Lys Ala Arg Thr Ser Asn Gly Asn Ser Ala Tyr Gly Ser His
        290                 295                 300

Val Met Gln Tyr Gly Asp Leu Lys Leu Ser Val Asp Asn Leu Phe Leu
305                 310                 315                 320

Tyr Met Gly Thr Asn Pro Ala Asn Asp Asn Tyr Thr Phe Val Asp Asp
            325                 330                 335

Asn Ala Leu Arg Pro Ser Ser Lys Ala Val Asn Gln Arg Asp Ala Asp
            340                 345                 350

Leu Leu His Phe Trp Asp Lys Phe Arg Lys Ala Pro Glu Gly Ser Ala
        355                 360                 365

Arg Lys Glu Glu Ala Arg Lys Gln Val Phe Glu Ala Met Ser His Arg
    370                 375                 380

Met His Ile Asp Asn Ser Ile Lys Leu Val Gly Lys Leu Leu Phe Gly
385                 390                 395                 400

Ile Glu Arg Gly Ala Glu Ile Leu Asp Ala Val Arg Pro Ala Gly Gln
            405                 410                 415

Pro Leu Ala Asp Asp Trp Thr Cys Leu Lys Ser Leu Val Arg Thr Phe
            420                 425                 430

Glu Thr His Cys Gly Ser Leu Ser Gln Tyr Gly Met Lys His Met Arg
        435                 440                 445

Thr Ile Ala Asn Ile Cys Asn Ala Gly Ile Thr Lys Glu Gln Met Ala
    450                 455                 460

Glu Ala Ser Ala Gln Ala Cys Ser Ser Val Pro Ser Asn Pro Trp Ser
465                 470                 475                 480

Ser Leu His Lys Gly Phe Ser Ala
                485
```

```
<210> SEQ ID NO 83
<211> LENGTH: 481
<212> TYPE: PRT
<213> ORGANISM: Hybanthus enneaspermus
```

-continued

<400> SEQUENCE: 83

Met Lys Leu Leu Val Pro Gly Val Leu Leu Leu Phe Leu Leu Ala Leu
1               5                   10                  15

Ser Gly Ile Ala Ala Gly Arg Pro Asp Asp Phe Leu Arg Leu Pro Ser
            20                  25                  30

Glu Ala Ala Lys Ser Phe Leu His Asn Asp Asp Asp Ser Val Gly Thr
        35                  40                  45

Arg Trp Ala Val Leu Ile Ala Gly Ser Lys Gly Trp Gln Asn Tyr Arg
    50                  55                  60

His Gln Ala Asp Val Cys His Ala Tyr Gln Ile Leu Lys Lys Gly Gly
65                  70                  75                  80

Leu Lys Asp Glu Asn Ile Ile Val Phe Met Tyr Asp Asp Ile Ala Tyr
                85                  90                  95

Asn Glu Ser Asn Pro Arg Pro Gly Ile Val Ile Asn Lys Pro Lys Gly
            100                 105                 110

Glu Asp Val Tyr Lys Gly Val Pro Lys Asp Tyr Thr Gly Glu Asn Val
            115                 120                 125

Asn Ala Val Asn Phe Leu Ala Val Leu Leu Ala Asn Arg Ser Ala Leu
    130                 135                 140

Thr Gly Gly Ser Gly Lys Val Leu Asp Ser Gly Pro Asn Asp Arg Ile
145                 150                 155                 160

Phe Ile Tyr Tyr Thr Asp His Gly Ala Pro Val Thr Ile Gly Met Pro
                165                 170                 175

Ser Lys Pro Tyr Leu Val Ala Lys Asp Leu Val Asp Thr Leu Lys Lys
            180                 185                 190

Lys His Ala Ala Gly Thr Tyr Lys Ser Met Val Phe Tyr Ile Glu Ser
        195                 200                 205

Cys Glu Ser Gly Ser Met Phe Asp Gly Leu Leu Pro Glu Asp Ala Asn
    210                 215                 220

Ile Tyr Gly Met Thr Ala Thr Asn Ser Thr Glu Gly Ser Trp Val Thr
225                 230                 235                 240

Tyr Cys Pro Gly Gln Thr Asp Asp Tyr Pro Glu Asp Asp Glu Tyr Asp
                245                 250                 255

Val Cys Phe Gly Asp Leu Trp Ser Val Ala Trp Leu Glu Asp Cys Asp
            260                 265                 270

Ala His Asn Leu Arg Thr Glu Thr Leu Asp Gln Gln Tyr Glu Val Val
        275                 280                 285

Lys Lys Lys Ile Glu Tyr Ala His Ile Pro Ala Gln Tyr Gly Asn Val
    290                 295                 300

Ser Leu Ala Lys Asp Ser Leu Phe Val Tyr Met Gly Thr Asp Pro Ala
305                 310                 315                 320

Asn Asp Asn Lys Thr Phe Val Glu Glu Asn Thr Leu Arg Arg Pro Leu
                325                 330                 335

Lys Ala Val His Ser Arg Asp Ala Asp Leu Leu His Phe Trp His Lys
            340                 345                 350

Tyr His Lys Ala Pro Glu Gly Thr Ser Arg Lys Ile Asp Ala Gln Lys
        355                 360                 365

Gln Leu Val Glu Val Leu Ser His Arg Thr His Val Asp Asn Ser Ile
    370                 375                 380

Lys Leu Val Gly Glu Leu Leu Phe Gly Val Gly Lys Ala Ser Glu Val
385                 390                 395                 400

Leu Asn Thr Ile Arg Pro Ala Gly Gln Pro Leu Val Asp Asp Trp Asp
                405                 410                 415

-continued

```
Cys Leu Lys Thr Met Val Arg Thr Phe Glu Thr His Cys Gly Ser Leu
            420             425             430

Ser Glu Tyr Gly Met Lys His Met Arg Ser Phe Ala Asn Met Cys Asn
            435             440             445

Ala Gly Val Gln Lys Glu Gln Met Ala Val Ala Ala Gly Gln Ala Cys
            450             455             460

Val Thr Phe Pro Ser Asn Pro Trp Ser Ser Leu Asp Glu Gly Phe Ser
465             470             475             480

Val

<210> SEQ ID NO 84
<211> LENGTH: 478
<212> TYPE: PRT
<213> ORGANISM: Petunia x hybrida

<400> SEQUENCE: 84

Met Ile Ser His Val Ala Gly Ile Leu Ile Leu Val Gly Phe Ser Ile
1               5               10              15

Leu Gly Ala Gly Glu Gly Arg Asn Val Leu Lys Leu Pro Ser Glu Ala
            20              25              30

Ser Arg Phe Phe Lys Lys Gly Glu Asp Asp Asp Ser Val Gly Thr Arg
            35              40              45

Trp Ala Val Leu Leu Ala Gly Ser Asn Ser Tyr Trp Asn Tyr Arg His
            50              55              60

Gln Ala Asp Val Cys His Ala Tyr Gln Leu Leu Arg Lys Gly Gly Leu
65              70              75              80

Lys Asp Glu Asn Ile Val Val Leu Met Tyr Asp Asp Ile Ala Tyr Asn
                85              90              95

Glu Glu Asn Pro Arg Lys Gly Val Ile Ile Asn Asn Pro Ala Gly Glu
            100             105             110

Asp Val Tyr Lys Gly Val Pro Lys Asp Tyr Thr Gly Asp Asp Val Asn
            115             120             125

Val Asp Asn Phe Leu Ala Val Leu Leu Gly Asn Lys Thr Ala Ile Thr
            130             135             140

Gly Gly Ser Gly Lys Val Val Asp Ser Gly Pro Asn Asp His Ile Phe
145             150             155             160

Ile Phe Tyr Thr Asp His Gly Gly Pro Gly Val Leu Gly Met Pro Thr
                165             170             175

Lys Pro Tyr Leu Tyr Ala Ser Asp Leu Ile Gly Ala Leu Lys Lys Lys
            180             185             190

His Ala Ser Gly Thr Tyr Lys Ser Leu Val Leu Tyr Val Glu Ala Cys
            195             200             205

Glu Ala Gly Ser Ile Phe Glu Gly Leu Leu Pro Glu Gly Leu Asn Val
            210             215             220

Tyr Ala Thr Thr Ala Ser Asp Ala Val Glu Gly Ser Trp Val Thr Tyr
225             230             235             240

Cys Pro Gly Gln Asn Pro Ser Pro Pro Glu Tyr Thr Thr Cys Leu
            245             250             255

Gly Asp Leu Tyr Ser Val Ser Trp Met Glu Asp Ser Glu Lys His Asn
            260             265             270

Leu Gln Thr Glu Ser Leu Arg Gln Gln Tyr His Leu Val Lys Glu Lys
            275             280             285

Ile Ala Tyr Ala Ser His Val Met Gln Tyr Gly Asp Leu Lys Leu Ser
            290             295             300
```

-continued

```
Met Asp Ser Leu Ser Met Tyr Met Gly Thr Asp Pro Ala Asn Asp Asn
305                 310                 315                 320

Tyr Thr Phe Val Asp Asp Asn Ser Leu Gly Thr Ser Ser Lys Ala Val
                325                 330                 335

Asn Gln Arg Asp Ala Asp Leu Leu His Phe Ser Asp Lys Phe Leu Lys
                340                 345                 350

Ala Pro Glu Gly Ser Ala Arg Lys Val Glu Ala Gln Lys Gln Phe Ala
            355                 360                 365

Glu Ala Met Ser His Arg Leu His Leu Asp Asn Ser Met Ala Leu Val
        370                 375                 380

Gly Lys Leu Leu Phe Gly Ile Lys Lys Gly Pro Glu Val Leu Lys Arg
385                 390                 395                 400

Val Arg Ser Asp Gly Gln Leu Leu Val Asp Asp Trp Ala Cys Leu Lys
                405                 410                 415

Ser Phe Val Arg Thr Phe Glu Thr His Cys Gly Ser Leu Ser Gln Tyr
                420                 425                 430

Gly Met Lys His Met Arg Ser Phe Ala Asn Ile Cys Asn Ala Gly Ile
            435                 440                 445

Lys Val Glu Gln Met Val Glu Ala Ser Ser Gln Ala Cys Pro Ser Val
        450                 455                 460

Pro Ser Asn Thr Trp Ser Ser Leu His Arg Gly Phe Ser Ala
465                 470                 475
```

```
<210> SEQ ID NO 85
<211> LENGTH: 475
<212> TYPE: PRT
<213> ORGANISM: Cannavalia ensiformis

<400> SEQUENCE: 85
```

```
Met Val Met Met Leu Val Met Leu Ser Leu His Gly Thr Ala Ala Arg
1               5                   10                  15

Leu Asn Arg Arg Glu Trp Asp Ser Val Ile Gln Leu Pro Thr Glu Pro
                20                  25                  30

Val Asp Asp Glu Val Gly Thr Arg Trp Ala Val Leu Val Ala Gly Ser
        35                  40                  45

Asn Gly Tyr Gly Asn Tyr Arg His Gln Ala Asp Val Cys His Ala Tyr
    50                  55                  60

Gln Leu Leu Ile Lys Gly Gly Val Lys Glu Glu Asn Ile Val Val Phe
65                  70                  75                  80

Met Tyr Asp Asp Ile Ala Tyr Asn Ala Met Asn Pro Arg Pro Gly Val
                85                  90                  95

Ile Ile Asn His Pro Gln Gly Pro Asp Val Tyr Ala Gly Val Pro Lys
                100                 105                 110

Asp Tyr Thr Gly Glu Asp Val Thr Pro Glu Asn Leu Tyr Ala Val Ile
            115                 120                 125

Leu Gly Asp Lys Ser Lys Val Lys Gly Gly Ser Gly Lys Val Ile Asn
        130                 135                 140

Ser Asn Pro Glu Asp Arg Ile Phe Ile Phe Tyr Ser Asp His Gly Gly
145                 150                 155                 160

Pro Gly Val Leu Gly Met Pro Asn Ala Pro Phe Val Tyr Ala Met Asp
                165                 170                 175

Phe Ile Asp Val Leu Lys Lys Lys His Ala Ser Gly Gly Tyr Lys Glu
                180                 185                 190
```

```
Met Val Ile Tyr Ile Glu Ala Cys Glu Ser Gly Ser Ile Phe Glu Gly
        195                 200                 205

Ile Met Pro Lys Asp Leu Asn Ile Tyr Val Thr Thr Ala Ser Asn Ala
        210                 215                 220

Gln Glu Asn Ser Phe Gly Thr Tyr Cys Pro Gly Met Asn Pro Pro Pro
225                 230                 235                 240

Pro Glu Glu Tyr Val Thr Cys Leu Gly Asp Leu Tyr Ser Val Ser Trp
                245                 250                 255

Met Glu Asp Ser Glu Thr His Asn Leu Lys Arg Glu Thr Val Gln Gln
        260                 265                 270

Gln Tyr Gln Ser Val Arg Lys Arg Thr Ser Asn Ser Asn Ser Tyr Arg
        275                 280                 285

Phe Gly Ser His Val Met Gln Tyr Gly Asp Thr Asn Ile Thr Ala Glu
        290                 295                 300

Lys Leu Tyr Leu Tyr His Gly Phe Asp Pro Ala Thr Val Asn Phe Pro
305                 310                 315                 320

Pro His Asn Gly Asn Leu Glu Ala Lys Met Glu Val Val Asn Gln Arg
                325                 330                 335

Asp Ala Glu Leu Leu Phe Met Trp Gln Met Tyr Gln Arg Ser Asn His
        340                 345                 350

Gln Pro Glu Lys Lys Thr His Ile Leu Glu Gln Ile Thr Glu Thr Val
        355                 360                 365

Lys His Arg Asn His Leu Asp Gly Ser Val Glu Leu Ile Gly Val Leu
        370                 375                 380

Leu Tyr Gly Pro Gly Lys Ser Ser Ser Val Leu His Ser Val Arg Ala
385                 390                 395                 400

Pro Gly Leu Pro Leu Val Asp Asp Trp Thr Cys Leu Lys Ser Met Val
                405                 410                 415

Arg Val Phe Glu Thr His Cys Gly Ser Leu Thr Gln Tyr Gly Met Lys
        420                 425                 430

His Met Arg Ala Phe Gly Asn Val Cys Asn Ser Gly Val Ser Lys Ala
        435                 440                 445

Ser Met Glu Glu Ala Cys Lys Ala Ala Cys Gly Gly Tyr Asp Ala Gly
        450                 455                 460

Leu Leu Tyr Pro Ser Asn Thr Gly Tyr Ser Ala
465                 470                 475

<210> SEQ ID NO 86
<211> LENGTH: 491
<212> TYPE: PRT
<213> ORGANISM: Helianthus annuus

<400> SEQUENCE: 86

Met Val Ser Arg Ile Ile Cys Phe Thr Leu Val Leu Val Thr Val Val
1               5                   10                  15

Ala Leu Ser Tyr Gly Ala Ala Gly Arg Glu Ser Ser Gly Gly Gln Lys
                20                  25                  30

Trp Arg Trp Gly Trp Asp Pro Leu Ile Arg Ser Pro Val Asp Ala Glu
        35                  40                  45

Gln Glu Val Asp Glu Gln Met Thr Asn Gly Thr Lys Trp Ala Val Leu
        50                  55                  60

Val Ala Gly Ser Lys Gly Tyr Gly Asn Tyr Arg His Gln Ala Asp Val
65                  70                  75                  80
```

-continued

```
Cys His Ala Tyr Gln Val Leu Lys Lys Gly Gly Leu Lys Asp Glu Asn
                85                  90                  95

Ile Val Val Phe Met Tyr Asp Asp Ile Ala Lys Ser Glu Met Asn Pro
                100                 105                 110

Arg Pro Gly Ile Ile Ile Asn Ser Pro Lys Gly Glu Asp Val Tyr Ala
                115                 120                 125

Gly Val Pro Lys Asp Tyr Thr Gly Lys Asn Val Thr Val Asp Asn Leu
            130                 135                 140

Ser Ala Val Leu Leu Gly Asp Arg Ser Ala Val Lys Gly Gly Ser Gly
145                 150                 155                 160

Lys Val Val Asp Ser Lys Pro Glu Asp Arg Ile Phe Leu Phe Tyr Ser
                165                 170                 175

Asp His Gly Gly Pro Gly Val Leu Gly Met Pro Asn Glu Pro His Leu
            180                 185                 190

Val Ala Lys Asp Leu Val Asp Val Leu Lys Lys Lys His Ala Met Gly
            195                 200                 205

Thr Tyr Lys Glu Met Val Ile Tyr Leu Glu Ala Cys Glu Ser Gly Ser
        210                 215                 220

Ile Phe Glu Gly Ile Leu Pro Glu Asp Leu Asn Ile Tyr Ala Thr Thr
225                 230                 235                 240

Ala Ser Gly Ala Gln Glu Asn Ser Tyr Gly Thr Tyr Cys Pro Gly Thr
                245                 250                 255

Glu Pro Ser Pro Pro Pro Glu Tyr Ile Thr Cys Leu Gly Asp Leu Tyr
                260                 265                 270

Ser Val Ala Trp Met Glu Asp Ser Glu Thr His Asn Leu Lys Lys Glu
            275                 280                 285

Ser Leu Glu Gln Gln Phe Asn Lys Val Lys Lys Arg Thr Ser Asn Ser
        290                 295                 300

Asn Thr Tyr Asn Thr Gly Ser His Val Met Glu Tyr Gly Ser Lys Asp
305                 310                 315                 320

Ile Lys Pro Glu Lys Val Tyr Leu Tyr Leu Gly Phe Asp Pro Ala Thr
                325                 330                 335

Val Asn Leu Pro Ala Asn Gln Ile His Phe Asp Lys Leu Asp Gly Val
            340                 345                 350

Asn Gln Arg Asp Ala Asp Leu Ile Phe Leu Trp Gln Arg Tyr Lys Lys
        355                 360                 365

Ser Ser Glu Ser Thr Arg Pro Glu Ile Leu Arg Glu Ile Thr Glu Thr
    370                 375                 380

Leu Thr His Arg Gly His Leu Asp Ser Ser Ile Asp Met Ile Gly Val
385                 390                 395                 400

Leu Leu Phe Gly Pro Gln Asn Gly Arg Ser Thr Leu His Ser Ala Arg
                405                 410                 415

Ala Pro Gly Leu Pro Leu Val Asp Asp Trp Glu Cys Phe Lys Ser Thr
            420                 425                 430

Ala Arg Leu Phe Glu Lys His Cys Gly Leu Leu Thr Gln Tyr Gly Met
        435                 440                 445

Lys His Met Arg Ala Phe Ala Asn Ile Cys Asn Ser Ser Val Glu Lys
    450                 455                 460

Ser Lys Val Glu Glu Val Phe Ile Ala Thr Cys Gly Gly Lys Asn Ile
465                 470                 475                 480

Gly Pro Tyr Gly Thr Phe Gly Ala Tyr Ser Val
                485                 490
```

-continued

```
<210> SEQ ID NO 87
<211> LENGTH: 494
<212> TYPE: PRT
<213> ORGANISM: Arabidopsis thaliana

<400> SEQUENCE: 87

Met Ala Thr Thr Met Thr Arg Val Ser Val Gly Val Val Leu Phe Val
1               5                   10                  15

Leu Leu Val Ser Leu Val Ala Val Ser Ala Ala Arg Ser Gly Pro Asp
                20                  25                  30

Asp Val Ile Lys Leu Pro Ser Gln Ala Ser Arg Phe Phe Arg Pro Ala
            35                  40                  45

Glu Asn Asp Asp Asp Ser Asn Ser Gly Thr Arg Trp Ala Val Leu Val
        50                  55                  60

Ala Gly Ser Ser Gly Tyr Trp Asn Tyr Arg His Gln Ala Asp Ile Cys
65                  70                  75                  80

His Ala Tyr Gln Leu Leu Arg Lys Gly Gly Leu Lys Glu Glu Asn Ile
                85                  90                  95

Val Val Phe Met Tyr Asp Asp Ile Ala Asn Asn Tyr Glu Asn Pro Arg
                100                 105                 110

Pro Gly Thr Ile Ile Asn Ser Pro His Gly Lys Asp Val Tyr Gln Gly
            115                 120                 125

Val Pro Lys Asp Tyr Thr Gly Asp Asp Val Asn Val Asp Asn Leu Phe
        130                 135                 140

Ala Val Ile Leu Gly Asp Lys Thr Ala Val Lys Gly Gly Ser Gly Lys
145                 150                 155                 160

Val Val Asp Ser Gly Pro Asn Asp His Ile Phe Ile Phe Tyr Ser Asp
                165                 170                 175

His Gly Gly Pro Gly Val Leu Gly Met Pro Thr Ser Pro Tyr Leu Tyr
            180                 185                 190

Ala Asn Asp Leu Asn Asp Val Leu Lys Lys Lys His Ala Leu Gly Thr
            195                 200                 205

Tyr Lys Ser Leu Val Phe Tyr Leu Glu Ala Cys Glu Ser Gly Ser Ile
        210                 215                 220

Phe Glu Gly Leu Leu Pro Glu Gly Leu Asn Ile Tyr Ala Thr Thr Ala
225                 230                 235                 240

Ser Asn Ala Glu Glu Ser Ser Trp Gly Thr Tyr Cys Pro Gly Glu Glu
                245                 250                 255

Pro Ser Pro Pro Pro Glu Tyr Glu Thr Cys Leu Gly Asp Leu Tyr Ser
            260                 265                 270

Val Ala Trp Met Glu Asp Ser Gly Met His Asn Leu Gln Thr Glu Thr
        275                 280                 285

Leu His Gln Gln Tyr Glu Leu Val Lys Arg Arg Thr Ala Pro Val Gly
        290                 295                 300

Tyr Ser Tyr Gly Ser His Val Met Gln Tyr Gly Asp Val Gly Ile Ser
305                 310                 315                 320

Lys Asp Asn Leu Asp Leu Tyr Met Gly Thr Asn Pro Ala Asn Asp Asn
                325                 330                 335

Phe Thr Phe Ala Asp Ala Asn Ser Leu Lys Pro Pro Ser Arg Val Thr
            340                 345                 350

Asn Gln Arg Asp Ala Asp Leu Val His Phe Trp Glu Lys Tyr Arg Lys
        355                 360                 365

Ala Pro Glu Gly Ser Ala Arg Lys Thr Glu Ala Gln Lys Gln Val Leu
        370                 375                 380
```

-continued

_____

Glu Ala Met Ser His Arg Leu His Ile Asp Asn Ser Val Ile Leu Val
385                 390                 395                 400

Gly Lys Ile Leu Phe Gly Ile Ser Arg Gly Pro Glu Val Leu Asn Lys
                405                 410                 415

Val Arg Ser Ala Gly Gln Pro Leu Val Asp Asp Trp Asn Cys Leu Lys
            420                 425                 430

Asn Gln Val Arg Ala Phe Glu Arg His Cys Gly Ser Leu Ser Gln Tyr
        435                 440                 445

Gly Ile Lys His Met Arg Ser Phe Ala Asn Ile Cys Asn Ala Gly Ile
    450                 455                 460

Gln Met Glu Gln Met Glu Glu Ala Ala Ser Gln Ala Cys Thr Thr Leu
465                 470                 475                 480

Pro Thr Gly Pro Trp Ser Ser Leu Asn Arg Gly Phe Ser Ala
                485                 490

<210> SEQ ID NO 88
<211> LENGTH: 482
<212> TYPE: PRT
<213> ORGANISM: Clitoria ternatea

<400> SEQUENCE: 88

Met Lys Asn Pro Leu Ala Ile Leu Phe Leu Ile Ala Thr Val Val Ala
1               5                   10                  15

Val Val Ser Gly Ile Arg Asp Asp Phe Leu Arg Leu Pro Ser Gln Ala
            20                  25                  30

Ser Lys Phe Phe Gln Ala Asp Asp Asn Val Glu Gly Thr Arg Trp Ala
        35                  40                  45

Val Leu Val Ala Gly Ser Lys Gly Tyr Val Asn Tyr Arg His Gln Ala
    50                  55                  60

Asp Val Cys His Ala Tyr Gln Ile Leu Lys Lys Gly Gly Leu Lys Asp
65                  70                  75                  80

Glu Asn Ile Ile Val Phe Met Tyr Asp Asp Ile Ala Tyr Asn Glu Ser
                85                  90                  95

Asn Pro His Pro Gly Val Ile Ile Asn His Pro Tyr Gly Ser Asp Val
            100                 105                 110

Tyr Lys Gly Val Pro Lys Asp Tyr Val Gly Glu Asp Ile Asn Pro Pro
        115                 120                 125

Asn Phe Tyr Ala Val Leu Leu Ala Asn Lys Ser Ala Leu Thr Gly Thr
    130                 135                 140

Gly Ser Gly Lys Val Leu Asp Ser Gly Pro Asn Asp His Val Phe Ile
145                 150                 155                 160

Tyr Tyr Thr Asp His Gly Gly Ala Gly Val Leu Gly Met Pro Ser Lys
                165                 170                 175

Pro Tyr Ile Ala Ala Ser Asp Leu Asn Asp Val Leu Lys Lys Lys His
            180                 185                 190

Ala Ser Gly Thr Tyr Lys Ser Ile Val Phe Tyr Val Glu Ser Cys Glu
        195                 200                 205

Ser Gly Ser Met Phe Asp Gly Leu Leu Pro Glu Asp His Asn Ile Tyr
    210                 215                 220

-continued

```
Val Met Gly Ala Ser Asp Thr Gly Glu Ser Ser Trp Val Thr Tyr Cys
225             230             235             240

Pro Leu Gln His Pro Ser Pro Pro Pro Glu Tyr Asp Val Cys Val Gly
            245             250             255

Asp Leu Phe Ser Val Ala Trp Leu Glu Asp Cys Asp Val His Asn Leu
            260             265             270

Gln Thr Glu Thr Phe Gln Gln Gln Tyr Glu Val Val Lys Asn Lys Thr
            275             280             285

Ile Val Ala Leu Ile Glu Asp Gly Thr His Val Val Gln Tyr Gly Asp
    290             295             300

Val Gly Leu Ser Lys Gln Thr Leu Phe Val Tyr Met Gly Thr Asp Pro
305             310             315             320

Ala Asn Asp Asn Asn Thr Phe Thr Asp Lys Asn Ser Leu Gly Thr Pro
            325             330             335

Arg Lys Ala Val Ser Gln Arg Asp Ala Asp Leu Ile His Tyr Trp Glu
            340             345             350

Lys Tyr Arg Arg Ala Pro Glu Gly Ser Ser Arg Lys Ala Glu Ala Lys
            355             360             365

Lys Gln Leu Arg Glu Val Met Ala His Arg Met His Ile Asp Asn Ser
    370             375             380

Val Lys His Ile Gly Lys Leu Leu Phe Gly Ile Glu Lys Gly His Lys
385             390             395             400

Met Leu Asn Asn Val Arg Pro Ala Gly Leu Pro Val Val Asp Asp Trp
            405             410             415

Asp Cys Phe Lys Thr Leu Ile Arg Thr Phe Glu Thr His Cys Gly Ser
            420             425             430

Leu Ser Glu Tyr Gly Met Lys His Met Arg Ser Phe Ala Asn Leu Cys
            435             440             445

Asn Ala Gly Ile Arg Lys Glu Gln Met Ala Glu Ala Ser Ala Gln Ala
    450             455             460

Cys Val Ser Ile Pro Asp Asn Pro Trp Ser Ser Leu His Ala Gly Phe
465             470             475             480

Ser Val
```

ASX-SPECIFIC PROTEIN LIGASES AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_587USPC_SEQUENCE_LISTING.txt. The text file is 113 KB, was created on Nov. 2, 2021, and is being submitted electronically via EFS-Web.

CROSS-REFERENCE TO RELATED APPLICATIONS

This application is the United States national phase of international Application No. PCT/SG2020/050267 filed May 6, 2020, and claims priority to Singapore patent application Ser. No. 10201904085W filed May 7, 2019, and Singapore patent application Ser. No. 10/201,910861S filed Nov. 19, 2019, the contents of which being hereby incorporated by reference in its entirety for all purposes.

FIELD OF THE INVENTION

The present invention lies in the technical field of enzyme technology and specifically relates to enzymes having Asx-specific ligase and cyclase activity and to nucleic acids encoding those as well as methods of the manufacture of said enzymes. Further encompassed are methods and uses of these enzymes.

BACKGROUND OF THE INVENTION

Head-to-tail macrocyclization of peptides and proteins has been used as a strategy to constrain structures and enhance metabolic stability against proteolytic degradation. In addition, a constrained macrocyclic conformation may also improve pharmacological activity and oral bioavailability. Although most peptides and proteins are produced as linear chains, circular peptides ranging from 6 to 78 residues occur naturally in diverse organisms. These cyclic peptides usually display high resistance to heat denaturation and proteolysis and have inspired a new trend in protein engineering, as demonstrated by recent successes in the cyclization of cytokines, histatin, ubiquitin C-terminal hydrolase, conotoxin and bradykinin-grafted cyclotides. Furthermore, cyclic peptides have been used as therapeutics, including valinomycin, gramicidin S and cyclosporine.

To date chemical methods are typically used for the cyclization of peptides. One possible strategy is native chemical ligation. This method requires an N-terminal cysteine and a C-terminal thioester, requirements that limit its application for non-cysteine-containing peptides. Furthermore, chemical methods are not always feasible, especially for large peptides and proteins.

Although enzymatic methods employing a naturally-occurring cyclase would be ideal, currently only very few peptide cyclases are known and they are for various reasons not fully exploited.

Recent discovery of a novel cyclase, butelase-1, from cyclotide-producing plant *Clitoria ternatea* proved that a unique type of asparaginyl endopeptidase (AEP) is the processing enzyme to cyclize the linear precursors of cyclotides (Nguyen G K T, et al. (2014) Nat Chem Biol 10(9):732-738). AEPs (or legumains) are cysteine proteases belonging the subfamily C13 (EC 3.4.22.34) under clan CD. Compared to AEPs which are hydrolases, butelase-1 reverses the enzymatic direction of AEPs and strongly promotes aminolysis to catalyze peptide-bond formation. Bioassays show that butelase-1 is not only a cyclase but also an efficient peptide ligase that can ligate biomolecules by forming peptide bond between Asn/Asp and any amino acids except Pro with the highest reported catalytic efficiency to date of 1,340,000 $M^{-1}s^{-1}$. Butelase-1 is a versatile protein engineering tool for protein and peptide ligation, modification, cyclization, tagging, and live cell labeling and has been described in detail, including its uses, in international patent application WO 2015/163818 A1. Such butelase-1 like peptide ligases, designated as peptide asparaginyl ligases (PALs), are useful biochemical and biotechnological tools for linkage-specific and site-specific protein modifications and precision biomanufacturing of biotherapeutics such as antibody-drug conjugates.

AEPs and PALs are expressed as proenzymes, generally consisting a ~10-kDa pro-domain, an active ~32-kDa core domain formed by six β-strands surrounded by five α-helices, and a 15-kDa C-terminal cap domain formed by six tightly-bound helices. Both AEPs and PALs display intrinsic protease activity at acidic pH for autolytic maturation. Their biosynthetic processing is similar, involving an autolytic activation in the acidic subcellular compartments such as lysosomes and lytic vacuoles. In vitro, activations are usually performed at pH 4 to 5. A major structural change after the acidic activation is the cleavage and dissociation of the C-terminal cap domain, and which exposes the catalytic site in the core domain. Religation of cap and core domains is reported at near neutral pH when both domains remain intact and in close proximity after cleavage.

Plant AEPs play important roles in protein degradation, maturation, programmed cell death, and host defense via their proteolytic activity triggered in the acidic environment of vacuoles. AEPs, such as butelase 2, OaAEP2 and HaAEP1 (sunflower *Helianthus annuus*) display predominantly protease activity even at neutral pH, with a very low level of ligase activity. Certain AEPs catalyze both ligation and hydrolysis products from peptide substrates carrying AEP-recognition signals at near neutral pH (6-7.5). Very rarely, AEPs mediate peptide splicing including both peptide bond breaking and formation, such as in the maturation of concanavalin A, by mediating circular permutation. In contrast to these "bi-functional" or "predominant" AEPs, PALs like butelase 1 and OaAEP1b catalyze the formation of ligation products essentially devoid of any hydrolytic product at near neutral pH, and their ligase activity is preponderant even under mild acidic conditions (pH <6).

Currently, only a handful of such PALs have been identified. They include the prototypic PAL butelase-1, as well subsequent discoveries butelase-1 like enzymes, OaAEP1 b (Harris K S, et al. (2015) Nat Commun 6(1):10199) and HeAEP3 (Jackson M A, et al. (2018) Nat Commun 9(1): 241123) identified from other cyclotide-producing plants *Oldenlandia affinis* and *Hybanthus enneaspermus*, respectively.

To date, the molecular mechanisms differentiating AEPs and PALs are not known. Despite the publication of several plant AEP crystal structures, including both proenzymes and active form, the structural determinants that underpin their nature as protease or ligase are still unresolved. Enzymes from both extremes share the same structure with r.m.s.d<1 Å (e.g. OaAEP1b and HaAEP1).

Since ligase/cyclase activity is highly desirable and there is need in the art for novel ligases/cyclases that can be reliably used as molecular tools for peptide ligation and cyclization, it would be helpful to identify the determinants that control enzyme directionality of PALs and AEPs, as this would provide opportunities for deliberately tailoring these enzymes for specific needs.

SUMMARY OF THE INVENTION

The inventors of the present invention found that the enzymatic activity of AEPs and PALs is controlled by subtle differences at key positions near the catalytic center. These local alterations control the access to the S-acyl enzyme intermediate of water molecules (leading to hydrolysis) or of incoming nucleophiles (leading to ligation). By studying a series of putative AEPs and PALs from two cyclotide-producing plants *Viola yedoensis* (var. *phillipica*) and *Viola canadensis* and using the recombinant enzymes to investigate the molecular mechanisms responsible for ligase catalytic activity, two putative Ligase Activity Determinants (LADs) could be identified and validated by structural comparison, MD simulation and site-directed mutagenesis. These results explain the molecular mechanism allowing the conversion of AEPs into PALs and provide a useful tool for the discovery and engineering of new ligases. In the course of these studies, further useful PALs were identified that allow efficient recombinant expression and show high cyclization activities.

In a first aspect, the present invention thus relates to an isolated polypeptide having protein ligase, preferably cyclase, activity comprising or consisting of (i) the amino acid sequence as set forth in SEQ ID NO:1;

(ii) an amino acid sequence that shares at least 60, preferably at least 70, more preferably at least 80, most preferably at least 90% sequence identity with the amino acid sequence set forth in SEQ ID NO:1 over its entire length;

(iii) an amino acid sequence that shares at least 80, preferably at least 90, more preferably at least 95% sequence homology with the amino acid sequence set forth in SEQ ID NO:1 over its entire length; or (iv) a fragment of any one of (i)-(iii).

The polypeptide consisting of SEQ ID NO:1 is also referred to herein as "VyPAL2" or "VyPAL2 active form/domain".

In another aspect, the present invention also relates to nucleic acid molecules encoding the polypeptides described herein, as well as a vector containing such a nucleic acid, in particular a copying vector or an expression vector.

In a further aspect, the invention is also directed to a host cell, preferably a non-human host cell, containing a nucleic acid as contemplated herein or a vector as contemplated herein. The host cell may be an insect cell, such as a Sf9 (*Spodoptera frugiperda*) cell.

A still further aspect of the invention is a method for manufacturing a polypeptide as described herein, comprising culturing a host cell contemplated herein; and isolating the polypeptide from the culture medium or from the host cell.

In a still further aspect, the present invention relates to the use of polypeptides described herein for protein ligation, in particular for cyclizing one or more peptide(s).

In still another aspect, the invention relates to a method for cyclizing a peptide, the method comprising incubating said peptide with the polypeptides described above in connection with the inventive uses under conditions that allow cyclization of said peptide.

In a still further aspect, the invention relates to a method for ligating at least two peptides, the method comprising incubating said peptides with the polypeptides described above in connection with the inventive uses under conditions that allow ligation of said peptides.

In another aspect, the invention relates to a solid support material onto which the isolated polypeptides of the invention are immobilized as well as the use thereof and methods that use such substrates.

In another aspect, the invention also encompasses a transgenic organism, such as a plant, comprising a nucleic acid molecule encoding a polypeptide having protein ligase and/or cyclase activity as described herein. The polypeptide is preferably not naturally present in said organism. Accordingly, the present invention also features transgenic organisms, preferably plants, that express a heterologous polypeptide according to the invention.

In still another aspect, the invention also encompasses a method for increasing the protein ligase activity of a polypeptide having asparaginyl endopeptidase (AEP) activity, the method comprising the steps of substituting the amino acid residue at the position corresponding to position 126 of SEQ ID NO:1 with either an A or a G residue. In these embodiments, the amino acid residue at the position corresponding to position 127 of SEQ ID NO:1 may be selected such that the sequence at positions 126/127 is either GA or AP or AA, preferably GA or AP. If the amino acid at the position corresponding to position 126 of SEQ ID NO:1 is G, it is preferred that the amino acid at the position corresponding to position 127 of SEQ ID NO:1 is not P.

In a still further aspect, the invention is also directed to a method for producing a polypeptide having protein ligase activity, the method comprising:

(i) providing a polypeptide having asparaginyl endopeptidase (AEP) activity; and (ii) introducing one or more amino acid substitutions into the polypeptide having asparaginyl endopeptidase (AEP) activity, wherein said substitutions comprise substituting the amino acid residue at the position corresponding to position 126 of SEQ ID NO:1 with an A or a G residue and optionally substituting the amino acid residue at the position corresponding to position 127 of SEQ ID NO:1 with either a P or an A residue, such that the amino acid sequence in the positions corresponding to positions 126/127 in SEQ ID NO:1 is either GA, AA or AP, preferably GA or AP.

HeAEP3=SEQ ID NO:83; PxAEP3b=SEQ ID NO:84; CeAEP=SEQ ID NO:85; HaAEP1=SEQ ID NO:86; AtLEGy=SEQ ID NO:87).

FIG. 7 shows the immobilization of PALs, butelase-1 and VyPAL2, by non-covalent affinity binding or covalent attachment. (A) Affinity binding of glycosylated PALs with concanavalin A (ConA) agarose beads to give ConA-PAL 1 and ConA-Vy2 2. (B) Affinity binding of biotinylated PALs with NeutrAvidin agarose beads to give NA-Bu1(b) 3 and NA-Vy2(b) 4. Biotinylated PALs were prepared by coupling of succinimidyl-6-(biotinamido)hexanoate (NHS-LC-biotin) to the amino groups of PALs. (C) Covalent attachment of PALs with active NHS-ester on agarose beads to give agarose-Bu1 5 and agarose-Vy2 6. The distance between enzymes and the agarose beads are calculated by the sizes of the spacer moieties and the pre-coupled affinity binding ligands.

FIG. 8 shows peptide macrocyclization by immobilized PAL beads. For each reaction, 1 μM of immobilized PALs calculated based on their protein loading was mixed with 0.2 mM KN14-GL (SEQ ID NO:51). The reactions were performed at pH 6.5 at room temperature with gentle rocking for 5 min. Products were eluted out from the spin column and analyzed with MALDI-TOF MS. KN14-GL 7 (calc. mass 1659.4 Da, obs. Mass 1660.0 Da). cKN14 8 (calc. mass 1471.3 Da, obs. Mass 1471.9 Da).

Figure 9:
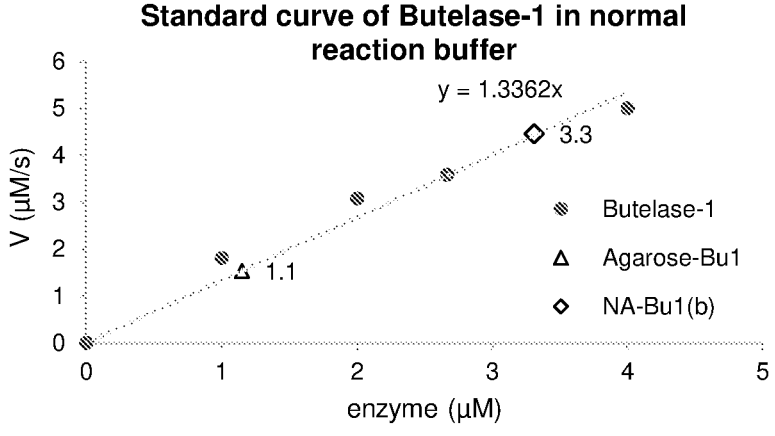
Figure 9:
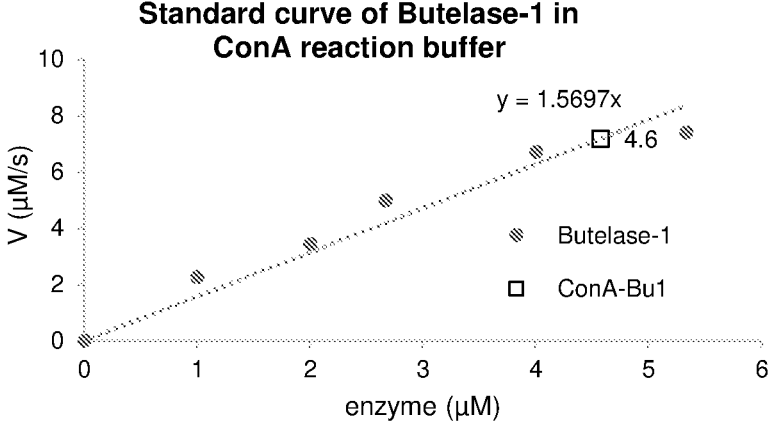
Figure 9:
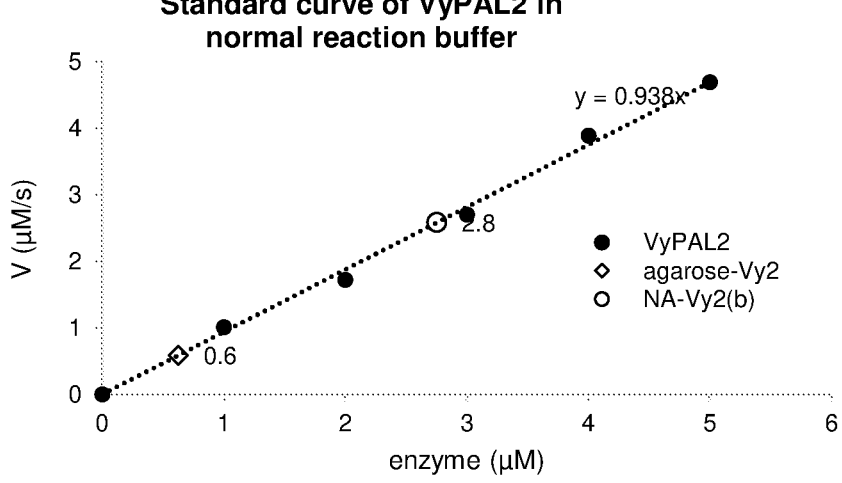

FIG. 9 shows the determination of efficiency of immobilized butelase-1 and VyPAL2 by comparing with the standard activity curves of their soluble forms. Free enzyme concentration used was ranged from 1 to 8 nM. Reaction rate (V) was calculated by amount of product cKN14 (per second. Normal reaction buffer refers to the 20 mM sodium phosphate buffer (pH 6.5) containing 1 mM DTT, and 0.1 M NaCl. ConA reaction buffer refers to the reaction buffer with additional 5 mM $CaCl_2$) and 5 mM MgCl2.

Figure 10:
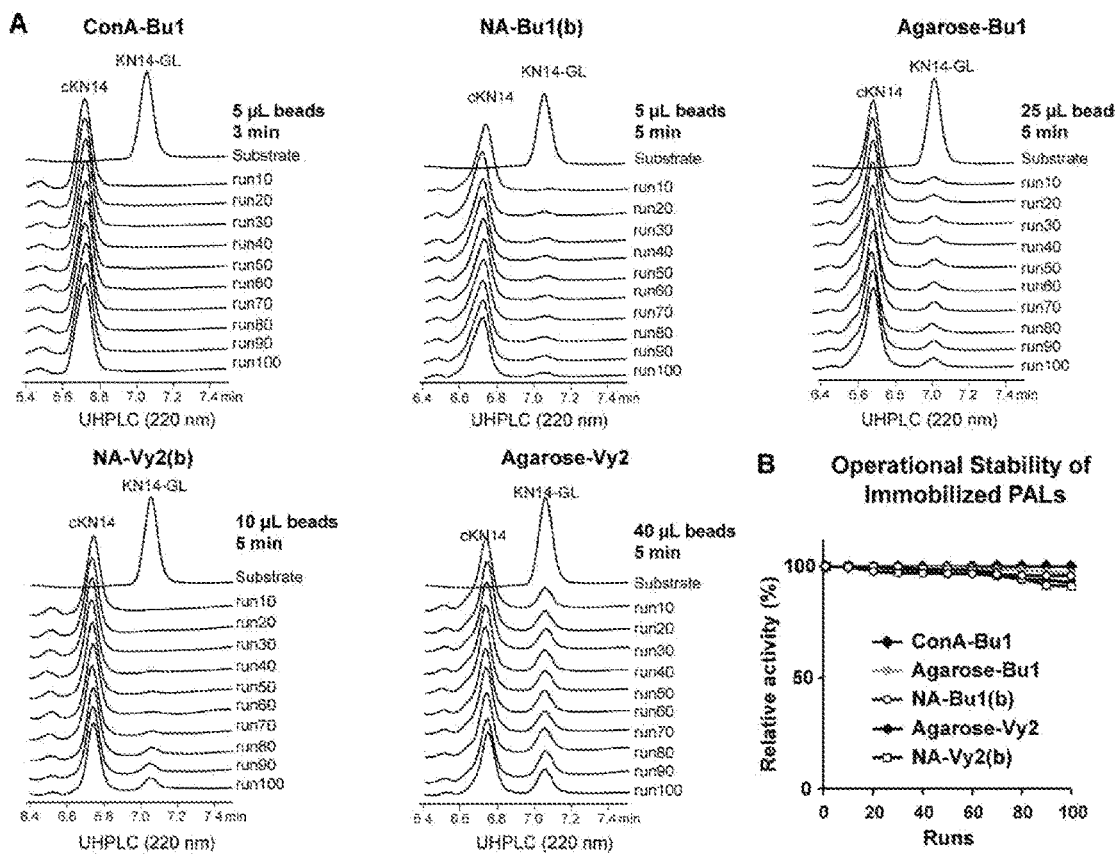

FIG. 10 shows operational stability of immobilized PALs. (A) RP-HPLC monitoring of cyclization of KN14-GL into cKN14 by five immobilized PALs 1, 3-6 in 100 repeated reactions. For each experiment, 100 μL of reaction mixture (pH 6.5) containing 0.1 mM KN14-GL (SEQ ID NO:51) was given. Amount of beads used was adjusted according to the effective concentration of each type to give the molar ratio of effective enzyme:substrate=1:350-1:600. Reaction was conducted at room temperature for 3-5 min. (B) Summary of operational stability of five immobilized PALs 1, 3-6.

Figure 11:
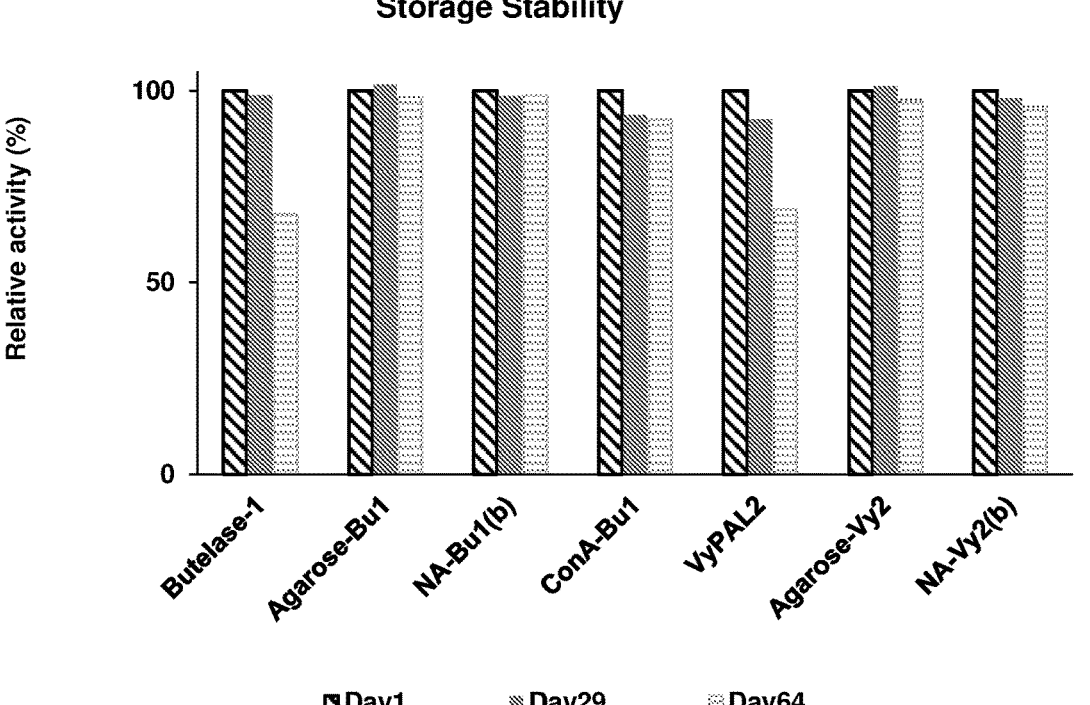

FIG. 11 shows the stability of five immobilized PALs 1, 3-6, butelase-1 and VyPAL2 after storing in 4° C. for 1, 29 and 64 days.

Figure 12:
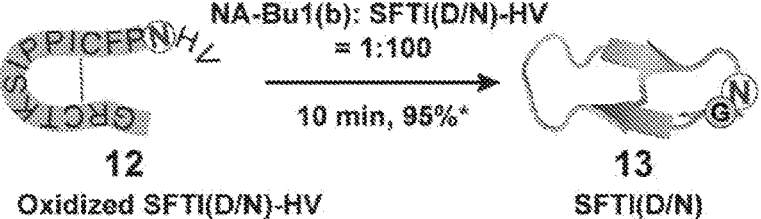
Figure 12:
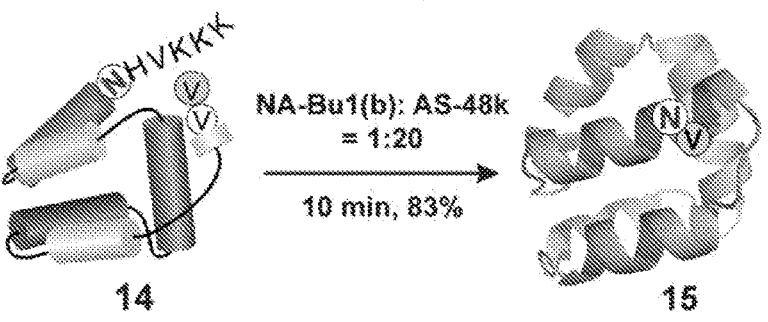
Figure 12:
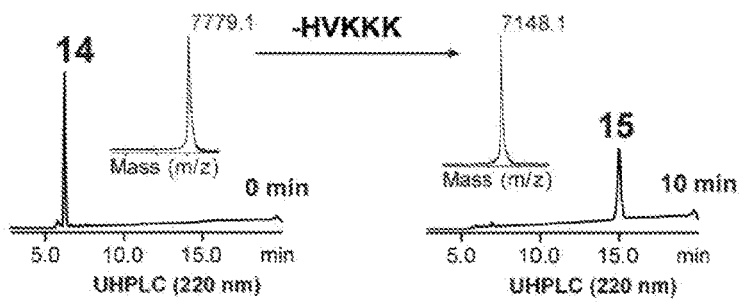

FIG. 12 shows the macrocyclization of peptides and proteins by NA-Bu1(b) 3 at pH 6.5 at room temperature for 10 min with gentle shaking. (A) Cyclization of SFTI(D/N)-HV (SEQ ID NO:54) 12 (0.1 mM, calc. mass 1767.9 Da, obs. Mass 1767.9 Da) into SFTI(D/N) 13 (calc. mass 1513.8 Da, obs. Mass 1513.3 Da) by NA-Bu1(b) 3 to give 95% crude yield (*) of cyclic SFTI(D/N) 13 as determined by MALDI-TOF MS. (B) Cyclization of the folded linear bacteriocin precursor AS-48K 14 (50 μM, calc mass 7783.5 Da, obs. Mass 7779.1 Da) by NA-Bu1(b) 3 to give cyclic AS-48 15 (calc. mass 7145.1 Da, obs. Mass 7148.1 Da) with 83% yield as determined by UHPLC.

Figure 13:
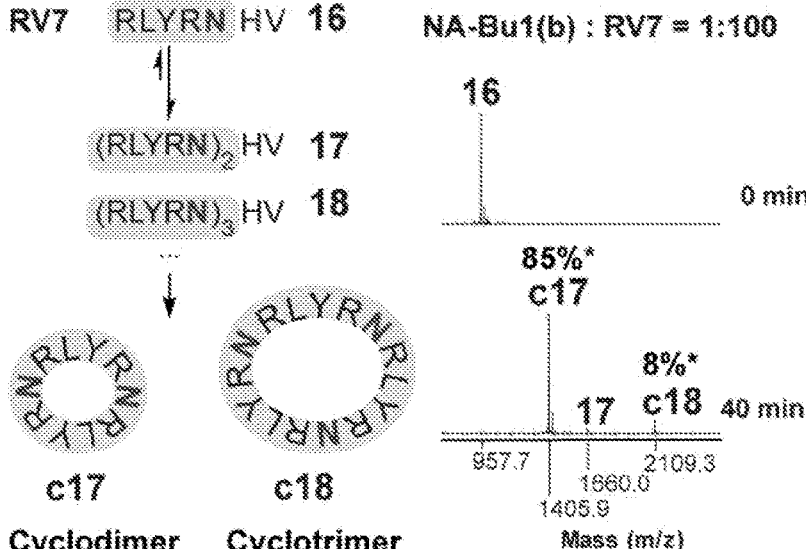

FIG. 13 shows the cyclooligomerization of peptide RV7 16 (SEQ ID NO:55; 0.2 mM, calc mass 956.5 Da, obs. Mass 957.7 Da) by NA-Bu1(b) 3 to give 85% cyclodimer c17 (calc mass 1404.8 Da, obs. Mass 1405.9 Da) and 8% cyclotrimer c18 (calc mass 2107.2 Da, obs. Mass 2109.3 Da) in 40 min.

Figure 14:
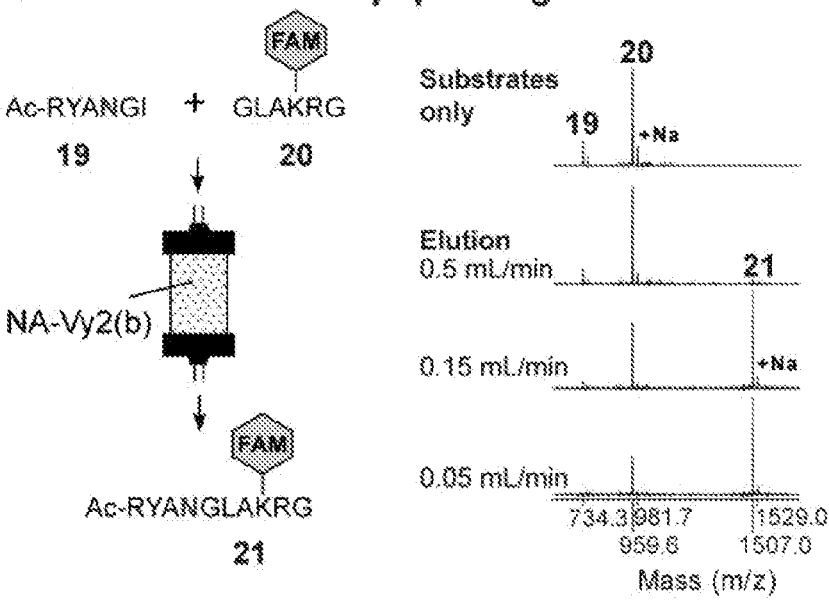
Figure 14:
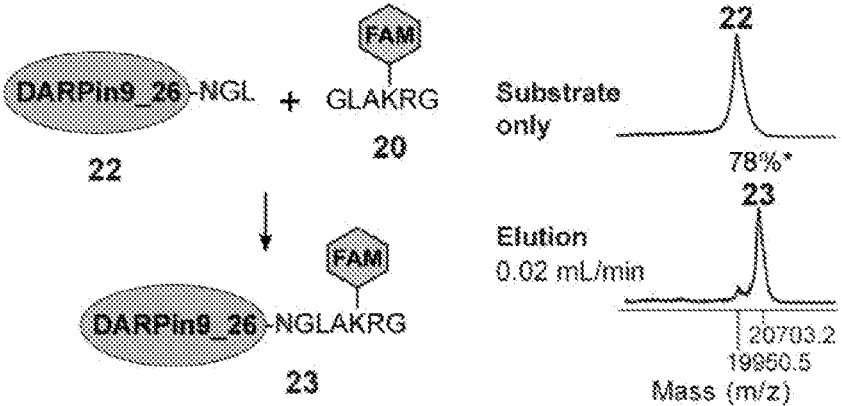

FIG. 14 shows continuous-flow peptide and protein ligation by NA-Vy2(b) 4. (A) Ligation of Ac-RYANGI 19 (calc mass 735.4 Da, obs. Mass 734.3 Da; SEQ ID NO:56) and GLAK(FAM)RG 20 (calc mass 958.7 Da, obs. Mass 959.6 Da; SEQ ID NO:57) in 1:10 molar ratio by NA-Vy2(b) 4 to yield ligation product Ac-RYANGLAK(FAM)RG 21 (calc mass 1506.0 Da, obs. Mass 1507.0 Da; SEQ KID NO:58). (B) C-terminal fluorescent labeling of recombinant protein DARPin9_26-NGL 22 (calc. mass 19968 Da, obs. mass 19950 Da; SEQ ID NO:49) by GLAK(FAM)RG 20 (SEQ ID NO:57) in 1:5 molar ratio to give fluorescent protein DAR-Pin9_26-NGLAK(FAM)RG 23 (calc. mass 20728 Da, obs. mass 20703 Da). Reaction products were analyzed by MALDI-TOF MS in the positive-ion linear-mode and the crude yield was calculated by peak area.

DETAILED DESCRIPTION

Figure 1:
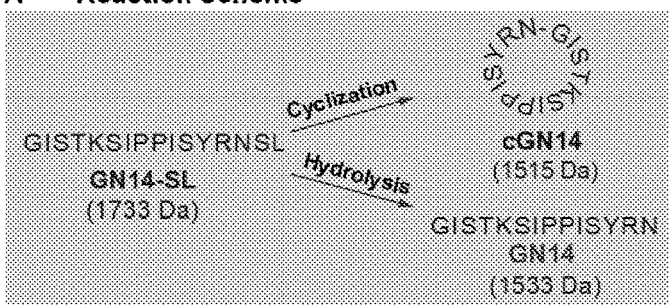
FIG. 1 shows the enzymatic activity of recombinant VyPAL1-3 and VyAEP1. (A) Reaction scheme of ligase-mediated cyclization of GN14-SL (SEQ ID NO:59). (B) Analytical HPLC and MALDI-TOF mass spectrometry data of VyPAL2-mediated cyclization under different reaction pH values. *: racemized synthetic GN14-SL. Note that MALDI-TOF MS was more sensitive against cyclic cGN14 than the linear species. (C) Quantitative summary of product ratio and reaction yield of each enzyme analyzed using RP-HPLC. For each reaction, a molar ratio of purified active enzyme:GN14-SL=1:500 was mixed and reacted at 37° C. for 10 min. Average yield and error bars were calculated from experiments performed in triplicate
Figure 1:
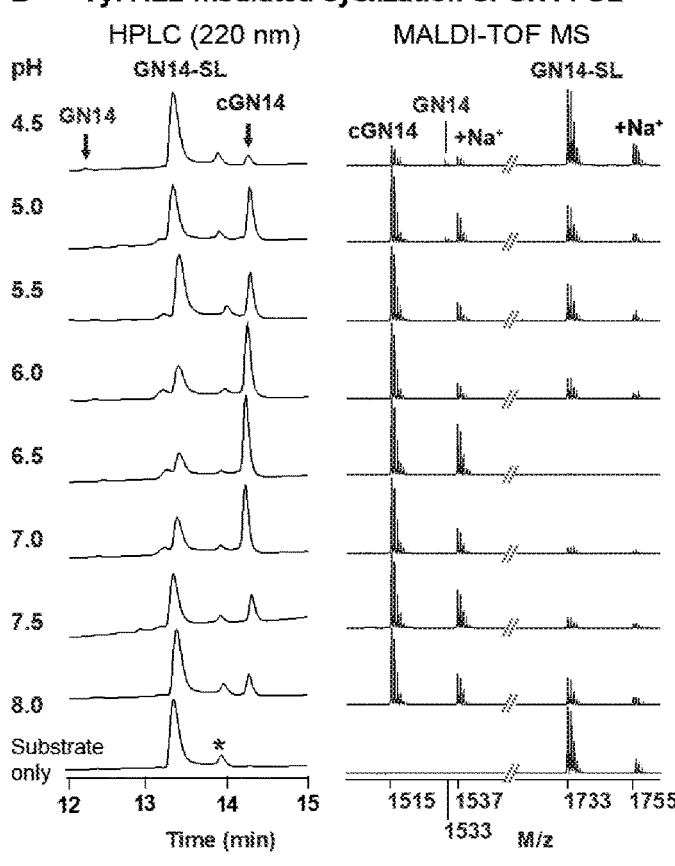
Figure 1:
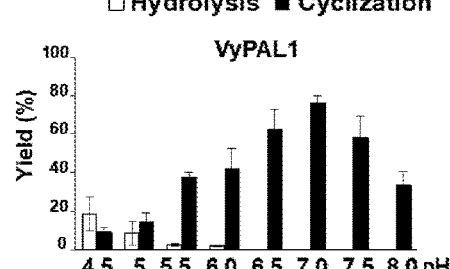
Figure 1:
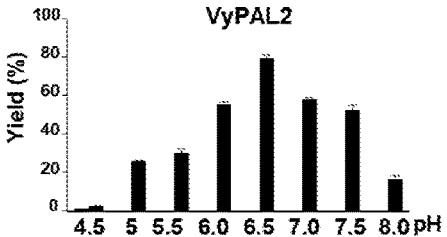
Figure 1:
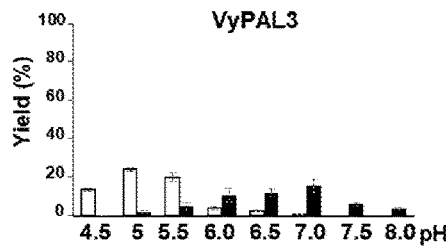
Figure 1:
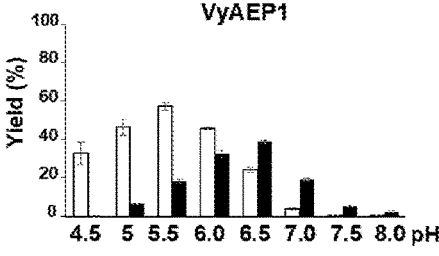

The present invention is based on the inventors' identification of novel enzymes having peptide ligase/cyclase activity isolated from *Viola yedoensis* and *Viola canadensis*. Specifically, the inventors successfully identified novel ligases from plants of the Violaceae using homology with enzymes capable of ligase activity, such as known enzyme butelase-1 (WO 2015/163818 B1). These enzymes were named peptide asparagine ligases (PALs), to highlight their specific transpeptidase activity and to differentiate them from AEPs. By purification and testing of the corresponding recombinant enzymes, it was found that solely VyPAL2 has ligase activity at a wide range of pH values ranging from 4.5 to 8.0 with the maximum catalytic rate at pH 6.5-7.0 that is only 3.5 times less efficient than butelase 1, and displays minimal hydrolase activity only at acidic pH (4.5), making it a recombinant PAL valuable for biotechnological applications. VyPAL1, despite being a good ligase, showed a promiscuous activity with some hydrolysis at acidic pH. VyPAL3 was characterized by an overall low catalytic efficiency together with a dominant hydrolysis activity at low pH. Moreover, the VyAEP1 protein, predicted to be a protease based on sequence homology, was indeed found to be a protease at low pH (FIG. 1). To reveal the molecular bases for the differences in activities between these enzymes, the crystal structure of VyPAL2 was obtained and used as a template to model the structure of VyPAL protein isoforms. These comparisons pointed to two areas surrounding the 51 active site pocket: the S2 and the S1' pockets that show subtle but critical variations between an AEP and a PAL.

Figure 5:
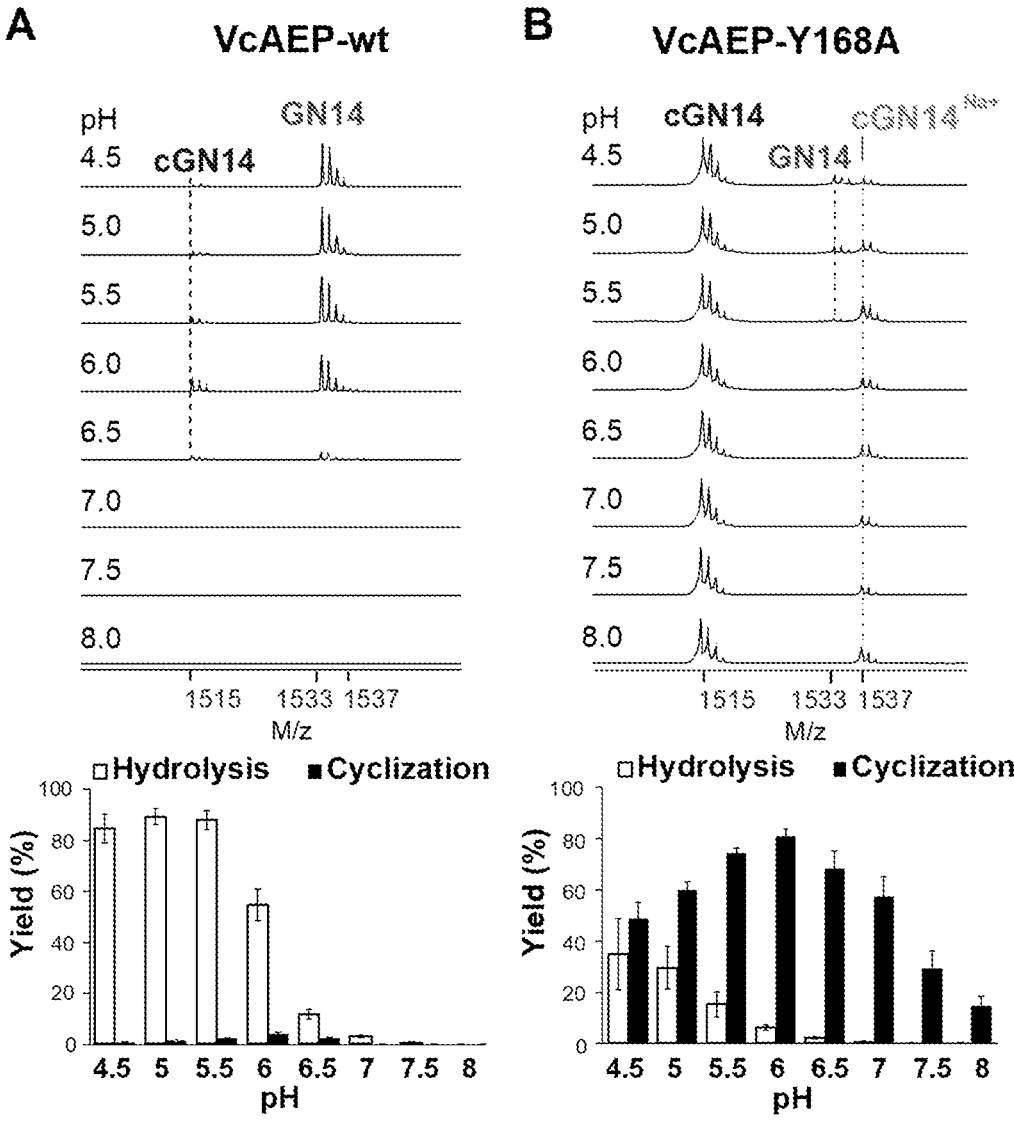
FIG. 5 shows the activity of VcAEP and the VcAEP-Y168A mutant (LAD2). MS analysis and HPLC-based quantitative summary of the reaction catalyzed by (A) VcAEP wild type and (B) VcAEP-Y168A mutant targeting the LAD2 region. All reactions were performed at pH values ranging from 4.5 to 8.0. MS peaks of the hydrolysis product GN14, cyclization product cGN14, and sodium ion adduct of cGN14 are marked with dashed-lines. A dramatic improvement of ligase activity for the VcAEP-Y168A mutant is clearly visible
Figure 6:
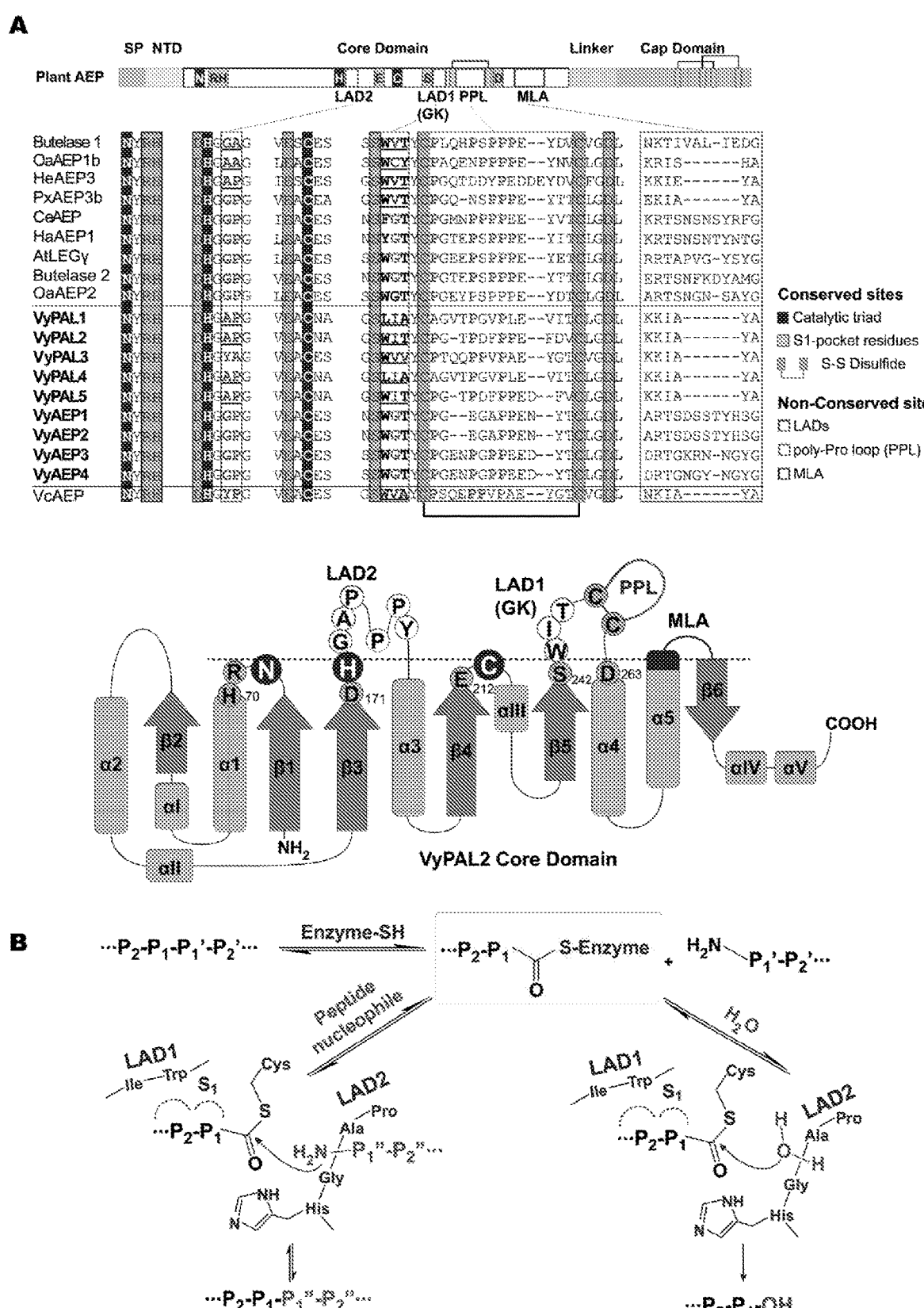
FIG. 6 shows ligase activity determinants (LADs) of PALs and the proposed catalytic mechanism. (A) Sequence alignment of PALs and AEPs studied in this work. Catalytic triad Asn-His-Cys is shaded in black. Residues belonging to the S1 pocket are shaded in blue. Proposed LAD residues are boxed in red. Residues of LAD1 and LAD2 are indicated. The conserved disulfide bond near LAD1 is highlighted in orange. The poly-Pro loop (PPL) is in a green box and the MLA loop in purple. The nomenclature of secondary structures was adapted from Trabi et al. (Trabi M, et al. (2004) *J Nat Prod* 67(5):806-810) with alterations according to the crystal structure of VyPAL2 (this work). Residues and motifs crucial for activity are labelled with the same color codes as used in the sequence alignment. Residues below the dotted line correspond to the oxyanion hole and those above the dotted line correspond to the proposed activity determinants. (B) Schemes proposed for ligation and hydrolysis by VyPAL2 and the role of LAD1 and LAD2. The first step of the mechanism is identical for hydrolysis and ligation, leading to formation of the S-acyl enzyme intermediate and is the rate limiting step. Its main determinant is LAD1. LAD2 controls the nature of activity to either favor the nucleophilic attack by a peptide (ligation) or a water molecule (hydrolysis). Full sequences of all aligned polypeptides are set forth in SEQ ID Nos. 5-14, 18 and 80-87 (VyPAL1=SEQ ID NO:5; VyPAL2=SEQ ID NO:6; VyPAL3=SEQ ID NO:7; VyPAL4=SEQ ID NO:8; VyPAL5=SEQ ID NO:9; VyAEP1=SEQ ID NO: 10; VyAEP2=SEQ ID NO:11; VyAEP3=SEQ ID NO:12; VyAEP4=SEQ ID NO:13; VcAEP=SEQ ID NO:14; Butelase-1=SEQ ID NO:88; Butelase 2=SEQ ID NO:80; OaAEP1b=SEQ ID NO:81; OaAEP2=SEQ ID NO:82.

One residue of OaAEP1b located in the S2 pocket, was previously reported to be a "gate-keeper", as it was found to play an important role in controlling enzyme efficiency (Yang, et al. (2017) JACS. Doi:10.1021/jacs.6b12637). The inventors found that this residue is commonly a glycine, while it appears to be a hydrophobic or bulky residue in PALs, such as valine in butelase-1 and cysteine in OaAEP1b. However, using the nature of the "gate-keeper" residue as the only criterion is insufficient to explain the range of activities observed in VyPAL1-3 isoforms: VyPAL2 a very efficient PAL and VyPAL3, a very poor enzyme both have similar gate-keeper residues: e.g. I and V respectively (FIG. 6A). Moreover, VcAEP that has Val (like butelase 1) as a gate-keeper residue is a protease (FIG. 5A). The inventors identified sequence variations in two regions of VyPAL1-3 that act as ligase activity determinants (LADs): (i) the S2 pocket (LAD1) comprising residues W243, I244 (the gate-keeper) and T245 in VyPAL2 and (ii) the S2' pocket (LAD2) including residues A174 and P175 (FIG. 6).

The LAD2 region of VyPAL1 and VyPAL2 is identical, while their Gate-keeper region (LAD1) bears two variations (FIG. 6): The T245A substitution was hypothesized to have little effect since the side chain of residue 245 is oriented opposite to the substrate binding area. It was therefore concluded that the difference in activity observed between VyPAL1 and 2 is due to the other W243L substitution making the enzyme "leakier" for hydrolysis and explaining the slight shift of VyPAL1 towards hydrolase at lower pH.

Figure 4:
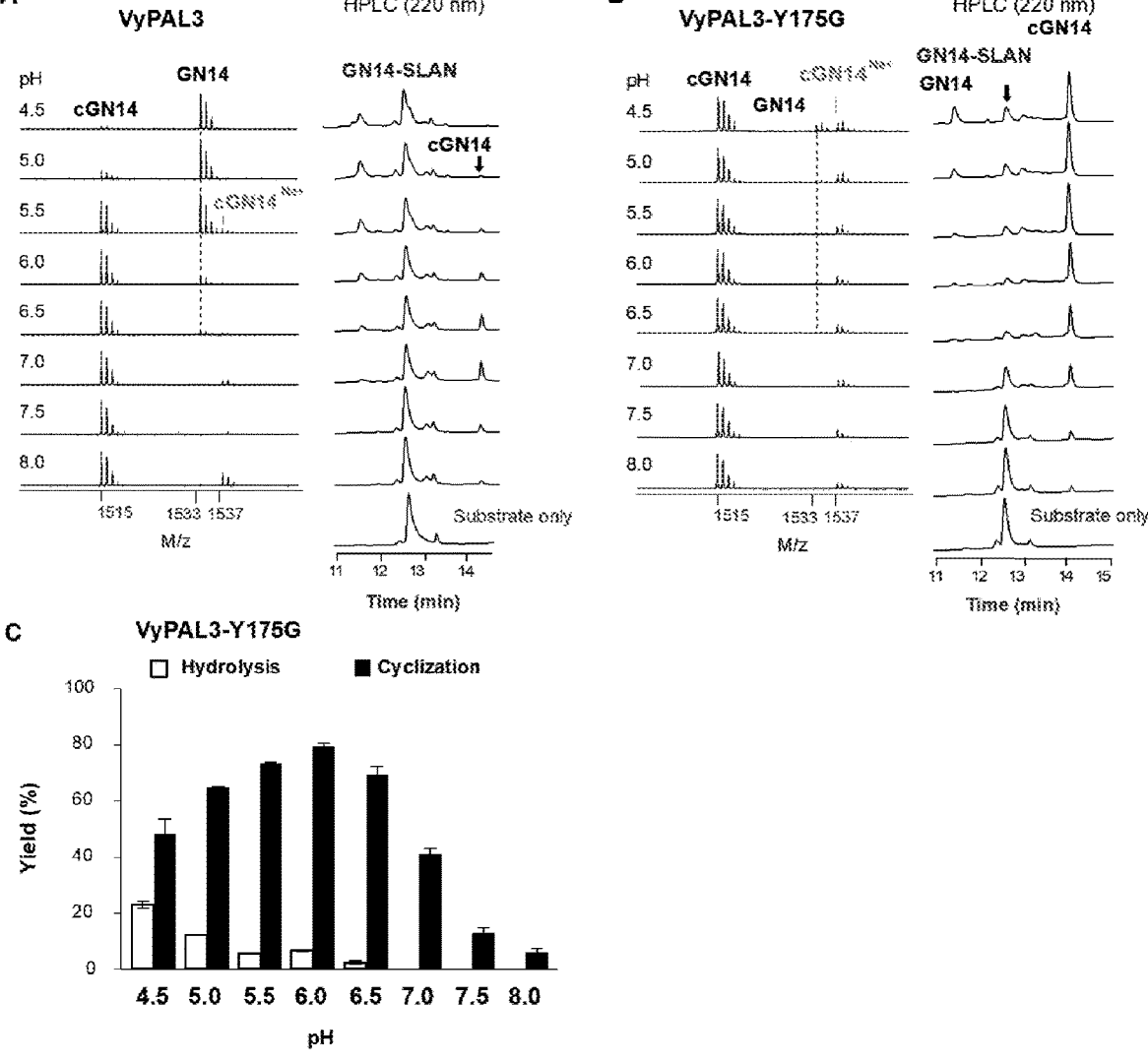
FIG. 4 depicts retro-engineering experiments in the S1' pocket of VyPAL3. All reactions were performed in the pH range 4.5 to 8.0. MS peaks of the hydrolysis product GN14 (SEQ ID NO:48) are marked with a dashed-line. (A) MS analysis of reactions catalyzed by VyPAL3 wild-type. (B) MS spectra of reactions catalyzed by VyPAL3-Y175G. (C) HPLC profiles of reactions catalyzed by VyPAL3 and VyPAL3-Y175G. (D) Quantitative summary of product ratio and reaction yield analyzed using RP-HPLC for VyPAL3-Y175G.

Compared to the VyPAL1 and 2 ligases, VyPAL3 has variations at both LAD1 and LAD2. However, the conservative substitutions at LAD1: V245 instead of an Ile gate-keeper residue and V246 instead of Thr (VyPAL2) are unlikely to account for the drastic change of activity that was observed (FIG. 1C). Rather, on the other side of the active site, in LAD2, the AP dipeptide present in VyPAL1 and 2 is replaced by the bulkier YA dipeptide. This variation was found to be responsible for the lower ligase activity observed in VyPAL3 compared to VyPAL1 and VyPAL2, as the bulky Tyr residue at this position could hamper the access of a peptidyl nucleophile to the acyl-enzyme intermediate. Confirming this, the inventors found that by inserting a smaller hydrophobic side chain such as Gly (or Ala) at the first position of LAD2 ligase efficiency could be significantly increased, as seen in the corresponding VyPAL3 single Y175G mutant (FIG. 4). Importantly, the inventors could confirm the involvement of the LAD2 region in controlling the ligase activity by introducing an equivalent mutation into VcAEP from *Viola canadensis* (compare FIGS. 5A and B). The volume occupied by Y at this position in VcAEP is likely to cause adverse effects such as accelerating the dissociation of leaving group and slowing down the binding of an incoming peptide, that are essential steps to displace the catalytic water molecule and thus favor ligation over hydrolysis. This is in line with the importance of the interactions at the prime side that was proposed previously to favor cyclization by preventing premature thioester hydrolysis. On the other hand, the side chain of Tyr175 should not disturb the putative catalytic water molecule. This water molecule is presumably located right above Gly174 of VyPal3—a strictly conserved residue immediately following the catalytic His- as observed in the cases of AtLEG-gamma and other legumains (Zauner, et al. (2018) J. Biol. Chem. Doi:10.1074/jbc.M117.817031)

The inventors found that the mechanism of AEPs and PALs can be decomposed in two steps: (i) Acyl-enzyme thioester intermediate formation which is likely the rate-limiting step and (ii) Nucleophilic attack by a water molecule (hydrolysis) or nucleophilic peptide (ligation) on the acyl-enzyme intermediate. Together with the known information on gate-keeper mutagenesis performed on OaAEP1b (Yang, supra), the obtained results set forth in the examples show that hydrophobic residues such as Val/Ile/Cys/Ala at this central position favor ligation, while the presence of Gly favors proteolysis (FIGS. 1 and 6). The LAD1 in S2 pocket may affect substrate positioning with an impact on enzyme activity, possibly by inducing some specific conformational strain in the substrate. Since changes at the gate-keeper mainly affect substrate binding and positioning, they will have a direct impact on intermediate formation and thus on the overall reaction rate. Conversely, changes in LAD2 would affect the nature and accessibility of the nucleophile and as a consequence, be decisive on the nature of the overall reaction catalyzed.

LAD2 was found to be a crucial determinant for the nature of the activity catalyzed by VyPALs and VcAEP: A bulky residue on this side of the active site, such as Tyr at the first position of the YA dipeptide in VyPAL3 and YP in VcAEP, facilitates the departure of the cleaved peptide group, which thus results in recruitment of the catalytic water and exposing the acyl-enzyme thioester to nucleophilic water molecules. This mechanism is in line with earlier studies that showed that a cleaved peptide group remaining in the S1' and S2' pockets displaced the nucleophilic water molecule and thus favors ligation over hydrolysis. Moreover, a bulky residue oriented in the direction where the incoming nucleophilic peptide would bind, hampers access to the acyl-enzyme intermediate, and thus severely reduces the rate of ligation. Conversely, small hydrophobic dipeptides like GA/AA/AP in the LAD2 retain the departing group (blocking access to the thioester bond), until another peptide acts as a nucleophile, leading to ligase activity. However, it was also found that mutations of both sites of VyPAL2 to engineer an AEP did not result in an efficient and drastic conversion into a protease like OaAEP2 or butelase 2, suggesting the existence of other determinants for proteolysis, beside LAD1 and LAD2 (data not shown). One attractive possibility is that residues within LAD1 (the gatekeeper) LAD2 (this work) and MLA cooperate to determine protease vs ligase activity. In this respect, it was found that the presence of a truncated MLA alone (Chen et al. (1998) *FEBS Lett* 441(3):361-5) does not necessarily imply a ligase activity, because VcAEP, which possesses a truncated MLA (FIG. 6) displays mainly protease activity (FIG. 5).

In summary the inventors discovered that the molecular determinants governing asparaginyl endopeptidases and ligases activity are primarily found in the amino acid composition of the substrate-binding grooves flanking the S1 pocket, in particular the LAD1 and LAD2 that are centered around the S2 and S1' pockets, respectively. Combining structural analysis and mutagenesis study, it was uncovered that, for an efficient peptide asparaginyl ligase, the first position of LAD1 is preferably bulky and aromatic, such as W/Y, and the second position hydrophobic, such as V/I/C/A but not G. For LAD2, it was found that GA/AA/AP dipeptides are favored. A bulky residue such as Y is disadvantageous at the first position of LAD2, as it is likely to destabilize the acyl-enzyme intermediate, by affecting the binding affinity of substrates and controlling the accessibility of water molecules and by increasing the dissociation rate of the cleaved peptide tail after the N/D residue. Therefore, a small residue such as G or A at the first position of this dipeptide is a necessary, although not always sufficient, condition for ligase activity. As long as this condition is met, a natural AEP is amenable to become a PAL through mutations or changes at other locations such as LAD1 (gate keeper) or more remote regions like the MLA.

Based on the above findings, the invention, in a first aspect, covers polypeptides having peptide asparaginyl ligase (PAL) activity in isolated form and, more specifically, is directed to an isolated polypeptide comprising, consisting essentially of or consisting of the amino acid sequence as set forth in SEQ ID NO:1. The polypeptide consisting of the amino acid sequence set forth in SEQ ID NO:1 is also referred to as "VyPAL2" or "VyPAL2 active form/domain" herein. "Isolated", as used herein, relates to the polypeptide in a form where it has been at least partially separated from other cellular components it may naturally occur or associate with. The polypeptide may be a recombinant polypeptide, i.e. polypeptide produced in a genetically engineered organism that does not naturally produce said polypeptide. Both native and recombinant polypeptides are post-translationally modified by N-linked glycosylation.

A polypeptide according to the present invention exhibits protein ligation activity, i.e. it is capable of forming a peptide bond between two amino acid residues, with these two amino acid residues being located on the same or different peptides or proteins, preferably on the same peptide or protein so that said ligation activity cyclizes said peptide or protein. Accordingly, in various embodiments, the polypeptide of the invention has cyclase activity. In various embodiments, this protein ligation or cyclase activity includes an endopeptidase activity, i.e. the polypeptide form a peptide bond between two amino acid residues following cleavage of an existing peptide bond. This means that cyclization need not to occur between the termini of a given peptide but can also occur between internal amino acid residues, with the amino acids C-terminal or N-terminal to the amino acid used for cyclization being cleaved off. In a preferred embodiment, the polypeptide forms a cyclized peptide by ligating the N-terminus to an internal amino acid and cleaving the remaining C-terminal amino acids.

The polypeptide as disclosed herein is "Asx-specific" in that the amino acid C-terminal to which ligation occurs, i.e. the C-terminal end of the peptide that is ligated, is either asparagine (Asn or N) or aspartic acid (Asp or D), preferably asparagine.

"Polypeptide", as used herein, relates to polymers made from amino acids connected by peptide bonds. The polypeptides, as defined herein, can comprise 50 or more amino acids, preferably 100 or more amino acids. "Peptides", as used herein, relates to polymers made from amino acids connected by peptide bonds. The peptides, as defined herein, can comprise 2 or more amino acids, preferably 5 or more amino acids, more preferably 10 or more amino acids, for example 10 to 50 amino acids.

In various embodiments, the polypeptide comprises or consists of an amino acid sequence that is at least 60%, 65%, 70%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or 99.5% identical or homologous to the amino acid sequence set forth in SEQ ID NO:1 over its entire length. In some embodiments, it has an amino acid sequence that shares at least 60, preferably at least 70, more preferably at least 80, most preferably at least 90% sequence identity with the amino acid sequence set forth in SEQ ID NO:1 over its entire length or has an amino acid sequence that shares at least 80, preferably at least 90, more preferably at least 95% sequence homology with the amino acid sequence set forth in SEQ ID NO:1 over its entire length.

In various embodiments, the polypeptide may be a precursor of the mature enzyme. In such embodiments, it may comprise or consist of the amino acid sequence set forth in SEQ ID NO:2 or SEQ ID NO:3. Also encompassed are polypeptides having an amino acid sequence that is at least 60%, 65%, 70%, 75%, 76%, 77%, 78%, 79%, 80%, 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.25%, or 99.5% identical or homologous to the amino acid sequence set forth in SEQ ID NO:2 or SEQ ID NO:3 over its entire length.

The identity of nucleic acid sequences or amino acid sequences is generally determined by means of a sequence comparison. This sequence comparison is based on the BLAST algorithm that is established in the existing art and commonly used (cf. for example Altschul et al. (1990) "Basic local alignment search tool", J. Mol. Biol. 215:403-

410, and Altschul et al. (1997): "Gapped BLAST and PSI-BLAST: a new generation of protein database search programs"; Nucleic Acids Res., 25, p. 3389-3402) and is effected in principle by mutually associating similar successions of nucleotides or amino acids in the nucleic acid sequences and amino acid sequences, respectively. A tabular association of the relevant positions is referred to as an "alignment." Sequence comparisons (alignments), in particular multiple sequence comparisons, are commonly prepared using computer programs which are available and known to those skilled in the art.

A comparison of this kind also allows a statement as to the similarity to one another of the sequences that are being compared. This is usually indicated as a percentage identity, i.e. the proportion of identical nucleotides or amino acid residues at the same positions or at positions corresponding to one another in an alignment. The more broadly construed term "homology", in the context of amino acid sequences, also incorporates consideration of the conserved amino acid exchanges, i.e. amino acids having a similar chemical activity, since these usually perform similar chemical activities within the protein. The similarity of the compared sequences can therefore also be indicated as a "percentage homology" or "percentage similarity." Indications of identity and/or homology can be encountered over entire polypeptides or genes, or only over individual regions. Homologous and identical regions of various nucleic acid sequences or amino acid sequences are therefore defined by way of matches in the sequences. Such regions often exhibit identical functions. They can be small, and can encompass only a few nucleotides or amino acids. Small regions of this kind often perform functions that are essential to the overall activity of the protein. It may therefore be useful to refer sequence matches only to individual, and optionally small, regions. Unless otherwise indicated, however, indications of identity and homology herein refer to the full length of the respectively indicated nucleic acid sequence or amino acid sequence.

In various embodiments, the polypeptide described herein comprises the amino acid residue N at the position corresponding to position 19 of SEQ ID NO:1; and/or the amino acid residue H at the position corresponding to position 124 of SEQ ID NO:1; and/or the amino acid residue C at the position corresponding to position 166 of SEQ ID NO:1. In various embodiments, at least the catalytic dyad formed by the amino acid residue H at the position corresponding to position 124 of SEQ ID NO:1; and/or the amino acid residue C at the position corresponding to position 166 of SEQ ID NO:1 is present, preferably in combination with the amino acid residue N at the position corresponding to position 19 of SEQ ID NO:1, thus forming the complete catalytic triad. It has been found that these amino acid residues are necessary for the catalytic activity (ligase/cyclase/endopeptidase activity) of the polypeptide. In preferred embodiments, the polypeptides thus comprise at least two, more preferably all three of the above indicated residues at the given or corresponding positions.

All amino acid residues are generally referred to herein by reference to their one letter code and, in some instances, their three letter code. This nomenclature is well known to those skilled in the art and used herein as understood in the field.

In various embodiments, the polypeptide described herein comprises the amino acid residue A at the position corresponding to position 126. In various embodiments, the polypeptide described herein comprises the amino acid residue A or P, preferably P, at the position corresponding to position 127 of SEQ ID NO:1. Alternatively, the amino acid residue at the position corresponding to position 126 of SEQ ID NO:1 may be G. In these embodiments, the amino acid residue at the position corresponding to position 127 of SEQ ID NO:1 is preferably A. These motifs AP, AA and GA are also referred to herein as Ligase Activity Determinant 2 (LAD2), as they are critical determinants for the ligase activity and mutation of other amino acids at these positions to these motifs may convert an endopeptidase to a ligase enzyme in that its predominant enzymatic activity is switched. In various embodiments the motif at the positions corresponding to positions 126 and 127 of SEQ ID NO:1 is not GP, but either AP, AA or GA.

In various embodiments, the polypeptide described herein comprises the amino acid residue W or Y at the position corresponding to position 195, the amino acid residue I or V at the position corresponding to position 196, and the amino acid residue T, A or V at the position corresponding to position 197 of SEQ ID NO:1. It has been found that this motif W-I/V-T/A/V, also referred to herein as Ligase Activity Determinant 1 (LAD1), is also a critical determinant for the ligase activity. In addition to the known gatekeeper position that corresponds to position 196 in SEQ ID NO:1, it has been found that also positions 195 and 197, in particular 195, are relevant for determining ligase/endopeptidase activity. Again, mutation of other amino acids at these positions to these motifs may convert an endopeptidase to a ligase enzyme in that its predominant enzymatic activity is switched or increase the ligase activity of a mixed ligase/endopeptidase.

In various embodiments, the polypeptide described herein comprises the amino acid residues R at the position corresponding to position 21, H at the position corresponding to position 22, D at the position corresponding to position 123, E at the position corresponding to position 164, S at the position corresponding to position 194, and D at the position corresponding to position 215 of SEQ ID NO:1. These amino acid residues are also referred to herein as "S1 pocket".

In various embodiments, the polypeptide described herein comprises the amino acid residues C at the positions corresponding to positions 199 and 212 of SEQ ID NO:1. These two residues typically form a disulfide bridge in the mature polypeptide.

The polypeptide of the invention may, in various embodiments, comprise further more or less invariable sequence elements, such as the poly-Pro loop (PPL). Said loop has the consensus sequence P/A-G/T/S-X-X-P/E-G/D/P-V/F/A/P-P-L/P/A/E-E and comprises at least 2 and up to 5 proline residues. Typical are 2, 3, 4 or 5 proline residues at the indicated positions. The PPL occupies positions 200-208 of SEQ ID NO:1.

Another motif that may be present in the polypeptides of the invention is the so-called MLA motif spanning residues 244-249 of SEQ ID NO:1. This may have the sequence KKIAYA or NKIAYA (SEQ ID Nos. 15 and 16).

In various embodiments, the polypeptides of the invention comprise the LAD1 and LAD2 motifs as described above. In further embodiments, they additionally comprise one, two, three or all four of the S1 pocket, SS bridge, PPL and MLA motif, as defined above.

In various embodiments, the isolated polypeptide of the invention can be activated by acid treatment at a pH of 5.0 or less, preferably 4.5 or less. This applies to those polypeptides that comprise a C-terminal cap sequence or activation domain. Such C-terminal domain is, for example, present in the polypeptides having the amino acid sequence set forth in SEQ ID NO:3. The concrete sequence used therein (SEQ ID NO:17) is derived from the cap sequence of VyPAL1 (SEQ ID NO:5)

The isolated polypeptides of the present invention preferably have enzymatic activity, in particular protein ligase, preferably cyclase activity. In various embodiments, this means that they can ligate a given peptide with an efficiency of 60% or more, preferably 70% or more, more preferably 80% or more. The efficiency is determined as the amount of a given peptide/polypeptide cyclized relative to the total amount of said peptide/polypeptide in %.

It is preferred that the polypeptides of the invention have at least 50%, more preferably at least 70, most preferably at least 90% of the protein ligase activity of the enzyme having the amino acid sequence of SEQ ID NO:1.

In various embodiments, the isolated polypeptide of the invention is capable of cyclizing a given peptide with an efficiency of 60% or more, preferably 80% or more, preferably at a pH of 5.5 or higher. The cyclization activity may also be determined at pH values of 6.0, 6.5, 7.0, 7.5 or higher. This is relevant, since at low pH conditions, such as below pH 5, many ligases may exhibit a certain degree of endopeptidase activity.

In various embodiments, the polypeptides of the invention hydrolyze a given peptide with an efficiency of 20% or less, preferably 5% or less. The efficiency is determined as the amount of a given peptide/polypeptide hydrolyzed relative to the total amount of said peptide/polypeptide in %. Again, since the pH may influence the activity, hydrolysis activity is preferably determined at a pH of 5.5 or higher, for example at pH values of 6.0, 6.5, 7.0, 7.5 or higher In addition to the above-described modifications, polypeptides according to the embodiments described herein can comprise amino acid modifications, in particular amino acid substitutions, insertions, or deletions. Such polypeptides are, for example, further developed by targeted genetic modification, i.e. by way of mutagenesis methods, and optimized for specific purposes or with regard to special properties (for example, with regard to their catalytic activity, stability, etc.). If such additional modifications are introduced into the polypeptides of the invention, these preferably do not affect, alter or reverse the sequence motifs detailed above, i.e. the catalytic residues, the LAD1 and LAD2 motifs. This means that the above-defined features of these residues/motifs are not changed by these additional mutations beyond that what is defined above. It can be further preferred that additionally one, two, three or all four of the S1 pocket, SS bridge, PPL and MLA motif are retained without additional modifications, i.e. modifications going beyond those detailed above. In addition, nucleic acids contemplated herein can be introduced into recombination formulations and thereby used to generate entirely novel protein ligases, cyclases or other polypeptides.

In various embodiments, the polypeptides having ligase/cyclase activity may be post-translationally modified, for example glycosylated. Such modification may be carried out by recombinant means, i.e. directly in the host cell upon production, or may be achieved chemically or enzymatically after synthesis of the polypeptide, for example in vitro.

For example, the known PAL butelase-1 (SEQ ID NO:18) is glycosylated at N94 and N286 with bulky heterogeneous glycans, which results in an increase of additional mass of about 6 kDa. The recombinant VyPAL2 (SEQ ID Nos. 1-3) is glycosylated at positions N102, N145 and N237, using the numbering of SEQ ID NO:2, with small glycans, and which results in an additional increased mass of about 3 kDa. The polypeptides of the invention may thus be glycosylated with bulky, heterogeneous glycans, for example at positions corresponding to positions N94 and N286 of SEQ ID NO:18 or with small glycans at positions corresponding to positions N102, N145 and N237 of SEQ ID NO:2.

The objective of the described modifications may be to introduce targeted mutations, such as substitutions, insertions, or deletions, into the known molecules in order, for example, to alter substrate specificity and/or improve the catalytic activity. For this purpose, in particular, the surface charges and/or isoelectric point of the molecules, and thereby their interactions with the substrate, can be modified. Alternatively or additionally, the stability of the polypeptide can be enhanced by way of one or more corresponding mutations, and its catalytic performance thereby improved. Advantageous properties of individual mutations, e.g. individual substitutions, can supplement one another.

In various embodiments, the polypeptide may be characterized in that it is obtainable from a polypeptide as described above as an initial molecule by single or multiple conservative amino acid substitution. The term "conservative amino acid substitution" means the exchange (substitution) of one amino acid residue for another amino acid residue, where such exchange does not lead to a change in the polarity or charge at the position of the exchanged amino acid, e.g. the exchange of a nonpolar amino acid residue for another nonpolar amino acid residue. Conservative amino acid substitutions in the context of the invention encompass, for example, G=A=S, I=V=L=M, D=E, N=Q, K=R, Y=F, S=T, G=A=I=V=L=M=Y=F=W=P=S=T.

Alternatively or additionally, the polypeptide may be characterized in that it is obtainable from a polypeptide contemplated herein as an initial molecule by fragmentation or by deletion, insertion, or substitution mutagenesis, and encompasses an amino acid sequence that matches the initial molecule as set forth in SEQ ID Nos. 1-14 over a length of at least 150, 160, 170, 180, 190, 200, 210, 220, 230, 240, 250, 260 or 265 continuously connected amino acids. It is preferred that in such embodiments, the amino acids N19, H124 and C166, as well as the above-defined LAD1, LAD2 and optionally also any one or more of the S1 pocket, the PPL, MLA motif and disulfide bridge contained in the initial molecule are still present.

In various embodiments, the present invention thus also relates to fragments of the polypeptides described herein, with said fragments retaining enzymatic activity. It is preferred that they have at least 50%, more preferably at least 70, most preferably at least 90% of the protein ligase and/or cyclase activity of the initial molecule, preferably of the polypeptide having the amino acid sequence of SEQ ID NO:1. The fragments are preferably at least 150 amino acids in length, more preferably at least 200 or 250. It is further preferred that these fragments comprise the amino acids N, H and C at positions corresponding to positions 19, 124 and 166 of SEQ ID NO:1 as well as the above-defined LAD1, LAD2 and optionally also any one or more of the S1 pocket, the PPL, MLA motif and disulfide bridge contained in the initial molecule. Preferred fragments therefore comprise amino acids 19-197, more preferably 19-212, most preferably 19-249 of the amino acid sequence set forth in SEQ ID NO:1.

The nucleic acid molecules encoding the polypeptides described herein, as well as a vector containing such a nucleic acid, in particular a copying vector or an expression vector also form part of the present invention.

These can be DNA molecules or RNA molecules. They can exist as an individual strand, as an individual strand complementary to said individual strand, or as a double strand. With DNA molecules in particular, the sequences of both complementary strands in all three possible reading frames are to be considered in each case. Also to be considered is the fact that different codons, i.e. base triplets, can code for the same amino acids, so that a specific amino acid sequence can be coded by multiple different nucleic acids. As a result of this degeneracy of the genetic code, all nucleic acid sequences that can encode one of the above-described polypeptides are included in this subject of the invention. The skilled artisan is capable of unequivocally determining these nucleic acid sequences, since despite the degeneracy of the genetic code, defined amino acids are to be associated with individual codons. The skilled artisan can therefore, proceeding from an amino acid sequence, readily ascertain nucleic acids coding for that amino acid sequence. In addition, in the context of nucleic acids according to the present invention one or more codons can be replaced by synonymous codons. This aspect refers in particular to heterologous expression of the enzymes contemplated herein. For example, every organism, e.g. a host cell of a production strain, possesses a specific codon usage. "Codon usage" is understood as the translation of the genetic code into amino acids by the respective organism. Bottlenecks in protein biosynthesis can occur if the codons located on the nucleic acid are confronted, in the organism, with a comparatively small number of loaded tRNA molecules. Also it codes for the same amino acid, the result is that a codon becomes translated in the organism less efficiently than a synonymous codon that codes for the same amino acid. Because of the presence of a larger number of tRNA molecules for the synonymous codon, the latter can be translated more efficiently in the organism.

By way of methods commonly known today such as, for example, chemical synthesis or the polymerase chain reaction (PCR) in combination with standard methods of molecular biology or protein chemistry, a skilled artisan has the ability to manufacture, on the basis of known DNA sequences and/or amino acid sequences, the corresponding nucleic acids all the way to complete genes. Such methods are known, for example, from Sambrook, J., Fritsch, E. F., and Maniatis, T, 2001, Molecular cloning: a laboratory manual, 3rd edition, Cold Spring Laboratory Press.

"Vectors" are understood for purposes herein as elements—made up of nucleic acids—that contain a nucleic acid contemplated herein as a characterizing nucleic acid region. They enable said nucleic acid to be established as a stable genetic element in a species or a cell line over multiple generations or cell divisions. In particular when used in bacteria, vectors are special plasmids, i.e. circular genetic elements. In the context herein, a nucleic acid as contemplated herein is cloned into a vector. Included among the vectors are, for example, those whose origins are bacterial plasmids, viruses, or bacteriophages, or predominantly synthetic vectors or plasmids having elements of widely differing derivations. Using the further genetic elements present in each case, vectors are capable of establishing themselves as stable units in the relevant host cells over multiple generations. They can be present extrachromosomally as separate units, or can be integrated into a chromosome resp. into chromosomal DNA.

Expression vectors encompass nucleic acid sequences which are capable of replicating in the host cells, by preference microorganisms, particularly preferably bacteria, that contain them, and expressing therein a contained nucleic acid. In various embodiments, the vectors described herein thus also contain regulatory elements that control expression of the nucleic acids encoding a polypeptide of the invention.

Expression is influenced in particular by the promoter or promoters that regulate transcription. Expression can occur in principle by means of the natural promoter originally located in front of the nucleic acid to be expressed, but also by means of a host-cell promoter furnished on the expression vector or also by means of a modified, or entirely different, promoter of another organism or of another host cell. In the present case at least one promoter for expression of a nucleic acid as contemplated herein is made available and used for expression thereof. Expression vectors can furthermore be regulated, for example by way of a change in culture conditions or when the host cells containing them reach a specific cell density, or by the addition of specific substances, in particular activators of gene expression. One example of such a substance is the galactose derivative isopropyl-beta-D-thiogalactopyranoside (IPTG), which is used as an activator of the bacterial lactose operon (lac operon). In contrast to expression vectors, the contained nucleic acid is not expressed in cloning vectors.

In a further aspect, the invention is also directed to a host cell, preferably a non-human host cell, containing a nucleic acid as contemplated herein or a vector as contemplated herein. A nucleic acid as contemplated herein or a vector containing said nucleic acid is preferably transformed into a microorganism, which then represents a host cell according to an embodiment. Methods for the transformation of cells are established in the existing art and are sufficiently known to the skilled artisan. All cells are in principle suitable as host cells, i.e. prokaryotic or eukaryotic cells. Those host cells that can be manipulated in genetically advantageous fashion, e.g. as regards transformation using the nucleic acid or vector and stable establishment thereof, are preferred, for example single-celled fungi or bacteria. In addition, preferred host cells are notable for being readily manipulated in microbiological and biotechnological terms. This refers, for example, to easy culturability, high growth rates, low demands in terms of fermentation media, and good production and secretion rates for foreign proteins. The polypeptides can furthermore be modified, after their manufacture, by the cells producing them, for example by the addition of sugar molecules, formylation, amination, etc. Post-translation modifications of this kind can functionally influence the polypeptide.

Further embodiments are represented by those host cells whose activity can be regulated on the basis of genetic regulation elements that are made available, for example, on the vector, but can also be present a priori in those cells. They can be stimulated to expression, for example, by controlled addition of chemical compounds that serve as activators, by modifying the culture conditions, or when a specific cell density is reached. This makes possible economical production of the proteins contemplated herein. One example of such a compound is IPTG, as described earlier.

Preferred host cells are prokaryotic or bacterial cells, such as *E. coli* cells. Bacteria are notable for short generation times and few demands in terms of culturing conditions. As a result, economical culturing methods resp. manufacturing methods can be established. In addition, the skilled artisan has ample experience in the context of bacteria in fermentation technology. Gram-negative or Gram-positive bacteria may be suitable for a specific production instance, for a wide variety of reasons to be ascertained experimentally in the individual case, such as nutrient sources, product formation rate, time requirement, etc. In various embodiments, the host cells may be *E. coli* cells.

Host cells contemplated herein can be modified in terms of their requirements for culture conditions, can comprise other or additional selection markers, or can also express other or additional proteins. They can, in particular, be those host cells that transgenically express multiple proteins or enzymes.

The host cell can, however, also be a eukaryotic cell, which is characterized in that it possesses a cell nucleus. A further embodiment is therefore represented by a host cell which is characterized in that it possesses a cell nucleus. In contrast to prokaryotic cells, eukaryotic cells are capable of post-translationally modifying the protein that is formed. Examples thereof are fungi such as Actinomycetes, or yeasts such as *Saccharomyces* or *Kluyveromyces* or insect cells, such as Sf9 cells. This may be particularly advantageous, for example, when the proteins, in connection with their synthesis, are intended to experience specific modifications made possible by such systems. Among the modifications that eukaryotic systems carry out in particular in conjunction with protein synthesis are, for example, the bonding of low-molecular-weight compounds such as membrane anchors or oligosaccharides. In various embodiments, the host cells are thus eukaryotic cells, such as insect cells, for example Sf9 cells.

The host cells contemplated herein are cultured and fermented in a usual manner, for example in discontinuous or continuous systems. In the former case a suitable nutrient medium is inoculated with the host cells, and the product is harvested from the medium after a period of time to be ascertained experimentally. Continuous fermentations are notable for the achievement of a flow equilibrium in which, over a comparatively long period of time, cells die off in part but are also in part renewed, and the protein formed can simultaneously be removed from the medium.

Host cells contemplated herein are preferably used to manufacture the polypeptides described herein.

A further aspect of the invention is therefore a method for manufacturing a polypeptide as described herein, comprising culturing a host cell contemplated herein; and isolating the polypeptide from the culture medium or from the host cell. Culture conditions and mediums can be selected by those skilled in the art based on the host organism used by resorting to general knowledge and techniques known in the art.

In a still further aspect, the present invention relates to the use of polypeptides described above for protein ligation, in particular for cyclizing one or more peptide(s).

It is understood that while the uses of the enzymes described herein are described in the following by reference to peptide substrates, they can similarly be used for the corresponding polypeptides or proteins. The invention thus also covers embodiments where polypeptides or proteins are used as substrates. These polypeptides or proteins can comprise the structural motifs as described below in the context of peptide substrates. Also encompassed are embodiments, where peptide fragments, such as fragments of human peptide hormones that retain functionality, or peptide derivatives, such as (backbone) modified peptides, including, for example, thiodepsipeptides, are utilized. Accordingly, the present invention also covers fragments and derivatives of the peptide substrates disclosed herein.

In various embodiments the peptide to be ligated or cyclized can be any peptide, typically at least 10 amino acids in length, as long as it contains a recognition and ligation sequence that is recognized, bound and ligated by the ligase/cyclase. This amino acid sequence of the peptide to be ligated or cyclized may comprise the amino acid residue N or D, preferably N. In various embodiments, the peptide to be cyclized or ligated comprises the amino acid sequence $(X)_oN/D(X)_p$, with X being any amino acid, o being an integer of 1 or more, preferably 2 or more, and p being an integer of 1 or more, preferably of 2 or more. In a preferred embodiment, $(X)_p$ is $X^3X^4(X)_r$, $H(X)_r$ or $HV(X)_r$ with $X^3$ being any amino acid with the exception of P, preferably H, G or S, $X^4$ being a hydrophobic or aromatic amino acid, preferably selected from L, I, V, F, C, W, Y and M, and r being 0 or an integer of 1 or more. In various embodiments, the peptide comprises the amino acid sequence $(X)_oNH$ or $(X)_oNHV$ or $(X)_oNGL$ or $(X)_oNSL$. Said amino acid sequence is preferably located at or near the C-terminus of the peptide to be ligated or cyclized, as all amino acids C-terminal to the N will be cleaved off during ligation/ cyclization. Accordingly, in all afore-mentioned embodiments, p or r are preferably integers of up to 20, preferably up to 5. Particularly preferred are embodiments, where p is 2, with $(X)_p$ preferably being $X^3X^4(X)_r$ as defined above, and where r is optionally 0.

In alternative embodiments, the peptide to be ligated or cyclized may comprise the amino acid sequence $(X)_oN*/D*$, wherein X is any amino acid, o is an integer of at least 2 and the C-terminal carboxy group (of the N or D residue) is replaced by a group of the formula —C(O)—N(R')₂, with R' being any residue, such as, for example, alkyl. In such embodiments, the terminal —C(O)OH group of the N or D residue, preferably the alpha-carboxy group in case of D, is modified to form the group —C(O)—N(R')₂. These C-terminally amidated D or N residues are indicated herein by D* and N*, respectively. It has been found that the enzymes disclosed herein can cleave the amide group and ligate said N or D residue to the N-terminus of another peptide of interest or the N-terminus of the same peptide that comprises the N or D residue.

The N-terminal part of the peptide to be ligated preferably comprises the amino acid sequence $X^1X^2(X)_q$, wherein X can be any amino acid; $X^1$ can be any amino acid with the exception of Pro; $X^2$ can be any amino acid, but preferably is a hydrophobic amino acid, such as Val, Ile or Leu, or Cys; and q is 0 or an integer of 1 or more. Preferred are in the $X^1$ position in the following order: G=H>M=W— F>R=A=I=K=L=N=S=Q=C>T=V=Y>D=E. "=" indicates that the respective amino acids are similarly preferred, while ">" indicates a preference of the amino acids listed before the symbol over the ones listed after the symbol. Preferred in the $X^2$ position are in the following order: L>V>I>C>T>W>A=F>Y>M>Q>S. Less preferred in the $X^2$ position are P, D, E, G, K, R, N and H. Particularly preferred in the $X^1$ position are G and H and in the $X^2$ position L, V, I and C, such as the dipeptide sequences GL, GV, GI, GC, HL, HV, HI and HC.

In preferred embodiments, the peptide to be ligated or cyclized thus comprises in N- to C-terminal orientation, the amino acid sequence $X^1X^2(X)_q(X)_oN/D(X)_p$, wherein X, $X^1$, $X^2$, o, p, and q are defined as above, with o preferably being at least 7. In various embodiments, (1) q is 0 and o is an integer of at least 7; and/or (2) $X^1$ is G or H; and/or (3) $X^2$ is L, V, I or C; and/or (4) p is at least 2 but not more than 22, preferably 2-7, more preferably $H(X)_r$ or $HV(X)_r$, most preferably HX or HV. In various embodiments, (1) q is 0 and o is an integer of at least 7; and (2) $X^1$ is G or H; and (3) $X^2$ is L, V, I or C; and (4) p is at least 2 but not more than 22, preferably 2-7, more preferably $(X)_p$ is $X^3X^4(X)_r$, $H(X)_r$ or $HV(X)_r$, most preferably HX or HV or XL or GL or XS or LS.

In various embodiments, the peptide to be cyclized is the linear precursor form of a cyclic cystine knot polypeptide, in particular a cyclotide. Cyclotides are a topologically unique family of plant proteins that are exceptionally stable. They comprise ~30 amino acids arranged in a head-to-tail cyclized peptide backbone that additionally is restrained by a cystine knot motif associated with six conserved cysteine residues. The cystine knot is built from two disulfide bonds and their connecting backbone segments forming an internal ring in the structure that is threaded by the third disulfide bond to form an interlocking and cross braced structure. Superimposed on this cystine knot core motif are a well-defined beta-sheet and a series of turns displaying short surface-exposed loops.

Cyclotides express a diversity of peptide sequences within their backbone loops and have a broad range of biological activities. They are thus of great interest for pharmaceutical applications. Some plants from which they are derived are used in indigenous medicines, including kalata-kalata, a tea from the plant *Oldenlandia affinis* that is used for accelerating childbirth in Africa that contains the prototypic cyclotide kalata B1 (kB1). Their exceptional stability means that they have attracted attention as potential templates in peptide-based drug design applications. In particular, the grafting of bioactive peptide sequences into a cyclotide framework offers the promise of a new approach to stabilize peptide-based therapeutics, thereby overcoming one of the major limitations on the use of peptides as drugs.

In various embodiments, the peptide to be cyclized is thus 10 or more amino acids in length, preferably up to 50 amino acids, in some embodiments about 25 to 35 amino acids in length. The peptide to be cyclized may comprise or consist of the amino acid of the precursor of cyclotide kalata B1 from *Oldenlandia affinis* as set forth in SEQ ID NO:20.

In various embodiments, the peptide to be cyclized comprises or consists of the amino acid sequence $(X)_nC(X)_nC$ $(X)_nC(X)_nC(X)_nC(X)_nNHV(X)_n$, wherein each n is an integer independently selected from 1 to 6 and X can be any amino acid. Such peptides are precursors of cyclic cystine knot polypeptides that form cystine bonds between the six cysteine residues, as described above, and which can be cyclized by the enzymes described herein by cleaving off the C-terminal $HV(X)_n$ sequence and ligating the (then C-terminal) N residue to the N-terminal residue.

The peptides to be cyclized may, in various embodiments, include the linear precursors disclosed in US2012/0244575. This document is for this purpose incorporated herein by reference in its entirety.

In various additional embodiments, the peptides to be cyclized include, but are not limited to linear precursors of peptide toxins and antimicrobial peptides, such as bacteriocins, such as bacteriocin AS-48 (SEQ ID NO:19), conotoxins, thanatins (insect antimicrobial peptides) and histatins (human saliva antimicrobial peptides). Other peptides that may be cyclized are precursors of cyclic human or animal peptide hormones, including, but not limited to neuromedin, salusin alpha, apelin and galanin. Exemplary peptides include or consist of any one of the amino acid sequences set forth in SEQ ID Nos. 21-31.

Further peptides that can be ligated or cyclized using the enzymes and methods disclosed herein include, without limitation, Adrenocorticotropic Hormone (ACTH), Adrenomedullin, Intermedin, Proadrenomedullin, Adropin, Agelenin, AGRP, Alarin, Insulin-Like Growth Factor-Binding Protein 5, Amylin, Amyloid b-Protein, Amphipathic Peptide Antibiotic, LAH4, Angiotensin I, Angiotensin II, A-Type (Atrial) Natriuretic Peptide (ANP), Apamin, Apelin, Bivalirudin, Bombesin, Lysyl-Bradykinin, B-Type (Brain) Natriuretic Peptide, C-Peptide (insulin precursor), Calcitonin, Cocaine- and Amphetamine-Regulated Transcript (CART), Calcitonin Gene Related Peptide (CGRP), Cholecystokinin (CCK)-33, Cytokine-Induced Neutrophil Chemoattractant-1/growth-related oncogene (CINC), Colivelin, Corticotropin-Releasing Factor (CRF), Cortistatin, C-Type Natriuretic Peptide (CNP), Decorsin, human neutrophil peptide-1 (HNP-1), HNP-2, HNP-3, HNP-4, human defensin HDS, HD6, human beta defensin-1 (hbd1), hbd2, hbd3, hbd4, Delta Sleep-Inducing Peptide (DSIP), Dermcidin-1L, Dynorphin A, Elafin, Endokinin C, Endokinin D, b-Lipotropin, g-Endorphin, Endothelin-1, Endothelin-2, Endothelin-3, Big-Endothelin-1, Big-Endothelin-2, Big-Endothelin-3, Enfuviritide, Exendin-4, MBP, Myelin Oligodendrocyte Protein (MOG), Glu-fibrinopeptide B, Galanin, Galanin-like Peptide, Big Gastrin (Human), Gastric Inhibitory Polypeptide (GIP), Gastrin Releasing Peptide, Ghrelin, Glucagon, Glucagon-like peptide-1 (GLP-1), GLP-2, Growth Hormone Releasing Factor (GRF, GHRF), Guanylin, Uroguanylin, Uroguanylin Isomer A, Uroguanylin Isomer B, Hepcidin, Liver-Expressed Antimicrobial Peptide (LEAP-2), Humanin, Joining Peptide (rJP), Kisspeptin-10, Kisspeptin-54, Liraglutide, LL-37 (Human Cathelicidine), Luteinizing Hormone Releasing Hormone (LHRH), Magainin 1, Mastoparan, alpha-Mating Factor, Mast Cell Degranulating (MCD) Peptide, Melanin-Concentrating Hormone (MCH), alpha-Melanocyte Stimulating Hormone (alpha-MSH), Midkine, Motilin, neuroendocrine regulatory peptide 1 (NERP1), NERP2, Neurokinin A, Neurokinin B, Neuromedin B, Neuromedin C, Neuromedin S, Neuromedin U8, Neuronostatin-13, Neuropeptide B-29, Neuropeptide S (NPS), Neuropeptide W-30, Neuropeptide Y (NPY), Neurotensin, Nociceptin, Nocistatin, Obestatin, Orexin-A, Osteocalcin, Oxytocin, Catestatin, Chromogranin A, Parathyroid Hormone (PTH), Peptide YY, Pituitary Adenylate Cyclase Activating Polypeptide 38 (PACAP-38), Platelet Factor-4, Plectasin, Pleiotrophin, Prolactin-Releasing Peptide, Pyroglutamylated RFamide Peptide (QRFP), RFamide-Related Peptide-1, Secretin, Serum Thymic Factor (FTS), Sodium Potassium ATPase Inhibitor-1 (SPAI-1), Somatostatin, Somatostatin-28, Stresscopin, Urocortin, Substance P, Echistatin, Enterotoxin STp, Guangxitoxin-1E, Urotensin II, Vasoactive intestinal peptide (VIP), and Vasopressin as well as fragments and derivatives thereof. The afore-mentioned peptides may be of human or animal, such as rat, mouse, pig, origin. All of them all well-known to those skilled in the art and their amino acid sequences are readily available.

In various other embodiments, polypeptides or proteins of more than 50 amino acids length are used as cyclization substrates. In such a reaction, the polypeptide/protein may be cyclized by ligating its C- to its N-terminus.

In various embodiments, two or more peptides are ligated by the enzymes of the invention. This may include formation of macrocycles consisting of two or more peptides, preferable are macrocyclic dimers. The peptides to be ligated can be any peptides, as long as at least one of them contains a recognition and ligation sequence that is recognized, bound and ligated by the ligase/cyclase. Suitable peptides have been described above in connection with the cyclization strategy. The same peptides can also be used for ligation to another peptide that may be the same or different. One of the peptides to be ligated may for example be a polypeptide that has enzymatic activity or another biological function. The peptides to be ligated may also include marker peptides or peptides that comprise a detectable marker, such as a fluorescent marker or biotin. According to such embodiments, a polypeptide that has bioactivity can be fused to a detectable marker. In various embodiments, at least one of the peptides to be ligated has a length of 25 amino acids or more, preferably 50 amino acids or more (and thus may be a "polypeptide", in the sense of the present invention).

The peptides to be ligated can comprise or consist of any of the amino acid sequences set forth in SEQ ID Nos. 32 to 42. Preferred peptides to be ligated to form (macrocyclic) dimers include the peptides having the amino acid sequence set forth in any one of SEQ ID Nos. 32-36. Preferred N-terminal peptides to be ligated (with one C-terminal peptide) to form a linear fusion peptide include the peptides having the amino acid sequence set forth in any one of SEQ ID Nos. 22, 25 and 32. Preferred C-terminal peptides to be ligated (with one N-terminal peptide) to form a linear fusion peptide include the peptides having the amino acid sequence set forth in any one of SEQ ID Nos. 23, 24 and 26.

The peptides to be ligated or cyclized can also be fusion peptides or polypeptides in which an Asx-containing tag has been C-terminally fused to the peptide of interest that is to be ligated or fused. The Asx-containing tag preferably has the amino acid sequence N/D(X)$_p$, as defined above, including the various embodiments. Alternatively, an amidated N or D (N* or D* as defined above) may be fused to the C-terminal end of the peptide or polypeptide to be ligated or fused. The other peptide to which this fusion peptide or polypeptide is ligated can be as defined above. Alternatively, the fusion peptide or polypeptide may be cyclized by forming a bond between its C- and N-terminus. In one embodiment, the fusion peptide or polypeptide may be green fluorescent protein (GFP) fused to the C-terminal tag of the amino acid sequence NHV (SEQ ID NO: 43) and the ligated peptide may be a biotinylated peptide of the amino acid sequence GIGK(biotinylated)R (SEQ ID NO: 44). Generally, polypeptides and proteins that may be ligated to peptides, such as peptides bearing signaling or detectable moieties, or cyclized using the methods and uses described herein, include, without limitation antibodies, antibody fragments, antibody-like molecules, antibody mimetics, peptide aptamers, hormones, various therapeutic proteins and the like.

In various embodiments, the ligase activity is used to fuse a peptide bearing a detectable moiety, such as a fluorescent group, including fluoresceins, such as fluorescein isothiocyanate (FITC), or coumarins, such as 7-Amino-4-methyl-coumarin, to a polypeptide or protein, such as those mentioned above. In various embodiments, the protein can be an antibody fragment, such as a human anti-ABL scFv, for example with the amino acid sequence set forth in SEQ ID NO:45, or an antibody mimetic, such as a darpin (designed ankyrin repeat proteins), for example a darpin specific for human ERK, for example with the amino acid sequence set forth in SEQ ID NO:46.

Use of a detectable marker such as fluorescein or derivatives thereof and/or of a peptide that can easily be radiolabeled with elements 1-125 or 1-131, this allows using a single reagent imaging of tumors in vivo using PET or SPECT followed by fluorescent detection in organ sections or biopsies.

In still another aspect, the invention relates to a method for cyclizing a peptide, polypeptide or protein, the method comprising incubating said peptide, polypeptide, or protein with the polypeptides having ligase/cyclase activity described above in connection with the inventive uses under conditions that allow cyclization of said peptide.

In a still further aspect, the invention relates to a method for ligating at least two peptides, polypeptides or proteins, the method comprising incubating said peptides, polypeptides or proteins with the polypeptides described above in connection with the inventive uses under conditions that allow ligation of said peptides.

The peptides, polypeptides and proteins to be cyclized or ligated according to these methods are, in various embodiments, similarly defined as the peptides, polypeptides and proteins to be cyclized or ligated according to the above-described uses.

In the methods and uses described herein, the enzyme and the substrate can be used in a molar ratio of 1:100 or higher, preferably 1:400 or higher, more preferably at least 1:1000.

The reaction is typically carried out in a suitable buffer system at a temperature that allows optimal enzyme activity, usually between ambient (20° C.) and 40° C.

Immobilizing enzymes on solid supports has a long history with a primary goal of lowering enzyme consumption by repetitively using the same batch of enzymes. In addition, site-separation of solid-phase immobilization reduces aggregation, leading to increased stability and activity of biocatalysts, and simplifies the purification by avoiding contamination of products by enzymes. Consequently, immobilized biocatalysts have been developed for industrial uses to a billion-scale market, such as immobilized lactase in food industry and immobilized lipase in biodiesel production. Compared with conventional industrial processes using chemical catalysts, immobilized enzymes are economically attractive and environmentally friendly.

There are three main-stream immobilization technologies, including attachment to carriers either or non-covalently, physical entrapment, and self-crosslinking. For biocatalysts such as PALs with an exposed substrate-binding surface for biomolecule-based substrates, strategies based on attachment to hydrophilic porous resins by either covalent-binding and affinity-binding methods are direct, convenient, and feasible to facilitate their performance in aqueous conditions.

The thus immobilized peptide ligases are stable, reusable and highly efficient in mediating macrocyclization and site-specific ligation reactions.

The inventors compared different methods to immobilize naturally-occurring butelase-1 and recombinantly expressed asparaginyl ligases VyPAL2. It was surprisingly found that immobilization of PALs overcomes the limitations of soluble enzymes, which include aggregation and autolysis into less active forms, albeit at a very slow rate at near neutral pH. The major advantages of immobilization on a solid support provide site separation and pseudo-dilution to prevent trans-autolytic degradation and enhance stability. The inventors confirmed these major advantages of the immobilized ligases: reusable >100 runs with undiminished enzymatic activity, enhanced stability and prolonged shelf-life, and simpler downstream purification process. More importantly, it was found that site-separation of immobilized enzymes permits the use of high enzyme concentrations to accelerate ligation reactions to complete in minutes, such as cyclization, cyclooligomerization and ligation reactions either under one-pot conditions or in a continuous flow-reactor. These advantages bode well in reducing amount of ligases, scale-up use for industrial scale and adaptation for nanodevices.

Accordingly, in one aspect of the invention, in the above-described methods and uses the polypeptides having ligase/cyclase activity may be immobilized on a suitable support material. Suitable support materials include various resins and polymers that are used in chromatography columns and the like. The support may have the form of beads or may be the surface of larger structure, such as a microtiter plate. Immobilization allows for a very easy and simple contacting with the substrate, as well as easy separation of enzyme and substrate after the synthesis. If the polypeptide with the enzymatic function is immobilized on a solid column material, the ligation/cyclization may be a continuous process and/or the substrate/product solution may be cycled over the column.

Accordingly, the present invention, in one aspect, also covers a solid support material comprising the isolated polypeptide according to the invention immobilized thereon. The solid support material may comprise a polymer resin, preferably in particulate form, such as those mentioned above. The isolated polypeptide can be immobilized on the solid support material by covalent or non-covalent interactions. The solid support may be, for example, an agarose bead.

In exemplary embodiments, the polypeptides having ligase/cyclase activity are glycosylated and may be immobilized by means of concanavalin A (Con A), a lectin (carbohydrate-binding protein) that is isolated from *Canavalia ensiformis* (jack bean). It binds specifically to α-D-mannose and α-D-glucose containing biomolecules, including glycoproteins and glycolipids. Said ConA protein is used in immobilized form on affinity columns to immobilize glycoproteins and glycolipids. Accordingly, in various embodiments, the isolated polypeptide having ligase/cyclase activity is glycosylated and non-covalently bound to a carbohydrate-binding moiety, preferably concanavalin A, coupled to the solid support material surface. Embodiments of glycosylated polypeptides of the invention have been described above.

The solid support materials described above can be used for the on-column cyclization and/or ligation of at least one substrate peptide or in a method for the cyclisation or ligation of at least one substrate peptide, comprising contacting a solution comprising the at least one substrate peptide with the solid support material described above under conditions that allow cyclization and/or ligation of the at least one substrate peptide. The substrate peptides are those described above and include also the above polypeptide substrate.

In various embodiments, the polypeptide having ligase or cyclase activity is glycosylated and the immobilization is facilitated by interaction with a carbohydrate-binding moiety, preferably a concanavalin A moiety or variant thereof, covalently linked to the solid support. In such embodiments, the polypeptide of the invention may be butelase-1 (comprising the amino acid sequence of SEQ ID NO:18 (active fragment) or SEQ ID NO:88 (full length sequence)) and the solid support may be an agarose bead.

In various other embodiment, the polypeptide having ligase or cyclase activity is biotinylated and the immobilization is facilitated by interaction with a biotin-binding moiety, preferably a streptavidin, avidin or neutravidin moiety or variant thereof, covalently linked to the solid support. Functionalization of the polypeptide with the biotin may be achieved using methods known in the art, such as functionalization with a biotin ester with N-Hydroxysuccinimide (NHS), such as succinimidyl-6-(biotinamido)hexanoate. In such embodiments, the polypeptide may be VyPAL2 having the amino acid sequence of SEQ ID NO:1 or 2 or variants thereof as defined herein. The solid support may be an agarose bead and the biotin-binding moiety may be an avidin variant, such as neutravidin (deglycosylated avidin).

In various other embodiments, the polypeptide having ligase or cyclase activity is immobilized on the solid support by reaction of free amino groups in the polypeptide, for example from lysine side chains, with an N-hydroxysuccinimide functional group on the surface of the solid support. The solid support may be agarose beads and the polypeptide may be VyPAL2 having the amino acid sequence of SEQ ID NO:1 or 2 or variants thereof as defined herein.

In various further aspects, the invention also features a method for increasing the protein ligase activity of a polypeptide having asparaginyl endopeptidase (AEP) activity, the method comprising the steps of substituting the amino acid residue at the position corresponding to position 126 of SEQ ID NO:1 with either a small hydrophobic residue or a G residue, preferably an A or a G residue. In various embodiments, the amino acid residue at the position corresponding to position 127 of SEQ ID NO:1 is A, in particular if the position corresponding to position 126 in SEQ ID NO:1 is G. In various embodiments, the amino acid residue at the position corresponding to position 127 of SEQ ID NO:1 is P, if the position corresponding to position 126 in SEQ ID NO:1 is A. In various embodiments the motif at the positions corresponding to positions 126 and 127 of SEQ ID NO:1 is not GP, but either AP, AA or GA. If the amino acid at the position corresponding to position 127 in SEQ ID NO:1 is not such that the motif AP, AA or GA is obtained, it may be substituted, too. As described above, it has been found that said position(s) within the LAD2 motif is a critical determinant for enzyme directionality, with GA and AP generally yielding enzymes with predominantly or exclusively ligase functionality.

In various embodiments, said method may also be a method for producing a polypeptide having protein ligase activity, the method comprising:

(i) providing a polypeptide having asparaginyl endopeptidase (AEP) activity; and (ii) introducing one or more amino acid substitutions into the polypeptide having asparaginyl endopeptidase (AEP) activity, wherein said substitutions comprise substituting the amino acid residue at the position corresponding to position 126 of SEQ ID NO:1 with an A or a G residue and optionally substituting the amino acid residue at the position corresponding to position 127 of SEQ ID NO:1 with either a P or an A residue, such that the amino acid sequence in the positions corresponding to positions 126/127 in SEQ ID NO:1 is either GA, AA or AP, preferably GA or AP.

Again, in such methods, the amino acid residue at the position corresponding to position 126 of SEQ ID NO:1 is A, in particular if the position corresponding to position 126 in SEQ ID NO:1 is G, or the amino acid residue at the position corresponding to position 127 of SEQ ID NO:1 is P, if the position corresponding to position 126 in SEQ ID NO:1 is A, with the motif at the positions corresponding to positions 126 and 127 of SEQ ID NO:1 being not GP, but preferably either AP, AA or GA. If the amino acid at the position corresponding to position 127 in SEQ ID NO:1 is not such that the motif AP, AA or GA is obtained, the method may comprise substituting said position in step (ii).

The polypeptide subjected to said method for increasing its ligase/cyclase activity may be an asparaginyl endopeptidase (AEP) and may, in various embodiments, comprise or consist of an amino acid sequence that shares at least 60, preferably at least 70, more preferably at least 80, most preferably at least 90% sequence homology or sequence identity with the amino acid sequence set forth in any one of SEQ ID Nos. 10-14 (VyAEP1-4; VcAEP) over its entire length. In various embodiments, the to-be-mutated polypeptide has an amino acid residue at the position corresponding to position 126 of SEQ ID NO:1 that is neither G nor A, such that the positions corresponding to positions 126 and 127 of SEQ ID NO:1 do not have the sequence motif GA or AP. It may however have the motif GP, which can then be substituted by GA, AA or AP in the described methods.

The invention also encompasses a transgenic organism, such as a plant, comprising a nucleic acid molecule encoding a polypeptide having protein ligase and/or cyclase activity as described herein. The polypeptide is preferably not naturally present in said host organism or host plant. Accordingly, the present invention also features transgenic organism/plants—with the exception of human beings—that express a heterologous polypeptide according to the invention.

In various embodiments such transgenic organisms/plants may further comprise at least one nucleic acid molecule encoding one or more peptides to be cyclized or one or more peptides to be ligated. These may be peptides as defined above in connection with the uses and methods of the invention. In one embodiment, the peptide to be cyclized is a linear precursor form of a cyclic cystine knot polypeptide, for example like those defined above. These precursors of peptides or polypeptides to be cyclized may be naturally present in said organism/plant but are preferably also artificially introduced, i.e. the nucleic acids encoding them are heterologous.

Such transgenic organisms/plants may, due to the co-expression of the enzyme and its substrate, therefore directly produce a cyclized peptide of interest.

All embodiments disclosed herein in relation to the polypeptides and nucleic acids are similarly applicable to the uses and methods described herein and vice versa.

The invention is further illustrated by the following non-limiting examples and the appended claims.

EXAMPLES

Materials and Methods

RNA Extraction and Construction of Vy Transcriptome and Search of AEP Analogs

Fresh *Viola yedoensis* fruits harvested in early September were subjected to RNA extraction by Trizol method and RNA samples were subjected to Illumina Hiseq sequencing (service provided by Beijing Genetic Institute). The sequenced database has been deposited to NCBI SRA database with accession no. PRJNA494974. After assembly using Trinity, data containing 14.69 GB bases was generated that gave 86,674 Unigenes. Using butelase 1 proenzyme amino acid sequence for homology search using the blastp server, eleven AEP-like mRNA sequences with E value lower than $1e^{-103}$, including six complete sequences containing starting and stop codons, three partial sequence with a full functional core domain and N- or C-terminal missing sequences and two truncated sequences with incomplete core domain were identified. Sequence alignment was performed using ClustalW in BioEdit. A search using butelase 1 proenzyme sequence resulted in over 500 hits with >60% sequence identity and >90% sequence coverage.

Cloning, Recombinant Expression and Purification of VyAEP/PALs and VcAEP in Bacteria VyAEP1 (Vy=*Viola yedoensis*), VyPAL1-3 and VcAEP (Vc=*Viola canadensis*) cDNA sequences without the predicted signal peptides were synthesized and cloned into pET28a(+) (GenScript, Beijing, China) with NdeI/XhoI restriction enzymes in-frame with an N-terminal His6-tag (Hemu et al. (2019) PNAS, Jun. 11, 2019, vol. 116, no. 24, 11737-11746). Point mutations were constructed using Q5 mutagenesis kit (NEB). Plasmids were transformed into SHuffle T7 *E. coli* that constitutively express DsbC and was pre-transformed with Erv1p expression plasmid pMJS9. Fresh culture of transformed cells with $OD_{600}$=0.4 were treated with 0.1% arabinose for 1 h to induce production of Erv1p followed by 0.1 mM IPTG treatment at 16° C. for 18-24 h to induce expression of the target proteins. Bacterial cells from a volume of 1 L induced cell culture were harvested by centrifugation at 6000 g for 15 min. A volume of 10 mL Lysis buffer (50 mM Na HEPES, 0.1 M NaCl, 1 mM EDTA, 5 mM β-mercapto-ethanol, 0.1% TritonX-100 at pH 7.5) were added to resuspend every 1 g cell pellet. Cell lysis was conducted by sonicating at 50% amplitude with 5 s/5 s pulse for 20 min on ice. Clarified cell lysate containing soluble proteins was loaded into self-packed column containing 1 mL COmplete nickel beads (Roche) that had been pre-equilibrated with chilled binding buffer (50 mM Na HEPES, 0.1 M NaCl, 1 mM EDTA, 5 mM β-ME, pH 7.5). After washing with 20 mL washing buffer (50 mM HEPES, 50 mM imidazole, 0.1 M NaCl, 1 mM EDTA, 5 mM β-ME, pH 7.5), His6-proteins were eluted with 4×2 mL elution buffer (50 mM HEPES, 500 mM imidazole, 0.1 M NaCl, 1 mM EDTA, 5 mM β-mercapto-ethanol, pH 7.5). 10× dilution of eluted proteins were loaded into GE HiTrap Q 5 mL column (GE life sciences) equilibrated with ion-exchange (IEX) buffer A (20 mM sodium phosphate buffer, pH 7.5, 1 mM EDTA, 5 mM mercapto-ethanol). The proteins were eluted with a gradient of IEX buffer B (1 M NaCl in 20 mM sodium phosphate buffer, pH 7.5, 1 mM EDTA, 5 mM β-mercapto-ethanol). The fractions containing the target protein were then concentrated four times prior to injection on a size exclusion chromatography (SEC) column (S75 16/60) equilibrated in 20 mM sodium phosphate buffer pH 7.55, 0.1 M NaCl, 5% glycerol, 1 mM EDTA, 5 mM β-mercapto-ethanol. The protein was then concentrated to about 1 mg/mL (equivalent to 20 μM) and stored at 4° C. or at −80° C. after addition of 20% sucrose and 0.1% Tween-20.

Cloning, Recombinant Expression and Purification of VyAEP/PALs in Insect Cells cDNAs were cloned into pFB-Sec-NH (Amp$^+$) donor vector in frame with a N-terminal His6-TEV tag and transformed into *E. coli* DH10Bac competent cells (Invitrogen) (Shrestha B et. al. (2008) Methods in Molecular Biology (Clifton, N.J.), pp 269-289). White colonies after X-gal blue/white selection (37° C., 48 h) were picked for colony-PCR using M13/FBAC2 primer mix and sequencing. Positive colonies were amplified for bacmid production using resuspension, lysis and neutralization buffers from QIAprep kit (Qiagen) followed by isopropanol precipitation. Extracted bacmids were transfected into Sf9 (*Spodoptera frugiperda*) insect cells for virus packaging using cellfectin and Grace's insect media (Gibco, Thermo Fisher Scientific). After 72 h, supernatant containing P0 viruses were harvested for infection. After three rounds of infection and amplification of viruses, 1 L SF9 insect cells at a concentration of $2.5×10^6$ cells/mL were infected with 25 mL P3 virus and cultured for 72 hours at 27° C., 120 rpm. Media containing secreted proteins were collected by centrifugation at 4000 g for 20 min. The pH of the supernatant was then set at 7.5, before injection on a GE excel affinity purification column (GE life sciences). After binding, the beads were washed using buffer A (20 mM Na HEPES pH 7.5, 150 mM NaCl and 5 mM β-mercapto-ethanol). Elution of the target protein was achieved with buffer A supplemented with 500 mM imidazole and the fractions containing the protein were diluted 10 times and subjected to IEX and SEC purification as described above.

Acid-Induced Auto-Activation

Activation was performed under various conditions with a pH buffers ranging from 4 to 7 at interval of 0.5, 50 mM sodium citrate buffer or 50 mM sodium phosphate buffer, with 1 mM EDTA and 5 mM β-mercapto-ethanol), at four temperatures (4, 16, 25 and 37° C.), times (15 min to 16 h) and using several surfactant additives (Tween-20, TritonX-100, N-lauroylsarcosine, and Brij35, at concentrations of 0.05 mM to 1 mM). The activated samples were analyzed with both SDS-PAGE and activity tests (amount of activated enzyme solution equivalent to 50 nM proenzyme, 20 μM GN14-SL, 20 mM sodium phosphate buffer, pH 6.5, 1 mM DTT, 1 mM EDTA, incubated at 37° C. for 5 min, followed by product formation by MALDI-TOF mass spectrometry). This allowed to determine that the optimal activation condition was acidification at pH 4.5 (50 mM sodium citrate buffer, 1 mM DTT, 1 mM EDTA, 0.1 M NaCl) at 4° C. for 12-16 h with 0.5 mM N-lauroylsarcosine. Subsequently, active enzymes were purified on a size exclusion chromatography column (S100 16/60) pre-equilibrated at pH 4.0 in the SEC buffer (20 mM sodium citrate buffer, 1 mM EDTA, 5 mM β-mercapto-ethanol, 5% glycerol, 0.1 M NaCl). Fractions containing the target proteins were neutralized to pH 5.0-6.5 after elution and stored at 4° C. or at −80° C. after addition of 20% sucrose until further use.

Determination of Auto-Activation Sites

Activated enzymes were subjected to SDS-PAGE and gel bands containing the active protein (migrating around 33-35 kDa) were cut into thin slice for in-gel digestion. The reduction and alkylation of disulfide bonds was performed in one-pot by addition of 5 mM DTT and 10 mM bromoethylamine in a buffer containing 1 M Tris-HCl at pH 8.6, by heating at 55° C. for 30 min. Tryptic digestion was performed with a quantity of 10 μg/mL trypsin (Pierce, MS grade, Thermo Scientific) at pH 7.8 at 37° C. overnight, which resulted in peptide bond cleavage mainly after Arg, Lys and Cys-ethylamine. Digested peptides were extracted from gel pieces with 50% acetonitrile (0.1% formic acid) and solvents were removed by Speedvac. Digested peptides were redissolved in 1% formic acid and subjected to LC-MS/MS sequencing on a Dionex UltiMate 3000 UHPLC system (Thermo Scientific Inc., Bremen, Germany) linked to Orbitrap Elite mass spectrometer (Thermo Scientific Inc., Bremen, Germany) as earlier described (Hemu X, et al. (2018) Methods Mol Biol. 2018; 1719:379-393; Serra A, et al. (2016) Sci Rep 6(1): 23005). Peptides were fragmented using higher-energy collisional dissociation (HCD). Resultant spectra from tryptic digestions were analyzed using PEAKS studio (version 7.5, Bioinformatics Solutions, Waterloo, Canada) where 10 ppm MS and 0.05 Da MS/MS tolerances were applied. Quality of peptide spectra was evaluated manually.

Characterization of enzyme activity at various pH values Enzyme activity was examined using purified active enzymes with protein concentration determined by $A^{280\,nm}$ absorbance (NanoDrop™ 2000 Spectrophotometer, Thermo Fisher Scientific). Reaction mixture containing 40 nM active enzyme, 20 μM substrate GN14-SL in the reaction buffers with pH values ranging from 4.5-8.0 (20 mM sodium citrate buffer or 20 mM sodium phosphate buffer, with 1 mM EDTA, 5 mM β-mercapto-ethanol) were incubated at 37° C. for 10 min and the reaction was quenched by adding 10× vol. of 0.2% trifluoroacetic acid (TFA) to reduce pH to a value <2. Reaction results were checked preliminarily using MALDI-TOF mass spectrometry and reaction products were quantitated by RP-HPLC on a C4 analytical column (Aries widepore 150×4.6 mm, Phenomenex). Peak areas were obtained in LC solution postrun analysis software (Shimadzu).

Substrate Specificity and Enzyme Kinetics

Peptide library 1 contains synthetic peptides GN14-$X_{(n)}$s and GD14-$X_{(n)}$ (GN14=SEQ ID NO:48) of which $X_{(n)}$ (n=0-4 residues) were derived from natural cyclotide precursors from Violaceae and Fabaceae species. Peptide library 2 contain 20 synthetic peptide GN12-XL (GN12=GLYRRGRLYRRN; SEQ ID NO:47) and Peptide library 3 contain 20 synthetic peptides GN12-GX (X for each of the 20 natural amino acids). VyPAL2-mediated cyclization reactions were performed with a fixed molar ratio of active enzyme:substrate (1:500) at pH 6.5 at 37° C. for 10 min and the reaction quenched with 0.2% TFA. Each substrate was tested in triplicate and quantitatively analyzed using RP-HPLC.

For kinetic studies, the cyclization reactions were conducted at pH 6.5 at 37° C. with a fixed concentration of active enzymes (10 nM) and various concentrations (2-20 μM) of the substrate GN14-SLAN (SEQ ID NO:48+SLAN). The yield of cyclization product cGN14 was quantified by RP-HPLC at every 20 s intervals and the initial rate $V_0$ (μM/s) was plotted against substrate concentration [S] (μM) to obtain the Michael-Menten curve in order to analyze the kinetic parameters ($k_{cat}$ and $K_M$) of each enzyme (GraphPad Prism).

Crystallization, Data Collection and Structure Determination of VyPAL2

VyPAL2 at a concentration of 10 mg/ml was screened for crystallization. Crystals suitable for X-ray crystallography appeared after 3 to 7 days in 20% PEG 3350, and 0.2 M magnesium formate dihydrate. Crystals were then mounted on a cryo-loop and flash frozen in liquid nitrogen. Diffraction data were collected at 100K on the MX2 Beamline at the Australian Synchrotron. Data processing was performed using the XDS software (Kabsch W (2010) Xds. Acta Crystallogr Sect D Biol Crystallogr 66(2):125-132). Data collection statistics are shown in Table S1 below. The structure was solved by the molecular replacement method, using OaAEP-C247A (PDB access code: 5H0I (Yang R, et al. (2017) J Am Chem Soc 139(15):5351-5358) monomer structure as a search probe. A clear solution containing two independent molecules in the asymmetrical unit was obtained using program Molrep (from the CCP4 suite of programs). Refinement was performed using Buster/TNT (GlobalPhasing Ltd) and manual corrections of the model were performed using the Coot program for molecular graphics (CCP4). Structure analysis and figure production were realized using PyMol (Schrödinger). Refinement statistics are presented in Table

TABLE S1

| Data collection and refinement statistics of VyPAL2. PDB code: 6IDV | |
| --- | --- |
| Crystallization condition | 20% PEG 3350, 0.2M $Mg^{2+}$ formate trihydrate |
| Wavelength (Å) | 0.953723 |
| Resolution (Å) | 50-2.4 (2.54-2.4) |
| Space group | C 2 |
| Unit cell | 156.8/69.8/104.4 90/110.2/90 |
| Measured reflections | 159400 (15614) |

TABLE S1-continued

Data collection and refinement statistics of VyPAL2.
PDB code: 6IDV

| Crystallization condition | 20% PEG 3350, 0.2M $Mg^{2+}$ formate trihydrate |
| --- | --- |
| Unique reflections | 41528 (4039) |
| Multiplicity | 3.8 (3.8) |
| Completeness (%) | 99.54 (97.63) |
| Mean I/sigma I (I) | 5.78 (1.26) |
| Rmerge (%)[a] | 21.9 (124.5) |
| $CC_{1/2}$ (%)[b] | 98.3 (48.4) |
| R-work[c] | 19.50 (29.87) |
| R-free[d] | 23.63 (37.81) |
| Number of non-hydrogen atoms | |
| Macromolecule | 7199 |
| Ligands | 177 |
| water | 427 |
| Protein residues | |
| RMS (bonds, Å) | 0.009 |
| RMS (angles, °) | 1.16 |
| Ramachandran favored (%) | 99.5 |
| Ramachandran outliers (%) | 0.5 |
| Average B-factor (Å2) | |
| Macromolecules | 45.9 |
| Ligands | 47.3 |
| solvent | 49.1 |

Values in parenthesis are those for the last shell
[a]$R_{merge} = \Sigma |I_j - <I> |/\Sigma I_j$, where $I_j$ is the intensity of an individual reflection, and $<I>$ is the average intensity of that reflection.
[b]$CC_{1/2}$ = percentage of correlation between intensities from random half-dataset (P. A. Karplus, K. Diederich, Science 2012, 336, 1030-1033).
[c]$R_{work} = \Sigma ||F_o| - |F_c||/\Sigma |F_c|$, where $F_o$ denotes the observed structure factor amplitude, and $F_c$ the structure factor amplitude calcualated from the model.
[d]$R_{free}$ is as for $R_{work}$ but calculated with 5% of randomly chosen reflections omitted from the refinement.

Molecular Dynamics (MD) Simulation

To obtain the equilibrated position of the modeled peptide substrate bound to VyPAL2, an initial VyPAL2-peptide complex modeled from reference (Schechter I, Berger A (1967) *Biochem Biophys Res Commun* 27(2):157-162) was subjected to an all-atom, explicit-solvent molecular dynamics simulation using NAMD 2.12 (Phillips J C, et al. (2005) *J Comput Chem* 26(16):1781-1802). The cyclized aspartic acid of VyPAL2 was replaced with a regular aspartic acid. The complex was simulated in a water box, where the minimal distance between the solute and the box boundary was 10 Å along all three axes. The charges of the solvated system were neutralized with counter-ions, and the ionic strength of the solvent was set to 150 mM NaCl using VMD (Humphrey W, Dalke A, Schulten K (1996) *J Mol Graph* 14(1):33-8, 27-8). The fully-solvated system was subjected to conjugate-gradient minimization for 10,000 steps, subsequently heated to 310 K in steps of 5 ps. The system was simulated for a total of 20 ns with the backbone atoms of the protein ligase, as well as the Ca atom of N343 of the peptide constrained, using a harmonic potential of the form $U(x) = k (x - x_{ref})^2$, where k is 1 kcal $mol^{-1}$ $Å^{-2}$ and $x_{ref}$ is the initial atom coordinates. Such constraints allow the side chains of VyPAL2 and the rest of the peptide substrate to move freely. All simulations were performed under the NPT ensemble assuming the CHARMM36 force field for the protein (Best R B, et al. (2012) *J Chem Theory Comput* 8(9):3257-3273) and assuming the TIP3P model for water molecules.

Enzyme, Beads and Substrates

Butelase-1 was extracted from plant material of *Clitoria ternatea* grown in the local herb garden. After a few rounds of size-exclusion and anion exchange chromatography on HPLC (Shimadzu) as described in previously protocol (Nguyen et al., *Nat Protoc* 2016, 11 (10), 1977-1988), purified butelase-1 was obtained and store in a pH 6.0 buffer containing 20 mM sodium phosphate, 0.15 M NaCl, 5 mM β-mercaptoethanol (β-ME) and 20% sucrose at 4° C. or −80° C. Recombinant VyPAL2 was expressed using Bac-to-Bac® Baculovirus system (Thermo Fisher Scientific) in Sf9 insect cells via a secretory pathway governed by the N-terminal GP64 signal peptide as previously described (Hemu et al., *Proc. Natl. Acad. Sci. U.S.A* 2019, 116 (24), 11737-11746). Expressed proenzymes were purified by Nickel-affinity binding on HisTrap Excel column (GE Healthcare), ion-exchange chromatography on HiTrap Q column (GE Healthcare) and size exclusion chromatography on HiLoad Superdex 75 column (GE Healthcare) using an NGC-FPLC System (Bio-Rad). Acid-induced autoactivation was performed at pH 4.5 at 4° C. overnight in the presence of 1 mM Dithiothreitol (DTT) and 0.5 mM N-lauroylsarcosine. Activated enzymes with molecular weight about 35 kDa was purified again by size-exclusion chromatography with a pH 4.0 citrate buffer. Purified active enzymes was stored in a pH 6.5 buffer containing 20 mM sodium phosphate, 0.1 M NaCl, 5 mM β-ME and 20% sucrose at 4° C. or −80° C.

All beads are from commercial sources. Pierce™ NHS-Activated Agarose beads (Thermo Fisher Scientific) have protein loading of 1-20 mg protein per mL. Pierce™ NeutrAvidin™ Agarose beads (Thermo Fisher Scientific) have protein loading of >8 mg biotinylated protein per mL. Concanavalin A (ConA) Agarose beads (G-Biosciences) have protein loading of 15-30 mg ConA per mL.

All peptide substrates used in the activity assays, including KN14-GL, GN14-HV, GN14-GL, GN14-SLAN, SFTI (D/N)-HV, RV7, and GLAK(FAM)RG (FAM, Fluorescein amidite) were synthesized by Fmoc chemistry on a Liberty-1 microwave synthesizer (CEM) using the protocol described before (Hemu, X.; Zhang, X.; Tam, J. P., *Org. Lett.* 2019). The protein substrate AS-48K (SEQ ID NO:19) was also synthesized chemically. Purified AS-48K was dissolved in 8 M urea and underwent refolding by dialysis (Hemu et al. *J. Am. Chem. Soc. Comm.* 2016, 138 (22), 6968-71) The protein substrate DARPin9_26-NGL was cloned into pET28a(+) vector with N-terminal His6-TEV-GLGSG sequence and C-terminal GSGSNGL tail (SEQ ID NO:49). Recombinant expression was done in Shuffle® T7 *E. coli* (New England Biolabs) after a 24 h induction by 0.1 mM IPTG at 16° C. Soluble proteins were extracted from cell lysate and purified by Ni-NTA affinity chromatography on a HisTrap HP 5 mL column (GE Life Sciences) and ion-exchange chromatography on a HiTrap Q 5 mL column (GE Life Sciences) using a NGC-FPLC System (Bio-Rad).

Thermostability of PALs

1 μg enzyme was mixed with 8× SYPRO orange fluorescent dye (Thermo Fisher Scientific) and diluted to a final volume of 25 μL with a series of buffers (50 mM sodium phosphate, 0.1 M NaCl, 5 mM β-ME) with pH ranged from 5 to 8 in a 96-well plate. pH buffers are ThermoFluor Assay was conducted in a Real-Time PCR Detection System (Bio-Rad) with temperature increased from 25 to 85° C. The melting temperature was calculated by plotting the change of RFU per degree against temperature.

Reactions Mediated by Soluble and Immobilized PALs

All reactions by soluble or immobilized PALs were conducted using a phosphate reaction buffer (20 mM sodium phosphate, pH 6.5, 0.1 M NaCl, 1 mM DTT) with the exception of ConA-Bu1, of which the ConA-reaction buffer contained additional 5 mM $CaCl_2$ and 5 mM MgCl2. The reaction pH was kept at 6.5 to maximize the enzyme activity. The reducing reagent DTT was added freshly before use. Reactions were performed at room temperature without heating to prevent degradation of reused enzymes. Reaction mixtures were analyzed by MALDI-TOF mass spectrometry or reversed-phase (RP) HPLC.

Immobilization on NHS-Activated Agarose Beads

Enzyme solutions were prepared with cold PBS (pH 7.4) to the concentration of 10 μM and added to NHS-Activated Agarose Dry Resin (75 mg requires 1 mL solution) and the preparation was shake slowly at 4° C. for 3 h. The mixture was then loaded into a chilled spin column and the flow through was collected. Beads were wash with 2× bead-volume of wash buffer (20 mM sodium phosphate, 1 mM DTT, 5% glycerol, pH 6.0 or 6.5) and the flow through was collected after binding and washing. Excessive NHS groups were blocked by socking beads in quenching buffer (1 M Tris-HCl, pH 7.4) for 1 h with gentle shaking at 4° C. Beads were washed again with reaction buffer, followed by the addition of 2× bead-volume of reaction buffer with 20% ethanol and keeping the slurry at 4° C.

Biotinylation and Immobilization on NeutrAvidin Agarose Beads

Enzyme solutions were prepared with cold PBS (pH 7.4) containing 5 mM β-ME to the concentration of 10 μM and mixed with 20-fold molar equivalent of Ezlink® NHS-LC-biotin (succinimidyl-6-(biotinamido)hexanoate, spacer length ~2.2 nm, Thermo Fisher Scientific) dissolved in DMF (stock concentration 10 mM). Biotinylation was conducted 4° C. overnight. Excessive NHS-LC-biotin was removed by buffer exchange with PBS (pH 7.4) using Vivaspin 10 kDa MWCO centrifuge concentrators (Sartorius, Germany). After buffer exchange, activity of biotinylated enzymes was compared with the untreated enzymes to show no activity loss. NA agarose beads was equilibrated with pH 6.5 reaction buffer. A mixture of 0.2 mL equilibrated beads with 1 mL biotinylated enzymes (5 μM) was prepared by gentle shaking at 4° C. for 3 h, followed by loading into a chilled spin column and collection of flow through. Beads were washed with 20× bead-volume of reaction buffer, and kept as a slurry at 4° C. in the presence of 2× bead-volume of reaction buffer with 5 mM β-ME and 20% ethanol.

Immobilization on Concanavalin A Agarose Beads

ConA beads were equilibrated with 10 bead-volume of cold equilibration buffer (1 M NaCl, 5 mM MgCl2, 5 mM CaCl2), pH 7.2, Mg ions were used here to substitute Mn ions) (Young, N. M., *FEBS Lett* 1983, 161, 247-250). Enzyme solutions were prepared with ConA reaction buffer to the concentration of 5 μM. One milliliter of enzyme solution was mixed with 1 mL of equilibrated ConA beads with slowly shaking at 4° C. for 3 h. The mixture was loaded into a chilled spin column and the flow through was collected. Beads were wash with 20× bead-volume of ConA reaction buffer and kept as a slurry at 4° C. in 2× bead-volume of ConA reaction buffer with 20% ethanol. Activity of immobilized enzymes stored with or without ethanol showed no significant difference.

Determination of Immobilization Yield

The concentration of unbound proteins in the flow through after binding and washing were determined using Nanodrop 2000 spectrophotometer (Thermo Fisher Scientific) by measuring the UV absorbance at 280 nm. For the flow through after washing, a concentration step using centrifugal filter (Vivaspin 10 kDa MWCO, Sartorius) was performed to bring up the protein concentration readable by spectrophotometer which has sensitivity threshold of 0.008 at 280 nm.

Determination of Activity of Immobilized PALs

Free butelase-1 (SEQ ID NO:18) and VyPAL2 (SEQ ID NO:2) were prepared in stock concentrations ranged from 1 to 8 μM. In each reaction, 1 μL enzyme stock was added to 100 μL 0.2 mM KN14-GL so the final enzyme concentrations ranged from 10 to 80 nM. After 5 min incubation at room temperature, the reaction was quenched by adding 0.5% TFA to bring down the pH to 2 and all the reaction solution was injected into analytical RP-HPLC (Aries-C18, 150×4.6 mm, 3 u, Shimadzu). The amount of cKN14 was calculated by the peak area at 220 nm in the HPLC profile. The initial reaction rate V was then calculated by increase of cKN14 concentration per second. A standard curve of reaction rate against enzyme concentration was plotted for each PAL, which reflects the turnover rate of free enzymes in the tested system. For the ease of calculation, the units of enzyme concentration and the corresponding reaction rate were converted based on the stock concentrations of free enzymes, as (μM) and (μM/s), respectively. Activity of immobilized PALs were examined using 10 μL beads in a 1 mL system with the same experimental setting. 100 μL out of 1 mL reaction solution was injected into RP-HPLC for product quantification. The reaction rate of each immobilized PAL was also converted into (μM/s) and compared with the stand curve to calculate the actual effective concentration. The activity ratio was calculated by the rate of immobilized PALs against rate of soluble PALs.

Accession codes. The nucleotide sequence for butelase 1 has been deposited in the GenBank database under the accession number KF918345.

Example 1: Mining AEPs in the *Violaceae* Transcriptomes and Initial Classification Using the "Gate-Keeper" Residue

*Violaceae* is one of the major cyclotide-producing plant families, suggesting the presence of PALs in their genomes. With the hope of identifying PALs, data mining on two plants from this family, *Viola yedoensis* (Vy) and *Viola canadensis* (Vc) was performed.

To obtain the transcriptome of *V. yedoensis*, total RNA was extracted from fresh fruits and sequenced followed by assembly of the database (NCBI SRA accession no. PRJNA494974). Precursor sequences of butelase 1 and OaAEP1b were used to search for sequences homologous to AEPs. A total of eleven AEP precursors were found from the *V. yedoensis* transcriptome, including six complete sequences, three partial sequences containing an intact core domain and two truncated sequences having an incomplete core domain that were discarded. The transcriptome of Vc is readily available in 1KP database and an AEP homolog (NJLF-2006002) named VcAEP was obtained by BLASTp using butelase 1 sequence. In order to cluster the nine Vy sequences and VcAEP, it was chosen to use the nature of the gate-keeper residue as a criterion: It was previously observed that mutation of a Cys residue (Cys-247) near the active site of OaAEP1 b (PDB access code: 5H0I), to larger amino acids (Thr, Met, Val, Leu, Ile) reduced ligation catalytic efficiency, while mutations to smaller residues such as Ala resulted in over a hundred-fold improved ligation efficiency (Yang R, et al. (2017) *J Am Chem Soc* 139(15): 5351-5358). Moreover, mutation of this "gate-keeper" residue into Gly resulted in an increased amount of hydrolysis product, suggesting that this site, located in the S2 substrate-binding pocket, plays an important role in modulating the enzyme function. Using butelase 1 amino-acids sequence to search for homologues in the NCBI data-bank returned more than 500 hits that share over 60% sequence identity, with 90% sequence coverage. Among them, more than 95% sequences carry Gly at the gate-keeper site, including both proteases and "dual-functional" ligases, which agreed with the fact that PALs are rare in plant AEPs.

Using this criterion, four *V. yedoensis* sequences were classified as putative VyAEPs due to the presence of Gly as gate-keeper and designated VyAEP1-4 (SEQ ID Nos. 10-13). The other five, designated VyPAL1-5 (SEQ ID Nos. 5-9) as well as VcAEP from *V. canadensis* (SEQ ID NO:14), were classified as putative VyPALs as they contain Val (like butelase 1) or Ile as gate-keeper residues.

Example 2: Production of Active Recombinant VyAEP and VyPALs

Based on sequence identity, these putative AEPs and PALs could be partitioned into four groups: VyAEP1 and 2 (98.9%), VyAEP3 and 4 (96.2%), VyPAL1,2,4 and 5 (>99%) and VyPAL3. VyPAL3 only shares <70% core sequence identity with other putative VyPALs but is 94% identical to VcAEP. VyAEP1, VyPAL1-3 and VcAEP were expressed for further studies. Recombinant expression was performed using both bacterial and insect cell systems, and the genes encoding complete amino acid sequences were cloned into the expression vectors, with the signal peptide substituted by a His-tag for affinity purification. Following metal-affinity, ion-exchange, and size-exclusion chromatography (see methods), bacterial and insect cell systems yielded ~0.5 mg/L and 10-20 mg/L of purified proenzymes, respectively.

Following purification, proenzymes were subjected to 12-16 h activation at 4° C., pH 4.5 in the presence of 0.5 mM N-lauroylsarcosine, 5 mM β-mercaptoethanol, and 1 mM EDTA. Such mild but prolonged treatment allows cleavage and degradation of the cap domain, preventing cap domain re-ligation. Activated enzymes were further purified using size-exclusion chromatography. The auto-activation sites of purified active VyPAL2 were determined by LC-MS/MS sequencing of the tryptic digested active forms. The Asn/Asp cleavages sites at both ends of the core domain were found to be N43/N46/D48 in the N-terminal pro-domain region, and D320/N333 in the linker region. This confirmed the complete removal of the inhibitory cap domain and the production of a mixture containing active forms, through protein processing at multiple sites.

Example 3: Ligase vs Protease Activity of VyAEP1 and VyPAL1-3

To determine the activity of VyAEP/PALs, a model peptide substrate termed "GN14-SL" GISTKSIPPISYRNSL (SEQ ID NO:59) with a MW of 1733 Da was prepared. GN14-SL contains the tripeptide recognition motif "NSL" at its C-terminus derived from the precursors of Vy cyclotides and analog of SFTI-1 (FIG. 1A). A fixed enzyme:substrate molar ratio (1:500) was used in all ligation reactions, which were performed at 37° C. for 10 min, at pH values ranging from 4.5 to 8.0 (at 0.5 intervals). The cyclization of GN14-SL was monitored using MALDI-TOF mass spectrometry. The yields of cyclic product cGN14 (MW: 1515 Da) and linear product GN14 (MW: 1533 Da) were quantified using RP-HPLC (FIG. 1B).

Among four PAL enzymes tested, VyPAL2 exhibited the best ligase activity, and did not produce any hydrolytic product at pH 5.5-8.0. At the optimal pH of 6.5, over 80% cyclization yield was observed (FIG. 1C). VyPAL1 also resulted in pure cyclization at pH 6-8 and, at the optimal pH of 7.0, about 80% cyclization yield is obtained. VyPAL3 displayed dominant hydrolysis activity at pH 4.5-5.5 and dominant ligase activity at pH 6.0-7.0. Its catalytic efficiency was the lowest among the three putative VyPALs, as only 20% substrate was converted into cyclized product at the optimal pH 7.0 in 10 min. As anticipated, the putative protease VyAEP1 displayed hydrolysis activity in the tested pH range of 4.5-8, although at near neutral and basic pH of 6.5-8, cyclization became noticeable. All four enzymes displayed varying degrees (2-40%, FIG. 1C) of protease activity at pH less than 5.0, reflecting the intrinsic proteolytic activity needed for acid-induced auto-activation.

Figure 2:
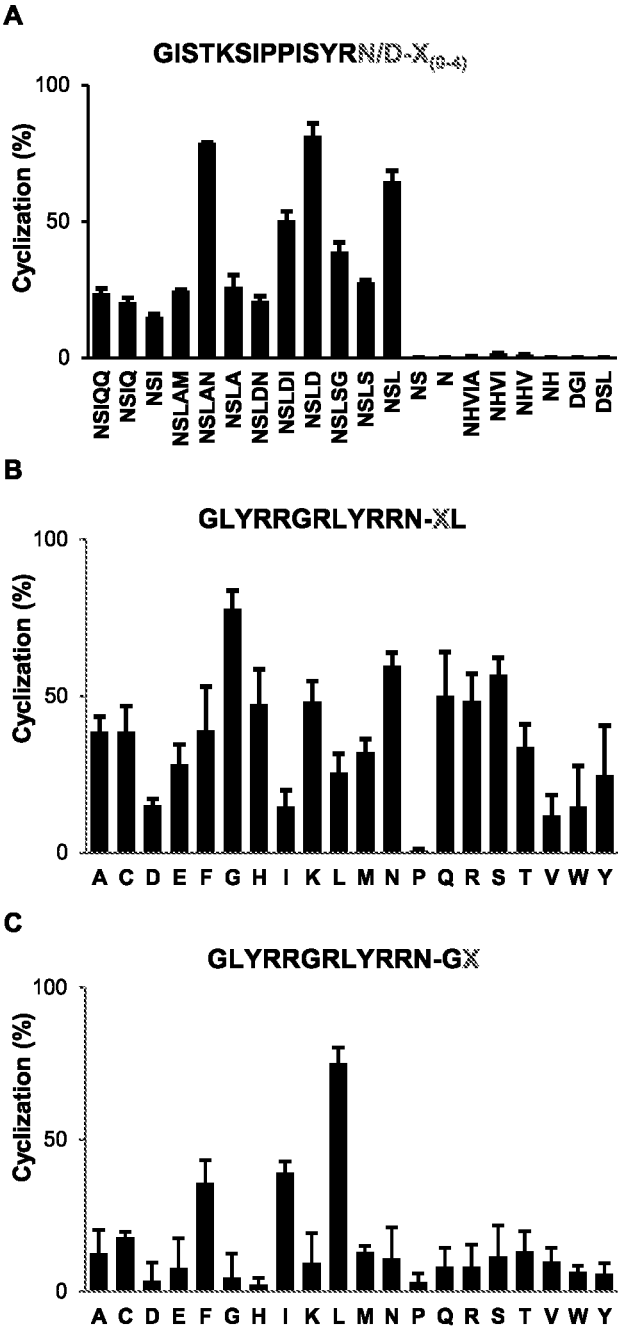
FIG. 2 shows the substrate specificity of VyPAL2 against (A) substrates carrying degenerated native recognition motifs derived from Vy and Ct cyclotides as set forth in SEQ ID Nos. 48 and 59-77, (B) substrates with 20 different amino acids at P1' position (X=20 AA; SEQ ID NO:78), (C) substrates with 20 different amino acids at P2' position (SEQ ID NO:79). All reactions were performed with a molar ratio of active VyPAL2:substrate=1:500 at pH 6.5, 37° C. for 10 min. Yields were quantitatively analyzed using RP-HPLC.
Figure 3:
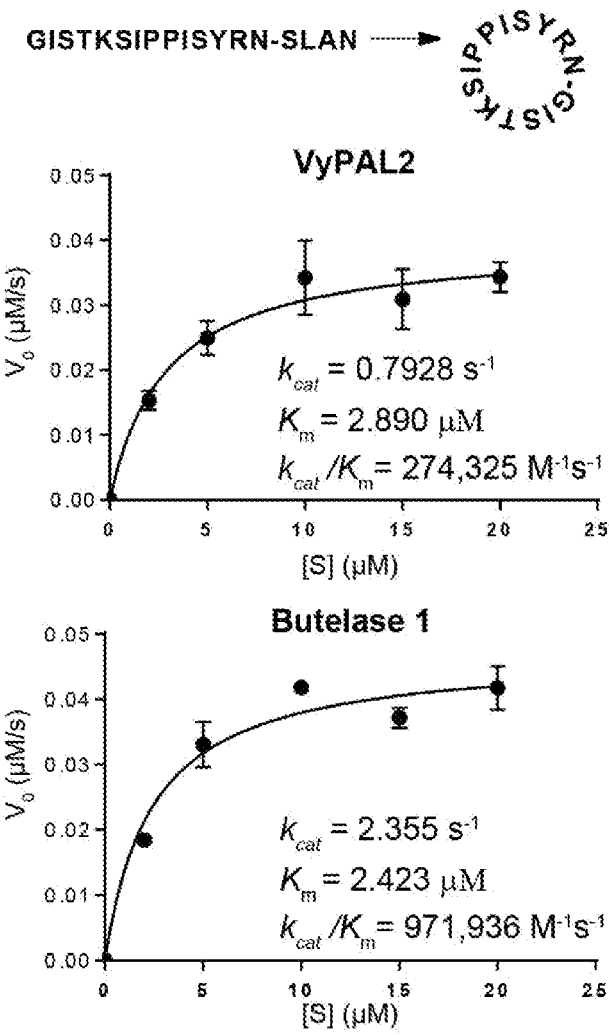
FIG. 3 shows the enzyme kinetics of VyPAL2 and butelase 1. HPLC-based kinetic study using the peptide substrate: GISTKSIPPISYRNSLAN (SEQ ID NO:60). A quantity of 50 nM purified active VyPAL2 (or butelase 1 extracted from plant (15)) was used for each reaction. The amount of cyclization product at each time point was determined using analytical RP-HPLC. Average initial rate ($V_0$) of three repeat experiments were used for Michaelis-Menten curve plotting.

Next, substrate specificity of VyPAL2 was studied, using three sets of peptide libraries (FIG. 2). Efficient cyclization required a minimum of three residues as the C-terminal recognition signal Asn-P1'-P2' (using the Schechter and Berger nomenclature (49). At P1', small amino acids especially Gly and Ser are favored, but not Pro. The P2' position favors the presence of hydrophobic or aromatic residues, such as Leu/Ile/Phe. The catalytic efficiency of VyPAL2 was examined using substrate GN14-SLAN (GISTKSIPPI-SYRNSLAN; SEQ ID NO:60) that gave 274,325 $M^{-1}s^{-1}$ when performing at pH 6.5 at 37° C., which was 3.5-fold less than butelase 1 (971,936 $M^{-1}s^{-1}$) (FIG. 3).

Example 4: Crystal Structure of VyPAL2

To understand the molecular mechanisms responsible for the differences in nature and efficiency between PALs and AEPs identified here, the crystal structure of the VyPAL2 proenzyme at a resolution of 2.4 Å was obtained. As expected, the structure displays the pro-legumain fold with the active domain on the N-terminus (residues 51 to 320) and the cap domain on the C-terminus (residues 344 to 483). These two domains are connected by a flexible linker (residues 321 to 343). The asymmetric unit contains two monomers of VyPAL2, forming a homodimer. In solution, this oligomeric form of VyPAL is present only at high protein concentrations (>5 mg/mL) as inferred from gel filtration results. As the protein was expressed in insect cells, several asparagine residues on the surface of the protein are glycosylated with one to three N-linked sugars (one N-acetylglucosamine (GlcNac), two GlcNac or two GlcNac and one Fucose) on Asn102, Asn145 and Asn237 respectively. Members of the C13 subfamily share a conserved α-β-α sandwich structure and a His172-Cys214 catalytic dyad located in a well-defined oxyanion hole. Peptide bond cleavage is catalyzed by the Cys thiol, which mediates an N-to-S acyl transfer to give the Asn-(S)-Cys thioester intermediate. The imidazole ring of His acts as a general base to accept a proton from the catalytic Cys.

The structure is similar to other PALs and AEPs such as OaAEP1b (PDB code: 5H0I), AtLEGγ (5NIJ, 5OBT), HaAEP1 (6AZT), or butelase 1 (6DH1), with an average root-mean-square deviation of atomic positions (r.m.s.d.) of 1.0 Å. Moreover, comparing the active domain alone returns r.m.s.d. values closer to an average 0.7 Å, showing that the core domain structure is strongly conserved. This further indicates that enzyme specificity is due to subtle variations in the substrate binding pockets that influence the stability of the S-acyl intermediate and accessibility of the catalytic water molecule. In the present pro-enzyme form, helix α6 (the first helix in the cap domain) makes an angle of about 90° with the linker peptide. At the junction between the linker region and the α6 helix, Gln343 is anchored inside the oxyanion hole (or S1 pocket). In recent structures of active forms of HaAEP1 and AtLEGγ, the bound substrate or inhibitor are shifted by a distance of about 2.5 Å compared to the linker region and covalently linked to the catalytic cysteine via a thioester bond.

Example 5: Modeling the Substrate-Enzyme Interactions Using Energy Minimization Structures of ligand-bound active forms of both HaAEP1 (PDB access code: 5OBT) and AtLEGγ (6AZT) indicated that only small conformational changes occur after activation of the protein and cap release. Therefore, the active form of the VyPAL2 ligase using the present crystal structure of VyPAL2 was modeled and residues Gly52 to Asn326, which are clearly visible in the electron density were included. This is also in line with the boundaries of the VyPAL2 active form determined using LC-MS, namely N43/N46/D48 and D320/N333. To obtain an initial model of a peptide substrate bound to the active form of the VyPAL2, the structure of the complex between AtLEGy and a peptide inhibitor (Zauner et al. (2018) *J Biol Chem* 293(23):8934-8946) having the sequence NH$_2$-LKVIH-NSL-COOH (SEQ ID NO:50) was used. The N-terminal sequence of this peptide corresponds to the original linker sequence and the C-terminal dipeptide is based on substrate specificity studies presented in FIG. 2. Energy minimization of the resulting complex with the peptide was then performed, constraining only the Ca atoms of the active protein. The alpha-carbon atom of the P1 Asn residue was fixed at the position found in AtLEGy and used as an anchor to maintain the substrate in the S1 pocket. Upon MD equilibration of the system for 20 ns, the N-terminal portion of the substrate "LKVIHN" (part of SEQ ID NO:50) was shifted due to repulsion between I244 from VyPAL2 and the substrate. As a result, the alpha-carbon atom of the Ile at the substrate P3 position is displaced by 3 Å. The C-terminal "SL" dipeptide on the other hand, becomes more extended, leading to a better fit of the peptide into the substrate binding pockets. This more stable and energetically favorable position for the modelled substrate was used to map the S1' and S2' pockets that define the recognition motifs both for protease and ligase activities. By analyzing the interface with the model substrate, residues of the active form of VyPAL2, that are lining the S4-S2' pockets were defined. The composition of S4 agreed with earlier works on AtLEGy and involved residues from both the disulfide-clamped poly-Pro loop (PPL) equivalent to c341 loop in caspase-1, and the MLA region (equivalent to c381 loop in caspase-1). On the other side of the S1 pocket, the S1' pocket is shaped by the amide groups of H172, G173 and A174 that accommodates the backbone atoms of P1' and P2' residues of the peptide. The S2' pocket is lined by Y185 and backbone atoms of G179 and M180, which favors binding of hydrophobic residues at the P'2 position. MD simulation shows that the interaction between hydrophobic Leu side-chain of the peptide and the phenol ring of Y185 is favored, which is in agreement with the preference for Ile/Val/Phe at P2' observed in the specificity study (FIG. 2C).

Example 6: Identification of Ligase-Activity Determinants in the S2 and S1' Pockets Although classified and confirmed as PALs, VyPAL1-3 displayed various levels of ligase activity in terms of both cyclization/hydrolysis ratio and catalytic efficiency. Thus, the structures of VyPAL1 and VyPAL3 were modeled using the experimental crystal structure of VyPAL2 as template. The resulting models are likely to be accurate given the sequence identity between these three proteins. Mapping the polymorphic residues on VyPAL1-3 structures indicates variations in the substrate-interacting surface located in the S2 and S1' pockets. One variation lies in the first residue of S2: Leu243 in VyPAL1 in lieu of the aromatic and bulky Trp present in both VyPAL2 and VyPAL3. In the same region, position 244 of VyPAL2 is either Ile or Val, introducing little variation in local hydrophobicity. Finally, the side-chain of residue at position 245 is facing a direction opposite from the S1 pocket (and the backbone atoms of VyPAL1-3 completely overlap), suggesting that this residue has little impact on catalysis. However, on the other side of the S1 pocket, a more drastic difference is observed in the vicinity of S'1 and S'2: Ala174-Pro175 in both VyPAL1 and 2 is replaced by Tyr175-Ala176 in VyPAL3.

Example 7: Selectively Improving the Ligase Activity of VyPAL3 and VcAEP

To validate experimentally these structural observations, VyPAL3 was first targeted: the "YA" dipeptide in the S1' region was mutated into "GA" as found in the butelase 1 sequence. As anticipated, this Y175G point mutation resulted in a strong and selective increase of ligation activity observed at lower pH (4.5-6), when compared with the wild-type VyPAL3 (FIG. 4). In addition, the catalytic efficiency was also significantly improved, with the maximum cyclization yield increasing from 20% to 80% (compare FIGS. 4C and 1C).

To further validate our hypothesis about the crucial role of the S1' region in determining ligase activity, VcAEP with predominantly protease activity and virtually absent ligase activity was targeted (FIG. 5A). The mutation Y168P169→A168P169 in its S1' region (equivalent to Y175A176 in VyPAL3) was introduced. The Y168A mutation drastically affected both the type of enzymatic activity and the catalytic efficiency (FIG. 5B) towards the GN14-SLDI substrate. The reaction with the wild-type VcAEP was performed using an enzyme to GN14-SLDI molar ratio of 1:200 for 5 h. In contrast, for VcAEP-Y168A the ratio was 1:2000 and reaction was quenched after 2 min incubation at 37° C. At near neutral pH, VcAEP-Y168A was able to convert over 60% substrate into its cyclic form, with less than 5% hydrolysis product formed (FIG. 5B).

Example 8: Preparation of Active Butelase-1 and VyPAL2

Two different sources of PALs were used, the naturally-occurring and activated butelase-1 isolated from plant (Nguyen et al. *Nat. Chem. Biol.* 2014, 10 (9), 732-738) and the insect-cell expressed VyPAL2 zymogen which requires an acid-induced step to be activated (Hemu et al. *Proc. Natl. Acad. Sci. U.S.A* 2019, 116 (24), 11737-11746). Butelase-1 used in this study was extracted from fresh plant tissues of *Clitoria ternatea* and purified via anion-exchange and size-exclusion chromatography as previously described (Nguyen et al. *Nat Protoc* 2016, 11 (10), 1977-1988). Recombinant VyPAL2 was expressed in the proenzyme form by baculo-virus expression system (Shrestha et al. In *Genomics Protocols*, Starkey, M.; Elaswarapu, R., Eds. Humana Press: Totowa, NJ, 2008; pp 269-289) in a secretory pathways using insect cells (Hemu et al., supra) The activated forms of VyPAL2 were obtained by an acid-induced auto-activation at pH 4.5 and purified by size-exclusion chromatography using a sodium citrate buffer at pH 4. Both butelase-1 and expressed VyPAL2 zymogen were glycosylated, and their glycosylated forms appear as bold bands that are larger than the calculated protein weights in SDS-PAGE (data not shown).

Example 9: Non-Covalent Immobilization of Active PALs

Butelase-1 is glycosylated at N94 and N286 with bulky heterogeneous glycans based on previous studies, which results in an increase of additional mass of about 6 kDa. The recombinant VyPAL2 is glycosylated at N102, N145 and N237 with small glycans, and which results in an additional increased mass of about 3 kDa (data not shown). Thus, lectin-beads were an obvious first choice and the most direct method to immobilize these two glycosylated PALs via affinity attachment. ConA is one of the most commonly and widely used plant lectins (Saleemuddin & Husain *Enzyme Microb. Technol.* 1991, 13 (4), 290-295; Rudiger & Gabius *Glycoconjugate J.* 2001, 18, 589-613). ConA-attachment is reversible, allowing the recovery of glycoenzymes using elution buffers containing mannosyl and glucosyl monosaccharides (Dulaney *Mol. Cell. Biochem.* 1978, 21 (1), 43-63) (FIG. 1A). For insoluble support, 6% crosslinked agarose beads were used as they are highly porous, hydrophilic, stable, inert to chemical and physical modifications, and their relatively large pore sizes allowing free diffusion of compounds <4000 kDa (Zucca et al. *Molecules* 2016, 21 (11)).

Affinity binding of glycoenzymes with ConA beads was performed by mixing 1 mg of freshly prepared ligases and 1 mL beads that were pre-equilibrated with a pH 6.5 ConA-reaction buffer and gently shake at 4° C. for 3 h. The low enzyme loading of 1 mg/mL (equivalent to ~27 μM of ligase) and the gentle shaking could facilitate diffusion of solutes. Beads were washed with ConA reaction buffer after binding. Butelase-1 immobilized on ConA-beads gave ConA-Bu1 1 in 39% yield as 61% of enzymes remained in the solution. In contrast, ConA-bound VyPAL2 was dissociated from beads quickly after a few rounds of washing. Consequently, ConA-Vy2 2 was excluded in all subsequent experiments.

The observed difference of ConA affinity to butelase-1 and VyPAL2 can be attributed to their glycosylated forms. Plant-derived butelase-1 contains the complex high-mannose N-glycans that bind to ConA with high affinity (Wilson *Curr. Opin. Struct. Biol.* 2002, 12 (4), 569-577; Strasser *Front Plant Sci* 2014, 5, 363). In contrast, the insect cell-expressed VyPAL2 contains simple N-glycans that binds to ConA with low affinity (Shi & Jarvis, *Curr Drug Targets.* 2007, 8 (10), 1116-1125) In the crystal structure of VyPAL2, confirmed glycans are not bigger than tri-saccharides. In addition, ConA-immobilized PALs are not suitable to catalyze reactions containing either soluble sugars or glycoproteins that may bind to ConA and exchange with the immobilized PALs.

For comparison, a second non-covalent immobilization was experimentally tested by exploiting the exceptionally high binding between biotin and avidin. The avidin-biotin binding is considered practically irreversible with dissociation constants in the range of $10^{-15}$ M. To eliminate non-specific lectin binding, a deglycosylated form of avidin, NeutrAvidin (NA), was used which retains the strong affinity binding of amine-linked biotins as the glycosylated avidin (FIG. 7B). This method required modifying some of the primary amines of PALs with biotins. The sequences of both active butelase-1 and VyPAL2 contain multiple Lys residues, which are not located close to the catalytic site or substrate binding surface. Thus, immobilization of PALs involving Lys-NH2 was not expected to hinder the catalytic site of PALs.

To biotinylate the lysine side chains, succinimidyl-6-(biotinamido)hexanoate (NHS-LC-biotin) was used for biotinylation of active butelase-1 and VyPAL2. The coupling reaction of N-hydroxy succimide ester (NHS-ester) to primary amines on the ligases is generally performed in basic conditions with pH ranging from 7.2 to 9.0. Since active PALs, regardless of whether they are plant-produced or insect-cell expressed, are less thermally stable in basic conditions, we performed the biotinylation at pH 7.4 at 4° C. to minimize degradation of the ligases. It was experimentally confirmed that biotinylated enzymes do not show activity loss. Affinity binding of the biotinylated butelase-1, Bu1(b), and biotinylated VyPAL2, Vy2(b) with NA beads was performed at pH 6.5 at 4° C. for 3 h. After immobilization, beads were washed with chilled pH 6.5 reaction buffer. This method resulted in 49% and 45% immobilization yield to give NA-Bu1(b) 3 and NA-Vy2(b) 4, respectively.

Example 10: Covalent Immobilization of Active PALs by Direct Coupling

The covalent approach confers an irreversible stable immobilization. We selected a well-established covalent immobilization method by coupling the primary amines on the N-terminus or Lys-side chains of PALs to an NHS-ester (FIG. 7C; Anderson et al. *J Am Chem Soc* 1964, 86 (9), 1839-1842; Cuatrecasas & Parikh *Biochemistry* 1972, 11 (12), 2291-2299). Similar to the previously described biotinylation of ligases with NHS-LC-biotin, the direct immobilization on NHS-activated agarose beads were performed at pH 7.4 at 4° C. overnight to give agarose-Bu1 5 and agarose-Vy2 6. The beads were then washed with chilled pH 6.5 reaction buffer. The results showed that this method directly immobilized active butelase-1 and VyPAL2 with 83% and 81% yield, respectively.

Example 11: Activity of Immobilized PALs

The activity of immobilized PALs was determined by comparing the initial reaction rate catalyzed by immobilized PALs with the rate catalyzed by their soluble counterparts. The ligase activity of free butelase-1 or VyPAL2 was measured by the macrocyclization of a model peptide substrate KN14-GL (KLGTSPGRLRYAGN-GL; SEQ ID NO:51) 7, sequence derived from a natural cysteine-rich peptide bleogen pB1[44] with a C-terminal PAL-recognition signal tripeptide NGL to give the end-to-end cyclic product cKN14 8 (FIG. 8). We used a substrate concentration of 0.2 mM to maximize the reaction rate because this concentration is much higher than the known Michaelis constant $K_M$ of butelase-1 and VyPAL2. Reaction was quenched after 5 min and the amount of cKN14 produced in each reaction was measured by RP-HPLC. The standard curves of reaction rate against the concentrations of free enzymes were plotted to calculate the turnover rate (FIG. 9). The effective concentration of immobilized PALs were determined by interpolating the measured reaction rates of immobilized PALs on the standard curve.

Table 2 summaries the results which show that non-covalent attachment of ConA-Bu1 1 and the NA-linked biotinylated enzymes NA-Bu1(b) 3 and NA-Vy2(b) 4 retained 50% and 20-30% activity of their soluble enzymes, respectively. The covalent attachment of agarose-Bu1 5 and agarose-Vy2 6 retained about 5% activity of their soluble enzymes. Direct attachment to agarose beads via a tetranoic spacer that was calculated to be about 1 nm only in agarose-Bu1 and agarose-Vy2 is perhaps too short (FIG. 7). In contrast, ConA-Bu1 has a spacer longer than 8 nm (ConA tetramer+glycan) (Becker et al. *J Bio Chem* 1975, 250 (4), 1513-1524) and the NeutrAvidin-immobilized NA-linked biotinylated enzymes have a spacer approximately 8 nm long (NeutrAvidin tetramer+NHS-LC-biotin) (Livnah et al. *Proc Natl Acad Sci USA* 1993, 90, 5076-5080). The correlation between the activity of immobilized PALs with the distance between the enzymes and solid supports suggested that short spacer may reduce enzyme mobility and accessibility of substrates. To improve the activity of immobilized enzymes via direct attachment method, a longer spacer needs to be exploited.

TABLE 2

Summary of immobilization yield and effective concentration of immobilized PALs

| | PAL Loading | | | |
| | Obs. Conc (μM) | Yield (%) | Effective Conc (μM) | Ratio (%) |
| --- | --- | --- | --- | --- |
| Non-covalent | | | | |
| ConA-Bu1    1 | 10.5 | 39 | 4.6 | 44 |
| NA-Bu1(b)   3 | 13.2 | 49 | 3.3 | 25 |
| NA-Vy2(b)   4 | 12.1 | 45 | 2.8 | 23 |
| Covalent | | | | |
| Agarose-Bu1 5 | 22.4 | 83 | 1.1 | 5 |
| Agarose-Vy2 6 | 21.8 | 81 | 0.6 | 3 |

Expected maximal PAL concentration on beads is 1 mg/mL ≈ 27 μM.
Obs. Conc = observed protein loading of PAL on beads.
Yield = Observed concentration/expected maximal concentration.
Ratio = V(immobilized enzyme)/V(free enzyme) = Effective Conc./Obs. Conc.
ConA = concanavalin A.
NA = NeutrAvidin.
(b) = biotin.

Example 12: Immobilized PALs Display High Operational Stability and Prolonged Storage Stability Solid-phase immobilization of PALs would minimize self-aggregation and auto-proteolysis, and in turn, enhanced stability. To show the operational stability and reusability, each immobilized PAL was reused 100 times and their efficacy in the cyclization of linear peptide KN14-GL 7 analyzed.

In each run, the same batch of immobilized-PAL agarose beads was used, and the reaction mixture was analyzed using C18 reversed-phase HPLC (FIG. 10A). FIG. 10B summarizes the product analysis of five immobilized PALs, all of which showed that >90% catalytic activity was retained after 100 runs.

To show the prolonged shelf-life of immobilized PALs stored at 4° C., their ligase activity was monitored every week for a period of two months in cyclizing the peptide substrate GN14-HV (SEQ ID NO: 52; GISTKSIPPISYRN-HV, 9) or GN14-SLAN (SEQ ID NO:53; GISTKSIPPI-SYRN-SLAN, 10) to yield cGN14 11 by MALDI-TOF mass spectrometry. FIG. 11 shows that immobilized PALs are more stable than their soluble counterparts in prolonged storage. All five immobilized PALs, retained >90% activity after nine weeks. In contrast, butelase-1 or VyPAL2 lost about 30% activity after a two-month storage under the same storage conditions.

It was found that addition of a reducing reagent, such as Tris(2-carboxyethyl)phosphine (TCEP), dithiothreitol (DTT) or β-mercaptoethanol (β-ME), is crucial for keeping the catalytic Cys of active PALs in the reduced form. Both soluble and immobilized PALs stored in a non-reducing buffer lost activity in two weeks due to the oxidation of the catalytic cysteinyl sulfhydryl. Once the sulfhydryl is oxidized leading to inactivation, the ligase activity can be restored, sometimes but not always, after treating with buffers containing one or more reducing reagents. It was also observed that immobilized butelase-1 is slightly more stable than immobilized VyPAL2, suggesting that plant-derived PALs may benefit from higher-level of glycosylation which enhances their molecular stability from proteolytic degradation.

Example 13: Applications of Immobilized PALs for Ligation Reactions

The reusability of immobilized PALs allows us to use a much higher enzyme concentration than their soluble counterpart to accelerate the catalytic ligation reactions. In the following five examples NeutrAvidin-immobilized NA-Bu1 (b) 3 and NA-Vy2(b) 4 were used to showcase this advantage of immobilized PALs for cyclization and ligation, as well as their uses in a continuous flow system.

The first example was a cyclization reaction of a SFTI-substrate containing a sterically hindered Pro at the P2 position, which causes a slower ligation reaction than those substrates with a less hindered amino acid occupying the same P2 position. FIG. 12A shows that butelase-1-mediated cyclization of a 14-residue disulfide-containing peptide SFTI analog, GRCTKSIPPICFPN-HV 12 (SEQ ID NO:54), is 50% complete to yield the cyclic SFTI 13 after 30 min. In contrast, increasing the effective concentration of the NeutrAvidin-immobilized butelase-1 NA-Bu1(b) 3 five-fold resulted in accelerating the cyclization ligation to complete within 10 min.

In the second example, the soluble and NeutrAvidin-immobilized butelase 1 was compared for cyclizing a 70-residue protein, circular bacteriocin AS-48. This circular bacteriocin is a highly sought-after food preservative produced by the lactic bacteria for its ability to kill broad-spectrum of microorganisms. AS-48 is the second largest naturally-occurring head-to-tail macrocycles known. The free butelase-1 was used to cyclize the folded AS-48K 14 (SEQ ID NO:19), which contains an N-terminal dipeptide and C-terminal hexapeptide sequence for butelase-1 recognition. Using an enzyme:substrate ratio of 1:100 at 37° C., the reaction was complete in 1 h whereas increasing effective concentration of NA-Bu1(b) five-fold of the free butelase-1 accelerated the completion of cyclization in 10 min in a 83% isolated yield of cyclic AS-48 15 (FIG. 12B).

The third example was PAL-mediated cyclooligomerization of peptides. This reaction involves both oligomerization and head-to-tail cyclization of the nascent oligomers. Using this approach the formation of bioactive cyclo-oligomeric peptides using a simple peptidyl monomer as building block was demonstrated. The cyclooligomerization of RV7 (RLYRNHV, 16; SEQ ID NO:55), using the NeutrAvidin-immobilized butelase NA-Bu1(b) in an enzyme:substrate ratio of 1:100, completed within 40 min to yield 83% cyclodimer c17 and 8% cyclotrimer c18 of RLYRN (FIG.

13). In contrast, the reaction using butelase-1 with an enzyme:substrate ratio of 1:500, in which effective concentration of the soluble form was five-fold lower the immobilized form, did not complete after 4 h (data not shown).

In the last two examples, the PAL-mediated intermolecular ligation was used in a continuous-flow system. Unlike cyclization reactions which have the advantage of high effective concentrations, intermolecular ligations would require both high concentrations of substrates and enzymes, and thus immobilized PALs can be reused in high concentration to overcome this limitation. Using a self-packed column (internal diameter 4 mm) with NA-Vy2(b) 4 beads, peptide ligation of Ac-RYANGI 19 (10 µM; SEQ ID NO:56) was performed with a synthetic fluorescent peptide GLAK (FAM)RG 20 (100 µM; SEQ ID NO:57) under different flow rate from 0.05 to 0.5 mL/min (FIG. 14A). At flow rate of 0.05 mL/min, we observed completed ligation reaction to yield Ac-RYANGLAK(FAM)RG 21 (SEQ ID NO:58). Finally, we used this packed-bed column of NA-Vy2(b) to label a 193-residue recombinant protein, anti-Her2 DARPin9_26-NGL 22 (SEQ ID NO:49) with GLAK(FAM)RG 20. A reaction containing 1 µM DARPin9_26-NGL and 5 µM GLAK(FAM)RG afforded 78% yield of DARPin9_26-NGLAK(FAM)RG 23 with a flow rate of 20 µL/min (FIG. 14B). The unreacted peptides were readily removed from ligation products by dialysis or centrifugal filters with molecular weight cut off >3 kDa.

---

The invention claimed is:

1. A recombinant polypeptide having protein ligase activity comprising:
   (i) the amino acid sequence as set forth in SEQ ID NO: 1; or
   (ii) an amino acid sequence of at least 90% identity with SEQ ID NO:1 and comprises:
   (a) the amino acid residue W or Y at position 195, the amino acid residue I, C, A or V at position 196, and the amino acid residue T, A or V at position 197 of SEQ ID NO:1;
   (b) the amino acid residue A or G at position 126 and, the amino acid A or P at position 127 of SEQ ID NO:1, but not GP at positions 126 and 127 of SEQ ID NO: 1; and
   (c) at least two of the amino acid residues selected from: the amino acid residue N at position 19 of SEQ ID NO: 1; the amino acid residue H at position 124 of SEQ ID NO: 1; and the amino acid residue C at position 166 of SEQ ID NO:1.

2. The recombinant polypeptide of claim 1, wherein the recombinant polypeptide comprises:
   (i) the amino acid sequence set forth in SEQ ID NO:2 or SEQ ID NO:3; or (ii) an amino acid sequence of at least 90% identity with SEQ ID NO:2 or 3 and comprises:

(a) the amino acid residue W or Y at position 195, the amino acid residue I, C, A or V at position 196, and the amino acid residue T, A or V at position 197 of SEQ ID NO:1;

(b) the amino acid residue A or G at position 126 and, the amino acid residue A or P at position 127 of SEQ ID NO: 1, but not GP at positions 126 and 127 of SEQ ID NO: 1; and (c) at least two of the amino acid residues selected from: the amino acid residue N at position 19 of SEQ ID NO: 1; the amino acid residue H at position 124 of SEQ ID NO: 1; and the amino acid residue C at position 166 of SEQ ID NO:1.

3. The recombinant polypeptide of claim 1, wherein said polypeptide comprises: (i) the amino acid residue A at position 126 and the amino acid A or P at position 127 of SEQ ID NO: 1, (ii) the amino acid residue G at position 126 and the amino acid A at position 127 of SEQ ID NO:1, (iii) the amino acid residue W or Y at position 195, the amino acid residue I or V at position 196, and the amino acid residue T, A or V at position 197 of SEQ ID NO: 1, (iv) the amino acid residue W at position 195 of SEQ ID NO: 1, the amino acid residue I or V at position 196 of SEQ ID NO: 1, and the amino acid residue T at position 197 of SEQ ID NO:1, (v) the amino acid residues R at position 21, H at position 22, D at position 123, E at position 164, S at position 194, and D at position 215 of SEQ ID NO:1, (vi) the amino acid residues C at position 199 and 212 of SEQ ID NO:1, or combinations thereof.

4. A nucleic acid molecule encoding the polypeptide according to claim 1.

5. A vector comprising the nucleic acid molecule of claim 4.

6. The vector of claim 5, wherein said vector further comprises regulatory elements for controlling expression of said nucleic acid molecule.

7. A host cell comprising the nucleic acid molecule of claim 4, wherein, optionally, the host cell is an insect cell.

8. A method for cyclizing a peptide or for ligating at least two peptides, the method comprising incubating said peptide or said at least two peptides with the recombinant polypeptide of claim 1 under conditions that allow cyclization of said peptide or ligation of said peptides.

9. A solid support material comprising the recombinant polypeptide according to claim 1 immobilized thereon.

* * * * *